(12) United States Patent
DeRosa et al.

(10) Patent No.: US 11,104,652 B2
(45) Date of Patent: *Aug. 31, 2021

(54) STEREOCHEMICALLY ENRICHED COMPOSITIONS FOR DELIVERY OF NUCLEIC ACIDS

(71) Applicant: TRANSLATE BIO, INC., Lexington, MA (US)

(72) Inventors: Frank DeRosa, Chelmsford, MA (US); Shrirang Karve, Waltham, MA (US); Michael Heartlein, Boxborough, MA (US)

(73) Assignee: Translate Bio, Inc., Lexington, MA (US)

( * ) Notice: Subject to any disclaimer, the term of this patent is extended or adjusted under 35 U.S.C. 154(b) by 379 days.

This patent is subject to a terminal disclaimer.

(21) Appl. No.: 16/178,142

(22) Filed: Nov. 1, 2018

(65) Prior Publication Data

US 2019/0185435 A1 Jun. 20, 2019

Related U.S. Application Data

(63) Continuation of application No. 14/749,027, filed on Jun. 24, 2015, now Pat. No. 10,138,213.

(60) Provisional application No. 62/016,512, filed on Jun. 24, 2014.

(51) Int. Cl.
| | | |
|---|---|---|
| *A61K 9/127* | (2006.01) | |
| *C07D 241/08* | (2006.01) | |
| *A61K 31/7088* | (2006.01) | |
| *A61K 47/22* | (2006.01) | |
| *A61K 31/495* | (2006.01) | |
| *A61K 31/7105* | (2006.01) | |

(52) U.S. Cl.
CPC .......... *C07D 241/08* (2013.01); *A61K 9/1271* (2013.01); *A61K 9/1272* (2013.01); *A61K 31/495* (2013.01); *A61K 31/7088* (2013.01); *A61K 31/7105* (2013.01); *A61K 47/22* (2013.01)

(58) Field of Classification Search
None
See application file for complete search history.

(56) References Cited

U.S. PATENT DOCUMENTS

| | | |
|---|---|---|
| 2,647,121 A | 7/1953 | Jacoby |
| 2,717,909 A | 9/1955 | Kosmin |
| 2,819,718 A | 1/1958 | Goldman |
| 2,844,629 A | 7/1958 | William et al. |
| 3,096,560 A | 7/1963 | Liebig |
| 3,535,289 A | 10/1970 | Yoshihara et al. |
| 3,614,954 A | 10/1971 | Mirowski et al. |
| 3,614,955 A | 10/1971 | Mirowski |
| 3,656,185 A | 4/1972 | Carpentier |
| 3,805,301 A | 4/1974 | Liebig |
| 3,945,052 A | 3/1976 | Liebig |
| 3,995,623 A | 12/1976 | Blake et al. |
| 4,013,507 A | 3/1977 | Rembaum |
| 4,022,833 A | 5/1977 | Diana et al. |
| 4,072,146 A | 2/1978 | Howes |
| 4,096,860 A | 6/1978 | McLaughlin |
| 4,099,528 A | 7/1978 | Sorenson et al. |
| 4,106,129 A | 8/1978 | Carpentier et al. |
| 4,134,402 A | 1/1979 | Mahurkar |
| 4,140,126 A | 2/1979 | Choudhury |
| 4,180,068 A | 12/1979 | Jacobsen et al. |
| 4,182,833 A | 1/1980 | Hicks |

(Continued)

FOREIGN PATENT DOCUMENTS

| | | |
|---|---|---|
| CA | 2518132 A1 | 3/2006 |
| CA | 2 769 408 | 2/2011 |

(Continued)

OTHER PUBLICATIONS

U.S. Appl. No. 61/494,714, filed Jun. 8, 2011, Guild.

(Continued)

*Primary Examiner* — Ileana Popa
(74) *Attorney, Agent, or Firm* — Proskauer Rose LLP; Fangli Chen

(57) ABSTRACT

Provided, in part, is a composition comprising one or more chemical entities of formula I, each of which is a compound of formula I:

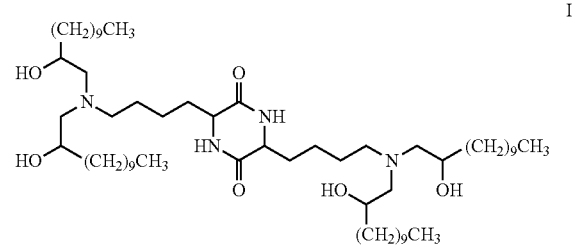

a pharmaceutically acceptable salt thereof, a solvate thereof, or a solvate of a pharmaceutically acceptable salt thereof, the composition characterized in that greater than a first threshold amount of the total amount of chemical entities of formula I in the composition: are chemical entities of formula I.a, wherein the first threshold amount is 50%; or are chemical entities of formula I.b.1, wherein the first threshold amount is 25%; or are chemical entities of formula I.b.2, wherein the first threshold amount is 25%, wherein the chemical entities of formula I.a, I.b.1, and I.b.2, are described herein, and methods of using such compositions, for example, for the delivery of a polynucleotide in vivo.

12 Claims, 1 Drawing Sheet
Specification includes a Sequence Listing.

(56) References Cited

U.S. PATENT DOCUMENTS

| | | |
|---|---|---|
| 4,227,533 A | 10/1980 | Godfrey |
| 4,284,459 A | 8/1981 | Patel et al. |
| 4,308,085 A | 12/1981 | Horhold et al. |
| 4,323,525 A | 4/1982 | Bornat |
| 4,335,723 A | 6/1982 | Patel |
| 4,339,369 A | 7/1982 | Hicks et al. |
| 4,355,426 A | 10/1982 | MacGregor |
| 4,373,071 A | 2/1983 | Itakura |
| 4,375,817 A | 3/1983 | Engle et al. |
| 4,385,631 A | 5/1983 | Uthmann |
| 4,401,472 A | 8/1983 | Gerber |
| 4,401,796 A | 8/1983 | Itakura |
| 4,406,656 A | 9/1983 | Hattler et al. |
| 4,458,066 A | 7/1984 | Caruthers et al. |
| 4,475,972 A | 10/1984 | Wong |
| 4,530,113 A | 7/1985 | Matterson |
| 4,550,447 A | 11/1985 | Seiler, Jr. et al. |
| 4,562,596 A | 1/1986 | Kornberg |
| 4,568,329 A | 2/1986 | Mahurkar |
| 4,571,241 A | 2/1986 | Christopher |
| 4,601,718 A | 7/1986 | Possis et al. |
| 4,647,416 A | 3/1987 | Seiler, Jr. et al. |
| 4,662,382 A | 5/1987 | Sluetz et al. |
| 4,701,162 A | 10/1987 | Rosenberg |
| 4,710,169 A | 12/1987 | Christopher |
| 4,720,517 A | 1/1988 | Ravichandran et al. |
| 4,737,323 A | 4/1988 | Martin et al. |
| 4,762,915 A | 8/1988 | Kung et al. |
| 4,782,836 A | 11/1988 | Alt |
| 4,856,521 A | 8/1989 | Irnich |
| 4,860,751 A | 8/1989 | Callaghan |
| 4,873,370 A | 10/1989 | Chiu |
| 4,878,908 A | 11/1989 | Martin et al. |
| 4,892,540 A | 1/1990 | Vallana |
| 4,897,355 A | 1/1990 | Eppstein et al. |
| 4,946,857 A | 8/1990 | Kanehira et al. |
| 4,960,409 A | 10/1990 | Catalano |
| 4,966,945 A | 10/1990 | Drawert et al. |
| 5,024,671 A | 6/1991 | Tu et al. |
| 5,025,005 A | 6/1991 | Nomura et al. |
| 5,047,540 A | 9/1991 | Kamata et al. |
| 5,101,824 A | 4/1992 | Lekholm |
| 5,104,399 A | 4/1992 | Lazarus |
| 5,116,360 A | 5/1992 | Pinchuk et al. |
| 5,138,067 A | 8/1992 | Kamata et al. |
| 5,151,105 A | 9/1992 | Kwan-Gett |
| 5,153,319 A | 10/1992 | Caruthers et al. |
| 5,171,678 A | 12/1992 | Behr et al. |
| 5,176,661 A | 1/1993 | Evard et al. |
| 5,200,395 A | 4/1993 | Eto et al. |
| 5,261,419 A | 11/1993 | Osypka |
| 5,282,824 A | 2/1994 | Gianturco |
| 5,284,491 A | 2/1994 | Sutton et al. |
| 5,300,022 A | 4/1994 | Klapper et al. |
| 5,314,430 A | 5/1994 | Bardy |
| 5,330,768 A | 7/1994 | Park et al. |
| 5,334,761 A | 8/1994 | Gebeyehu et al. |
| 5,352,461 A | 10/1994 | Feldstein et al. |
| 5,395,619 A | 3/1995 | Zalipsky et al. |
| 5,405,363 A | 4/1995 | Kroll et al. |
| 5,405,379 A | 4/1995 | Lane |
| 5,455,352 A | 10/1995 | Huellmann et al. |
| 5,464,924 A | 11/1995 | Silvis et al. |
| 5,503,852 A | 4/1996 | Steiner et al. |
| 5,528,023 A | 6/1996 | Butturini et al. |
| 5,607,385 A | 3/1997 | Francischelli et al. |
| 5,609,624 A | 3/1997 | Kalis |
| 5,614,548 A | 3/1997 | Piantadosi et al. |
| 5,626,869 A | 5/1997 | Nyqvist et al. |
| 5,631,018 A | 5/1997 | Zalipsky et al. |
| 5,693,088 A | 12/1997 | Lazarus |
| 5,697,953 A | 12/1997 | Kroll et al. |
| 5,700,437 A | 12/1997 | Fujii et al. |
| 5,700,642 A | 12/1997 | Monforte et al. |
| 5,705,188 A | 1/1998 | Junichi et al. |
| 5,705,385 A | 1/1998 | Bally et al. |
| 5,736,573 A | 4/1998 | Galat |
| 5,744,335 A | 4/1998 | Wolff et al. |
| 5,772,694 A | 6/1998 | Bokros et al. |
| 5,776,165 A | 7/1998 | Ripart |
| 5,776,747 A | 7/1998 | Schinstine et al. |
| 5,874,105 A | 2/1999 | Watkins et al. |
| 5,885,613 A | 3/1999 | Holland et al. |
| 5,910,168 A | 6/1999 | Myers et al. |
| 5,916,208 A | 6/1999 | Luther et al. |
| 5,965,434 A | 10/1999 | Wolff et al. |
| 5,976,567 A | 11/1999 | Wheeler |
| 5,976,569 A | 11/1999 | Milstein |
| 5,981,501 A | 11/1999 | Wheeler et al. |
| 6,034,056 A | 3/2000 | Dutta |
| 6,055,454 A | 4/2000 | Heemels |
| 6,067,471 A | 5/2000 | Warren |
| 6,071,497 A | 6/2000 | Steiner et al. |
| 6,090,384 A | 7/2000 | Ra et al. |
| 6,096,070 A | 8/2000 | Ragheb et al. |
| 6,096,075 A | 8/2000 | Bokros et al. |
| 6,120,799 A | 9/2000 | McDonald et al. |
| 6,152,955 A | 11/2000 | KenKnight et al. |
| 6,169,923 B1 | 1/2001 | Kroll |
| 6,176,877 B1 | 1/2001 | Buchanan et al. |
| 6,204,297 B1 | 3/2001 | Tracy et al. |
| 6,271,209 B1 | 8/2001 | Smith et al. |
| 6,299,604 B1 | 10/2001 | Ragheb et al. |
| 6,331,381 B1 | 11/2001 | Milstein |
| 6,335,199 B1 | 1/2002 | Bischoff et al. |
| 6,358,278 B1 | 3/2002 | Brendzel et al. |
| 6,370,434 B1 | 4/2002 | Zhang et al. |
| 6,371,983 B1 | 4/2002 | Lane |
| 6,444,226 B1 | 9/2002 | Steiner et al. |
| 6,534,484 B1 | 3/2003 | Wheeler et al. |
| 6,696,424 B1 | 2/2004 | Wheeler |
| 6,756,055 B2 | 6/2004 | McDonald et al. |
| 6,815,432 B2 | 11/2004 | Wheeler et al. |
| 6,821,530 B2 | 11/2004 | Koob et al. |
| 6,887,665 B2 | 5/2005 | Trulson et al. |
| 6,998,115 B2 | 2/2006 | Langer et al. |
| 7,022,214 B2 | 4/2006 | Olech |
| 7,084,303 B2 | 8/2006 | Watanabe et al. |
| 7,422,902 B1 | 9/2008 | Wheeler et al. |
| 7,427,394 B2 | 9/2008 | Anderson et al. |
| 7,507,859 B2 | 3/2009 | Grinstaff et al. |
| 7,556,684 B2 | 7/2009 | Bury et al. |
| 7,745,651 B2 | 6/2010 | Heyes et al. |
| 7,799,565 B2 | 9/2010 | MacLachlan et al. |
| 7,803,397 B2 | 9/2010 | Heyes et al. |
| 7,901,708 B2 | 3/2011 | MacLachlan et al. |
| 7,972,435 B2 | 7/2011 | Bury et al. |
| 8,071,082 B2 | 12/2011 | Zugates et al. |
| 8,093,367 B2 | 1/2012 | Kore et al. |
| 8,101,741 B2 | 1/2012 | MacLachlan et al. |
| 8,188,263 B2 | 5/2012 | MacLachlan et al. |
| RE43,612 E | 8/2012 | Anderson et al. |
| 8,236,943 B2 | 8/2012 | Lee et al. |
| 8,278,036 B2 | 10/2012 | Kariko et al. |
| 8,287,849 B2 | 10/2012 | Langer et al. |
| 8,304,529 B2 | 11/2012 | Kore et al. |
| 8,329,070 B2 | 12/2012 | MacLachlan et al. |
| 8,450,298 B2 | 5/2013 | Mahon et al. |
| 8,513,403 B2 | 8/2013 | MacLachlan et al. |
| 8,557,231 B2 | 10/2013 | Langer et al. |
| 8,562,966 B2 | 10/2013 | Zugates et al. |
| 8,569,256 B2 | 10/2013 | Heyes et al. |
| 8,710,200 B2 | 4/2014 | Schrum et al. |
| 8,808,681 B2 | 8/2014 | Anderson et al. |
| 8,822,663 B2 | 9/2014 | Schrum et al. |
| 8,853,377 B2 | 11/2014 | Guild et al. |
| 8,883,202 B2 | 11/2014 | Manoharan et al. |
| 8,936,942 B2 | 1/2015 | Heyes et al. |
| 8,969,353 B2 | 3/2015 | Mahon et al. |
| 8,980,864 B2 | 3/2015 | Hoge et al. |
| 8,999,351 B2 | 4/2015 | Manoharan et al. |
| 8,999,950 B2 | 4/2015 | MacLachlan et al. |
| 9,006,487 B2 | 4/2015 | Anderson et al. |
| 9,018,187 B2 | 4/2015 | Heyes et al. |

(56) References Cited

U.S. PATENT DOCUMENTS

| | | |
|---|---|---|
| 9,051,567 B2 | 6/2015 | Fitzgerald et al. |
| 9,061,059 B2 | 6/2015 | Chakraborty et al. |
| 9,074,208 B2 | 7/2015 | MacLachlan et al. |
| 9,089,604 B2 | 7/2015 | Chakraborty et al. |
| 9,095,552 B2 | 8/2015 | Chakraborty et al. |
| 9,101,666 B2 | 8/2015 | Langer et al. |
| 9,107,886 B2 | 8/2015 | Chakraborty et al. |
| 9,114,113 B2 | 8/2015 | Chakraborty et al. |
| 9,181,319 B2 | 11/2015 | Schrum et al. |
| 9,186,325 B2 | 11/2015 | Manoharan et al. |
| 9,186,372 B2 | 11/2015 | de Fougerolles et al. |
| 9,187,748 B2 | 11/2015 | Geisbert et al. |
| 9,192,651 B2 | 11/2015 | Chakraborty et al. |
| 9,193,827 B2 | 11/2015 | Ma et al. |
| 9,220,755 B2 | 12/2015 | Chakraborty et al. |
| 9,220,792 B2 | 12/2015 | Chakraborty et al. |
| 9,227,197 B2 | 1/2016 | Anderson et al. |
| 9,233,141 B2 | 1/2016 | Chakraborty et al. |
| 9,238,716 B2 | 1/2016 | Dahlman et al. |
| 9,254,311 B2 | 2/2016 | Bancel et al. |
| 9,295,689 B2 | 3/2016 | de Fougerolles et al. |
| 9,301,993 B2 | 4/2016 | Chakraborty et al. |
| 9,303,079 B2 | 4/2016 | Chakraborty et al. |
| 9,308,281 B2 | 4/2016 | Guild et al. |
| 9,315,472 B2 | 4/2016 | Dong et al. |
| 9,334,328 B2 | 5/2016 | Schrum et al. |
| 9,345,780 B2 | 5/2016 | Manoharan et al. |
| 9,352,042 B2 | 5/2016 | Heyes et al. |
| 9,352,048 B2 | 5/2016 | Manoharan et al. |
| 9,364,435 B2 | 6/2016 | Yaworski et al. |
| 2002/0022721 A1 | 2/2002 | Trulson et al. |
| 2002/0094528 A1 | 7/2002 | Salafsky |
| 2002/0192651 A1 | 12/2002 | Wheeler et al. |
| 2002/0192721 A1 | 12/2002 | Rizzuto et al. |
| 2002/0193622 A1 | 12/2002 | Watanabe et al. |
| 2003/0082154 A1 | 5/2003 | Leamon |
| 2003/0181410 A1 | 9/2003 | Wheeler et al. |
| 2003/0215395 A1 | 11/2003 | Yu et al. |
| 2004/0142025 A1 | 7/2004 | MacLachlan et al. |
| 2004/0181077 A1 | 9/2004 | Raymond et al. |
| 2004/0235982 A1 | 11/2004 | Rabasco et al. |
| 2005/0059005 A1 | 3/2005 | Tuschl et al. |
| 2005/0069590 A1 | 3/2005 | Buehler et al. |
| 2005/0143332 A1 | 6/2005 | Monahan et al. |
| 2005/0148786 A1 | 7/2005 | Ikeda et al. |
| 2005/0244961 A1 | 11/2005 | Short et al. |
| 2006/0008910 A1 | 1/2006 | MacLachlan et al. |
| 2006/0069225 A1 | 3/2006 | Wintermantel et al. |
| 2006/0083780 A1 | 4/2006 | Heyes et al. |
| 2006/0223939 A1 | 10/2006 | Lange et al. |
| 2006/0228404 A1 | 10/2006 | Anderson et al. |
| 2007/0059373 A1 | 3/2007 | Oberg |
| 2007/0135372 A1 | 6/2007 | MacLachlan et al. |
| 2007/0185128 A1 | 8/2007 | Conde-Frieboes et al. |
| 2007/0196503 A1 | 8/2007 | Wilson et al. |
| 2007/0275923 A1 | 11/2007 | Chen et al. |
| 2008/0145338 A1 | 6/2008 | Anderson et al. |
| 2008/0242626 A1 | 10/2008 | Zugates et al. |
| 2009/0023673 A1 | 1/2009 | Manoharan et al. |
| 2009/0221684 A1 | 9/2009 | Grinstaff et al. |
| 2009/0263407 A1 | 10/2009 | Dande et al. |
| 2009/0270481 A1 | 10/2009 | MacLachlan et al. |
| 2010/0036084 A1 | 2/2010 | Langer et al. |
| 2010/0041152 A1 | 2/2010 | Wheeler et al. |
| 2010/0178699 A1 | 7/2010 | Gao et al. |
| 2010/0240072 A1 | 9/2010 | Wester et al. |
| 2010/0331234 A1 | 12/2010 | Mahon et al. |
| 2011/0009641 A1 | 1/2011 | Anderson et al. |
| 2011/0092739 A1 | 4/2011 | Chen et al. |
| 2011/0158935 A1 | 6/2011 | Kraft |
| 2011/0200582 A1 | 8/2011 | Baryza et al. |
| 2011/0256175 A1 | 10/2011 | Hope et al. |
| 2011/0293703 A1 | 12/2011 | Mahon et al. |
| 2011/0311583 A1 | 12/2011 | Manoharan et al. |
| 2012/0009222 A1 | 1/2012 | Nguyen et al. |
| 2012/0065252 A1 | 3/2012 | Schrum et al. |
| 2012/0065358 A1 | 3/2012 | Langer et al. |
| 2012/0128760 A1 | 5/2012 | Manoharan et al. |
| 2012/0142756 A1 | 6/2012 | Guild et al. |
| 2012/0195936 A1 | 8/2012 | Rudolph et al. |
| 2012/0196923 A1 | 8/2012 | Rege et al. |
| 2012/0202871 A1 | 8/2012 | Heyes et al. |
| 2012/0237975 A1 | 9/2012 | Schrum et al. |
| 2012/0251560 A1 | 10/2012 | Dahlman et al. |
| 2012/0251618 A1 | 10/2012 | Schrum et al. |
| 2012/0328668 A1 | 12/2012 | MacLachlan et al. |
| 2013/0158021 A1 | 6/2013 | Dong et al. |
| 2013/0195967 A1 | 8/2013 | Guild et al. |
| 2013/0237594 A1 | 9/2013 | de Fougerolles et al. |
| 2013/0259923 A1 | 10/2013 | Bancel et al. |
| 2013/0259924 A1 | 10/2013 | Bancel et al. |
| 2013/0266640 A1 | 10/2013 | de Fougerolles et al. |
| 2013/0302401 A1 | 11/2013 | Ma et al. |
| 2014/0010861 A1 | 1/2014 | Bancel et al. |
| 2014/0044772 A1 | 2/2014 | MacLachlan et al. |
| 2014/0094399 A1 | 4/2014 | Langer et al. |
| 2014/0105964 A1 | 4/2014 | Bancel et al. |
| 2014/0105965 A1 | 4/2014 | Bancel et al. |
| 2014/0147432 A1 | 5/2014 | Bancel et al. |
| 2014/0147454 A1 | 5/2014 | Chakraborty et al. |
| 2014/0148502 A1 | 5/2014 | Bancel et al. |
| 2014/0155472 A1 | 6/2014 | Bancel et al. |
| 2014/0155473 A1 | 6/2014 | Bancel et al. |
| 2014/0155474 A1 | 6/2014 | Bancel et al. |
| 2014/0155475 A1 | 6/2014 | Bancel et al. |
| 2014/0161830 A1 | 6/2014 | Anderson et al. |
| 2014/0171485 A1 | 6/2014 | Bancel et al. |
| 2014/0179756 A1 | 6/2014 | MacLachlan et al. |
| 2014/0179771 A1 | 6/2014 | Bancel et al. |
| 2014/0186432 A1 | 7/2014 | Bancel et al. |
| 2014/0193482 A1 | 7/2014 | Bancel et al. |
| 2014/0194494 A1 | 7/2014 | Bancel et al. |
| 2014/0199371 A1 | 7/2014 | Bancel et al. |
| 2014/0200261 A1 | 7/2014 | Hoge et al. |
| 2014/0200262 A1 | 7/2014 | Bancel et al. |
| 2014/0200263 A1 | 7/2014 | Bancel et al. |
| 2014/0200264 A1 | 7/2014 | Bancel et al. |
| 2014/0206752 A1 | 7/2014 | Afeyan et al. |
| 2014/0206753 A1 | 7/2014 | Guild et al. |
| 2014/0206755 A1 | 7/2014 | Bancel et al. |
| 2014/0206852 A1 | 7/2014 | Hoge et al. |
| 2014/0221465 A1 | 8/2014 | Bancel et al. |
| 2014/0243399 A1 | 8/2014 | Schrum et al. |
| 2014/0249208 A1 | 9/2014 | Bancel et al. |
| 2014/0255467 A1 | 9/2014 | Bancel et al. |
| 2014/0255468 A1 | 9/2014 | Bancel et al. |
| 2014/0275227 A1 | 9/2014 | Hoge et al. |
| 2014/0275229 A1 | 9/2014 | Bancel et al. |
| 2014/0288160 A1 | 9/2014 | Guild et al. |
| 2014/0294937 A1 | 10/2014 | MacLachlan et al. |
| 2014/0329884 A1 | 11/2014 | Dong et al. |
| 2014/0343129 A1 | 11/2014 | de Fougerolles et al. |
| 2015/0005372 A1 | 1/2015 | Hoge et al. |
| 2015/0017211 A1 | 1/2015 | de Fougerolles et al. |
| 2015/0044277 A1 | 2/2015 | Bancel et al. |
| 2015/0050354 A1 | 2/2015 | Bouchon et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064242 A1 | 3/2015 | Heyes et al. |
| 2015/0064725 A1 | 3/2015 | Schrum et al. |
| 2015/0086614 A1 | 3/2015 | Bancel et al. |
| 2015/0111248 A1 | 4/2015 | Bancel et al. |
| 2015/0111945 A1 | 4/2015 | Geisbert et al. |
| 2015/0166465 A1 | 6/2015 | Chen et al. |
| 2015/0190515 A1 | 7/2015 | Manoharan et al. |
| 2015/0203439 A1 | 7/2015 | Mahon et al. |
| 2015/0265708 A1 | 9/2015 | Manoharan et al. |
| 2015/0315541 A1 | 11/2015 | Bancel et al. |
| 2015/0315584 A1 | 11/2015 | MacDonald et al. |
| 2015/0366997 A1 | 12/2015 | Guild et al. |
| 2016/0009657 A1 | 1/2016 | Anderson et al. |
| 2016/0022821 A1 | 1/2016 | Langer et al. |

(56) References Cited

U.S. PATENT DOCUMENTS

| | | |
|---|---|---|
| 2016/0095924 A1 | 4/2016 | Hope et al. |
| 2016/0114011 A1 | 4/2016 | Bancel et al. |
| 2016/0114042 A1 | 4/2016 | Anderson et al. |
| 2016/0115477 A1 | 4/2016 | MacLachlan et al. |
| 2016/0115483 A1 | 4/2016 | MacLachlan et al. |
| 2016/0136236 A1 | 5/2016 | Hoge et al. |
| 2016/0137785 A1 | 5/2016 | Ma et al. |
| 2016/0151284 A1 | 6/2016 | Heyes et al. |
| 2016/0158385 A1 | 6/2016 | Bancel et al. |
| 2016/0193299 A1 | 7/2016 | de Fougerolles et al. |
| 2016/0194368 A1 | 7/2016 | Hoge et al. |
| 2016/0194625 A1 | 7/2016 | Hoge et al. |
| 2016/0213785 A1 | 7/2016 | Monoharan et al. |
| 2016/0237108 A1 | 8/2016 | Fraley et al. |
| 2016/0237134 A1 | 8/2016 | Hoge et al. |
| 2018/0161451 A1 | 6/2018 | Fotin-Mleczek et al. |

FOREIGN PATENT DOCUMENTS

| | | |
|---|---|---|
| CA | 2807 552 | 9/2012 |
| CN | 1399561 | 2/2003 |
| CN | 101506196 | 8/2009 |
| CN | 100569877 C | 12/2009 |
| CN | 101863544 A | 10/2010 |
| DE | 24 30 998 A1 | 1/1975 |
| DE | 25 20 814 A1 | 11/1976 |
| DE | 3728917 A1 | 3/1989 |
| EP | 0 211 305 A2 | 2/1987 |
| EP | 6 73 637 A1 | 9/1995 |
| EP | 0959092 A1 | 11/1999 |
| EP | 1 277 829 A2 | 1/2003 |
| EP | 2045251 A1 | 4/2009 |
| EP | 1519 714 | 10/2010 |
| EP | 2338520 A1 | 6/2011 |
| EP | 2449 106 | 5/2012 |
| EP | 2532649 A1 | 12/2012 |
| EP | 2338 478 | 6/2013 |
| EP | 2823 809 | 1/2015 |
| FR | 1 378 382 A | 11/1964 |
| FR | 2 235 112 A1 | 1/1975 |
| GB | 1072118 A | 6/1967 |
| GB | 1602085 A | 11/1981 |
| JP | H07-053535 | 2/1955 |
| JP | S48-022365 | 3/1973 |
| JP | S49-127908 | 12/1974 |
| JP | S51-023537 | 2/1976 |
| JP | 51-125144 | 11/1976 |
| JP | S52-010847 | 1/1977 |
| JP | S63125144 A | 5/1988 |
| JP | 63-154788 | 6/1988 |
| JP | H06-200073 A | 7/1994 |
| JP | H06-211978 A | 8/1994 |
| JP | H09-505593 A | 6/1997 |
| JP | H10-197978 A | 7/1998 |
| JP | 11-005786 A | 1/1999 |
| JP | 11-080142 | 3/1999 |
| JP | 2001-523215 A | 11/2001 |
| JP | 2002-167368 A | 6/2002 |
| JP | 2003-519199 | 6/2003 |
| JP | 4-108173 B2 | 6/2008 |
| JP | 2008-247749 A | 10/2008 |
| JP | 50-24216 B2 | 9/2012 |
| JP | 2014172827 | 9/2014 |
| WO | WO-1993/18229 A1 | 9/1993 |
| WO | WO-1993/18754 A1 | 9/1993 |
| WO | WO-1995/11004 A1 | 4/1995 |
| WO | WO-1995/14651 A1 | 6/1995 |
| WO | WO-1996/26179 A1 | 8/1996 |
| WO | WO-1996/36314 | 11/1996 |
| WO | WO-1997/23457 | 7/1997 |
| WO | WO-1998/16202 A2 | 4/1998 |
| WO | WO 1998053801 A | 12/1998 |
| WO | WO-2000/03044 | 1/2000 |
| WO | WO-2000/64484 A2 | 11/2000 |
| WO | WO-2001/05375 A1 | 1/2001 |
| WO | WO 2001074333 A1 | 10/2001 |
| WO | WO-2002/00870 A2 | 1/2002 |
| WO | WO-2002/22709 A1 | 3/2002 |
| WO | WO-2002/31025 A2 | 4/2002 |
| WO | WO-2003/040288 | 5/2003 |
| WO | WO-2003/070735 A2 | 8/2003 |
| WO | WO-2004/043588 A2 | 5/2004 |
| WO | WO-2004/048345 A2 | 6/2004 |
| WO | WO-2004/106411 A2 | 12/2004 |
| WO | WO-2005/026372 | 3/2005 |
| WO | WO-2005/028619 A2 | 3/2005 |
| WO | WO-2005/121348 A1 | 12/2005 |
| WO | WO-2006/065266 A2 | 6/2006 |
| WO | WO-2006/082088 A1 | 8/2006 |
| WO | WO-2006/105043 A2 | 10/2006 |
| WO | WO-2009/127060 | 10/2006 |
| WO | WO-2006/138380 A2 | 12/2006 |
| WO | WO-2007/031091 A2 | 3/2007 |
| WO | WO-2007/096662 A2 | 8/2007 |
| WO | WO-2007/143659 A2 | 12/2007 |
| WO | WO-2008/011561 A2 | 1/2008 |
| WO | WO-2008/113364 A2 | 9/2008 |
| WO | WO-2009/046220 A2 | 4/2009 |
| WO | WO-2009/127230 A1 | 10/2009 |
| WO | WO-2010/037408 A1 | 4/2010 |
| WO | WO-2010/042877 A1 | 4/2010 |
| WO | WO-2010/045512 A2 | 4/2010 |
| WO | WO-2010/053572 A2 | 5/2010 |
| WO | WO-2010/099387 A1 | 9/2010 |
| WO | WO-2010/114789 A1 | 10/2010 |
| WO | WO-2010/129709 A1 | 11/2010 |
| WO | WO-2011/012316 A2 | 2/2011 |
| WO | WO-2011/012746 A2 | 2/2011 |
| WO | WO-2011/039144 A1 | 4/2011 |
| WO | WO-2011/068810 A1 | 6/2011 |
| WO | WO-2011/141705 A1 | 11/2011 |
| WO | WO-2012/019168 | 2/2012 |
| WO | WO-2012/027675 A2 | 3/2012 |
| WO | WO-2012/133737 A1 | 10/2012 |
| WO | WO-2012/135025 A2 | 10/2012 |
| WO | WO-2012/135805 | 10/2012 |
| WO | WO-2012/170889 A1 | 12/2012 |
| WO | WO-2012/170930 A1 | 12/2012 |
| WO | WO-2013/039857 | 3/2013 |
| WO | WO-2013/039861 | 3/2013 |
| WO | WO-2013/063468 A1 | 5/2013 |
| WO | WO-2013/090186 | 6/2013 |
| WO | WO-2013/101690 | 7/2013 |
| WO | WO-2013/126803 | 8/2013 |
| WO | WO-2013/130161 A1 | 9/2013 |
| WO | WO-2013/151663 A1 | 10/2013 |
| WO | WO-2013/151664 A1 | 10/2013 |
| WO | WO-2013/151666 A2 | 10/2013 |
| WO | WO-2013/151667 A1 | 10/2013 |
| WO | WO-2013/151668 A2 | 10/2013 |
| WO | WO-2013/151670 A2 | 10/2013 |
| WO | WO-2013/151671 A1 | 10/2013 |
| WO | WO-2013/151672 A2 | 10/2013 |
| WO | WO-2013/151736 A2 | 10/2013 |
| WO | WO-2014/028487 A1 | 2/2014 |
| WO | WO-2014/113089 A2 | 7/2014 |
| WO | WO-2014/144039 | 9/2014 |
| WO | WO-2014/144711 | 9/2014 |
| WO | WO-2014/144767 | 9/2014 |
| WO | WO-2014/152027 | 9/2014 |
| WO | WO-2014/152030 | 9/2014 |
| WO | WO-2014/152031 | 9/2014 |
| WO | WO-2014/152211 | 9/2014 |
| WO | WO-2014/152540 | 9/2014 |
| WO | WO-2014/158795 | 10/2014 |
| WO | WO-2014/159813 | 10/2014 |
| WO | WO-2014/179562 A1 | 11/2014 |
| WO | WO-2014/210356 A1 | 12/2014 |
| WO | WO-2015/006747 A2 | 1/2015 |
| WO | WO-2015/048744 A2 | 4/2015 |
| WO | WO-2015/051169 A2 | 4/2015 |
| WO | WO-2015/051173 A2 | 4/2015 |
| WO | WO-2015/058069 A1 | 4/2015 |
| WO | WO-2015/011633 | 1/2016 |

(56) References Cited

FOREIGN PATENT DOCUMENTS

| WO | WO-2016/054421 | 4/2016 |
|---|---|---|
| WO | WO-2016/071857 | 5/2016 |
| WO | WO-2016/077123 | 5/2016 |
| WO | WO-2016/077125 | 5/2016 |
| WO | WO-2016/118724 | 7/2016 |
| WO | WO-2016/118725 | 7/2016 |

OTHER PUBLICATIONS

U.S. Appl. No. 61/494,745.
U.S. Appl. No. 61/494,881.
U.S. Appl. No. 61/494,882.
Adami, R.C. et al., An amino acid-based amphoteric liposomal delivery system for systemic administration of siRNA. Molecular Therapy 19(6):1141-1151 (2011).
Akinc et al., Parallel synthesis and biophysical characterization of a degradable polymer library for gene delivery. J Am Chem Soc. May 7, 2003;125(18):5316-23.
Akinc, A. et al., A combinatorial library of lipid-like materials for delivery of RNAi therapeutics. Nature Biotechnology 26(5):561-569 (2008).
Akinc, A. et al., Development of lipidoid-siRNA formulations for systemic delivery to the liver. Molecular Therapy 17(5):872-879 (2009).
Anderson, D.G. et al., Structure/property studies of polymeric gene delivery using a library of poly(beta-amino esters). Molecular Therapy 11(3):426-434 (2005).
Anderson, J. Biological Responses to Materials. Annual Review of Materials Research 31:81-110 (2001).
Anderson, W. French, Human gene therapy, Nature, 392, 25-30 (1998).
Asokan et al., Cytosolic delivery of macromolecules. 3. Synthesis and characterization of acid-sensitive bis-detergents. Bioconjug Chem. Nov.-Dec. 2004;15(6):1166-73.
Bajaj, A. et al., Synthesis and gene transfection efficacies of PEI-cholesterol-based lipopolymers. Bioconjugate Chemistry 19(8):1640-516511 (2008).
Behr, J.P. et al., Efficient gene transfer into mammalian primary endocrine cells with lipopolyamine-coated DNA, Proceedings of the National Academy of Sciences USA, 86(18):6982-6986 (1989).
Bloomfield, VA, Quasi-elastic light scattering applications in biochemistry and biology, Annual Review of Biophysics and Bioengineering, 10:421-450 (1981).
Bourque et al., Hydroformylation Reactions Using Recyclable Rhodium-Complexed Dendrimers on Silica. J Am Chem Soc. 2000;122(5):956-957.
Boussif, O. et al., A versatile vector for gene and oligonucleotide transfer into cells in culture and in vivo: polyethylenimine. Proceedings of the National Academy of Sciences of the USA. 92(16):7297-7301 (1995).
Braun, C.S. et al., Structure/function relationships of polyamidoamine/DNA dendrimers as gene delivery vehicles. Journal of Pharmaceutical Sciences 94(2):423-436 (2005).
Breunig, M. et al., Breaking up the correlation between efficacy and toxicity for nonviral gene delivery. Proceedings of the National Academy of Sciences of the U S A. 104(36):14454-14459 (2007).
Breunig, M. et al., Mechanistic investigation of poly(ethylene imine)-based siRNA delivery: disulfide bonds boost intracellular release of the cargo. Journal of Controlled Release 130(1):57-63 (2008).
Brey, D.M. et al., Controlling poly(beta-amino ester) network properties through macromer branching. Acta Biomaterialia 4(2):207-217 (2008).
Brey, D.M. et al., Influence of macromer molecular weight and chemistry on poly(beta-amino ester) network properties and initial cell interactions. Journal of Biomedical Materials Research Part A 85(3):731-741 (2007).

Budker, V. et al., Protein/Amphipathic Polyamine Complexes Enable Highly Efficient Transfection with Minimal Toxicity, BioTechniques, 23:139-147 (1997).
Burnett, J.C. et al., Current progress of siRNA/shRNA therapeutics in clinical trials. Biotechnology Journal 6(9):1130-1146 (2011).
Byk, G. et al., Synthesis, activity, and structure—activity relationship studies of novel cationic lipids for DNA transfer. Journal of Medical Chemistry 41(2):224-235 (1998).
Caplen, N.J. et al., In vitro liposome-mediated DNA transfection of epithelial cell lines using the cationic liposome DC-Chol/DOPE, Gene Therapy, 2:603-613 (1995).
Castanotto, D. et al., The promises and pitfalls of RNA-interference-based therapeutics. Nature 457(7228):426-433 (2009).
Chakraborty, C. Potentiality of Small Interfering RNAs (siRNA) as Recent Therapeutic Targets for Gene-Silencing. Current Drug Targets 8(3):469-82 (2007).
Chau, Y. et al., Investigation of targeting mechanism of new dextran-peptide-methotrexate conjugates using biodistribution study in matrix-metalloproteinase-overexpressing tumor xenograft model, J. Pharm. Sci., 95(3): 542-551 (2006).
Chen, D. et al., Rapid discovery of potent siRNA-containing lipid nanoparticles enabled by controlled microfluidic formulation. Journal of the American Chemical Society 134(16):6948-6951 (2012).
Chen, Y. and Huang, L., Tumor-targeted delivery of siRNA by non-viral vector: safe and effective cancer therapy. Expert Opinion on Drug Delivery 5(12):1301-1311 (2008).
Chiang et al., Synthesis, characterization and properties of novel self-extinguishing organic- inorganic nanocomposites containing nitrogen, silicon and phosphorus via sol-gel method. Composite Science and Technology. 2008;68(14):2849-57.
Christensen, U.B. et al., Intercalating nucleic acids containing insertions of 1-O-(1-pyrenylmethyl)glycerol: stabilisation of dsDNA and discrimination of DNA over RNA, Nucl. Acids. Res., 30(22): 4918-4925 (2002).
Cotton, M. et al., Receptor-mediated transport of DNA into eukaryotic cells. Methods in Enzymology 217 (H):618-644 (1993).
Creusat, G. et al., Proton sponge trick for pH-sensitive disassembly of polyethylenimine-based siRNA delivery systems. Bioconjugate Chemistry 21(5):994-1002 (2010).
Crooke, S.T. Molecular mechanisms of action of antisense drugs. Biochimica et Biophysica Acta 1489(1):31-44. Review (1999).
Crystal, R.G. Transfer of genes to humans: early lessons and obstacles to success. Science 270(5235):404-410. Review (1995).
Damen, M. et al., Delivery of DNA and siRNA by novel gemini-like amphiphilic peptides. Journal of Controlled Release 145(1):33-39 (2010).
Davis, M. E., The first targeted delivery of siRNA in humans via a self-assembling, cyclodextrin polymer-based nanoparticle: from concept to clinic. Molecular Pharmacuetics 6(3):659-668 (2009).
Davis, M.E. et al., Evidence of RNAi in humans from systemically administered siRNA via targeted nanoparticles. Nature 464(7291):1067-1070 (2010).
Decher, G. Fuzzy Nanoassemblies: Toward Layered Polymeric Mullicomposites. Science 277: 1232-1237 (1997).
Denardo, S.J. et al., Enhanced Therapeutic Index of Radioimmunotherapy (RIT) in Prostate Cancer Patients Comparison of Radiation Dosimetry for 1,4,7,10-Tetraazacyclociodecane-N,N',N'',N'''-Tetraacetic Acid (DOTA)-Peptide versus 2IT-DOTA Monoclonal Antibody Linkage for RIT1, Clin. Cancer Res., 9: 3665s (2003).
Dern, R.J. et al., Toxicity studies of pyrimethamine (daraprim). The American Journal of Tropical Medicine and Hygiene 4(2):217-220 (1955).
Deshmukh, H. M and Huang, L., Liposome and polylysine mediated gene therapy. New Journal of Chemistry 21:113-124 (1997).
Discher, B.M. et al., Polymersomes: tough vesicles made from diblock copolymers. Science 284(5417):1143-1146 (1999).
Discher, D.E. and Eisenberg, A., Polymer vesicles. Science 297(5583):967-973. Review (2002).
Dong, Y. et al., Lipopeptide nanoparticles for potent and selective siRNA delivery in rodents and nonhuman primates, Proceedings of the National Academy of Sciences, 111(11): 3955-3960 (2014).
Elbashir, S.M. et al., RNA interference is mediated by 21- and 22-nucleotide RNAs. Genes & Development 15: 188-200 (2001).

(56) References Cited

OTHER PUBLICATIONS

Ewert, K. et al., Cationic lipid-DNA complexes for gene therapy: understanding the relationship between complex structure and gene delivery pathways at the molecular level. Current Medicinal Chemistry 11(2): 133-149 (2004).
Fechter, P. and Brownlee, G.G., Recognition of mRNA cap structures by viral and cellular proteins, Journal of General Virology, 86(Pt 5):1239-1249 (2005).
Felgner, P.L. et al., Lipofection: a highly efficient, lipid-mediated DNA-transfection procedure, Proceedings of the National Academy of Sciences USA, 84(21):7413-7417 (1987).
Fenske, D.B. and Cullis, P., Liposomal nanomedicines. Expert Opinion on Drug Delivery 5(1):25-44 (2008).
Ferruti, P.F. and Barbucci, R. , Linear amino polymers: Synthesis, protonation and complex formation. Advances in Polymer Science 58:55-92 (1984).
Ferruti, P.F. et al., A novel modification of poly(l-lysine) leading to a soluble cationic polymer with reduced toxicity and with potential as a transfection agent. Macromolecular Chemistry and Physics 199:2565-2575 (1998).
Fire, A. et al., Potent and specific genetic interference by double-stranded RNA in Caenorhabditis elegans. Nature 391(6669):806-811 (1998).
Fourneau et al., Two new series of local anesthetics derived from piperazine. Bulletin de la Societe Chimique de France. 1930;47:1003-16. French.
Furgeson, D.Y. et al., Modified linear polyethylenimine-cholesterol conjugates for DNA complexation. Bioconjugate Chemistry 14(4):840-847 (2003).
Furgeson, D.Y. et al., Novel water insoluble lipoparticulates for gene delivery. Pharmaceutical Research 19(4): 382-390 (2002).
Gao, X. and Huang, L., A novel cationic liposome reagent for efficient transfection of mammalian cells, Biochemical and Biophysical Research Communications, 179(1):280-285 (1991).
Giuliani et al., Beyond natural antimicrobial peptides: multimeric peptides and other peptidomimetic approaches. Cell Mol Life Sci. Jul. 1, 2011;68(13):2255-66. doi: 10.1007/s00018-01 1-0717-3. Epub May 20, 2011.
Godbey, W.T. et al., Size matters: molecular weight affects the efficiency of poly(ethylenimine) as a gene delivery vehicle. Journal of Biomedical Materials Research 45(3):268-275 (1998).
Gonzalez, H. et al., New class of polymers for the delivery of macromolecular therapeutics. Bioconjugate Chemistry 10(6):1068-1074 (1999).
Grayson, A.C.R. et al., Biophysical and structural characterization of polyethylenimine-mediated siRNA delivery in vitro. Pharmaceutical Research 23(8): 1868-1876 (2006).
Grudzien, E. et al., Novel cap analogs for in vitro synthesis of mRNAs with high translational efficiency, RNA, 10(9):1479-1487 (2004).
Grudzien-Nogalska, E. et al., Phosphorothioate cap analogs stabilize mRNA and increase translational efficiency in mammalian cells, RNA, 13(10):1745-1755 (2007).
Grunlan, M.A. et al., Synthesis of 1,9-bis[glycidyloxypropyl]penta(1'H, 1'H, 2'H, 2'H-perfluoroalkylmethylsiloxane)s and copolymerization with piperazine. Polymer 45:2517-2523 (2004).
Gupta, U. et al., A review of in vitro-in vivo investigations on dendrimers: the novel nanoscopic drug carriers. Nanomedicine: Nanotechnology, Biology, and Medicine 2(2):66-73 (2006).
Gust, T.C. et al., RNA-containing adenovirus/polyethylenimine transfer complexes effectively transduce dendritic cells and induce antigen-specific T cell responses, The Journal of Gene Medicine, 6(4): 464-470 (2004).
Guttman, M. et al., Chromatin signature reveals over a thousand highly conserved large non-coding RNAs in mammals, Nature, 458:223-227 (2009).
Haensler, J. and Szoka, F., Polyamidoamine casrade polymers mediate efficient transfection of cells in culture. Bioconjugate Chemistry 4(5):372-379 (1993).
Heidenreich, O. et al., High Activity and Stability of Hammerhead Ribozymes Containing 2'-Modified Pyrimidine Nucleosides and Phosphorothioates, The Journal of Biological Chemistry, 269(3):2131-2138 (1994).
Heyes, J. et al., Cationic lipid saturation influences intracellular delivery of encapsulated nucleic acids, Journal of Controlled Release, 107(2):276-287 (2005).
Hill, I.R.C. et al., In vitro cytotoxicity of poly(amidoamine)s: relevance to DNA delivery. Biochimica et Biophysica Acta 1427: 161-174 (1999).
Hill, J.G. et al., Enantioselective Epoxidation of Allylic Alcohols: (2S,3S)-3-Propyloxiranemethanol. Organic Syntheses Collection 7: 461 (1990) and 63: 66 (1985) (8 pages).
Hofland, H.E.J et al., Formation of stable cationic lipid/DNA complexes for gene transfer. Proceedings of the National Academy of Sciences of the USA 93 (14): 7305-7309 (1996).
Hope, M.J. et al., Cationic Lipids, Phosphatidylethanolamine and the Intracellular Delivery of Polymeric, Nucleic Acid-Based Drugs. Molecular Membrane Technology 15:1-14 (1998).
Hornung, V. et al., Quantitative expression of toll-like receptor 1-10 mRNA in cellular subsets of human peripheral blood mononuclear cells and sensitivity to CpG oligodeoxynucleotides. The Journal of Immunology 168:4531-4537 (2002).
Howard, K.A. Delivery of RNA interference therapeutics using polycation-based nanoparticles. Advanced Drug Delivery Reviews 61: 710-720 (2009).
Hsu et al., Diethanolamine (DEA) degradation under gas-treating conditions. Industrial and Engineering Chemistry Product Research and Development. 1985;24(4):630-35.
Huang, Z. et al., Thiocholesterol-Based Lipids for Ordered Assembly of Bioresponsive Gene Carriers, Molecular Therapy, 11(3):409-417 (2005).
Ichimaru et al., Synthesis and characterization of new piperazine-type inhibitors for mitochondrial NADH-ubiquinone oxidoreductase (complex I). Biochemistry. Oct. 7, 2008;47(40):10816-26.
Ikeda et al., Role of micafungin in the antifungal armamentarium. Curr Med Chem. 2007;14(11):1263-75.
Incani, V. et al., Lipid and hydrophobic modification of cationic carriers on route to superior gene vectors. Soft Matter 6: 2124-2138 (2010).
Jemiclity, J. et al., Novel "anti-reverse" cap analogs with superior translational properties, RNA, 9(9):1108-1122 (2003).
Jiang, G. et al., Hyaluronic acid-polyethyleneimine conjugate for target specific intracellular delivery of siRNA. Biopolymers 89 (7): 635-642 (2008).
Jiang, M. et al., Electrochemically controlled release of lipid/DNA complexes: a new tool for synthetic gene delivery system. Electrochemistry Communications (6): 576-582 (2004).
Jiang, S. and Cao, Z., Ultralow-fouling, functionalizable, and hydrolyzable zwitterionic materials and their derivatives for biological applications. Advanced Materials 22(9):920-932 (2010).
Jolck, R.I. et al., Solid-phase synthesis of PEGylated lipopeptides using click chemistry. Bioconjugate Chemistry 21(5):807-810 (2010).
Jon, S. et al., Degradable poly(amino alcohol esters) as potential DNA vectors with low cytotoxicity. Biomacromolecules 4(6):1759-1762 (2003).
Juliano et al., Biological barriers to therapy with antisense and siRNA oligonucleotides. Mol Pharm. May-Jun. 2009;6(3):686-95. doi: 10.1021/mp900093r.
Kabanov, A.V. and Kabanov, V.A., DNA complexes with polycations for the delivery of genetic material into cells. Bioconjugate Chemistry 6(1): 7-20 (1995).
Kamath, S. et al., Surface chemistry influences implant-mediated host tissue responses. Journal of Biomedical Materials Research A 86(3):617-626 (2007).
Kanetani et al., Synthesis, and physicochemical and antimicrobial properties of 3-(3-alkyl-1-piperazinyl)-1-propanesulfonic acids and some related compounds. Nippon Kagaku Kaishi.1983(12):1783-91.
Kariko, K. et al., Incorporation of Pseudouridine Into mRNA Yields Superior Nonimmunogenic Vector With Increased Translational Capacity and Biological Stability, Molecular Therapy, 16(11): 1833-1840 (2008).

(56) References Cited

OTHER PUBLICATIONS

Kaur, N. et al., A delineation of diketopiperazine self-assembly processes: understanding the molecular events involved in Nepsilon-(fumaroyl)diketopiperazine of L-Lys (FDKP) interactions. Molecular Pharmaceutics 5(2):294-315 (2007).

Kim, S.H. et al., Comparative evaluation of target-specific GFP gene silencing efficiencies for antisense ODN, synthetic siRNA, and siRNA plasmid complexed with PEI-PEG-FOL conjugate. Bioconjugate Chemistry 17(1): 241-244 (2006).

Kim, T. et al., Synthesis of biodegradable cross-linked poly(beta-amino ester) for gene delivery and its modification, inducing enhanced transfection efficiency and stepwise degradation. Bioconjugate Chemistry 16(5):1140-1148 (2005).

Klibanov, A.L. et al., Amphipathic polyethylenglycols effectively prolong the circulation time of lipsosomes, FEBS Letters, 268(1):235-237 (1990).

Kozak, M. An analysis of 5'-noncoding sequences from 699 vertebrate messenger RNAs, Nucleic Acid Research, 15(20):8125-8148 (1987).

Lasic, D.D. et al., Gelation of liposome interior. A novel method for drug encapsulation, FEBS Letters, 312(2-3):255-258 (1992).

Lee, S. et al., Stability and cellular uptake of polymerized siRNA (poly-siRNA)/polyethylenimine (PEI) complexes for efficient gene silencing. Journal of Controlled Release 141: 339-346 (2010).

Leuschner et al., Therapeutic siRNA silencing in inflammatory monocytes in mice. Nat Biotechnol. Oct. 9, 2011;29(11):1005-10. doi: 10.1038/nbt.1989.

Li, S. et al., In vivo gene transfer via intravenous administration of cationic lipid-protamine-DNA (LPD) complexes, Gene Therapy, 4:891-900 (1997).

Li, W. et al., Lipid-based Nanoparticles for Nucleic Acid Delivery, Pharmaceutical Research, 24(3):438-449 (2007).

Lim, Y. et al., A self-destroying polycationic polymer: biodegradable poly(4-hydroxy-l-proline ester). Journal of American Chemical Society 121: 5633-5639 (1999).

Lopez-Cobenas et al., Microwave-Assisted Synthesis of 2,5-Piperazinediones under Solvent-Free Conditions. Synthesis, 19: 3412-3422 (2005).

Love, K.T. et al., Lipid-like materials for low-dose in vivo gene silencing, Proceedings of the National Academy of Sciences USA, 107(5):1864-1869 (2010).

Lubke, T. et al., Proteomics of the Lysosome, Biochimica et Biophysica Acta, 1793(4):625-635 (2009).

Lukyanov, A.N. and Torchilin, V.P., Micelles from lipid derivatives of water-soluble polymers as delivery systems for poorly soluble drugs. Advanced Drug Delivery Reviews 56: 1273-1289 (2004).

Luo, D. and Saltzman, M., Synthetic DNA delivery systems. Nature Biotechnology 18: 33-37. Review (2000).

Lynn, D.M. et al., Accelerated discovery of synthetic transfection vectors: parallel synthesis and screening of a degradable polymer library. Journal of American Chemical Society 123 (33): 8155-8156 (2001).

Lynn, D.M. et al., Degradable Poly(β-amino esters): Synthesis, Characterization, and Self-Assembly with Plasmid DNA. Journal of American Chemical Society 122(44): 10761-10768 (2000).

Lynn, D.M. et al., pH-Responsive Polymer Microspheres: Rapid Release of Encapsulated Material within the Range of Intracellular pH. Angewandte Chemie International Edition 40(9): 1707-1710 (2001).

Ma, M. et al., Development of Cationic Polymer Coatings to Regulate Foreign Body Responses. Advanced Healthcare Materials 23: H189-H194. Reviews (2011).

Margus, H. et al., Cell-penetrating peptides as versatile vehicles for oligonucleotide delivery. Molecular Therapy 20 (3): 525-533 (2012).

Martell, A.E. and Chaberek, S., The Preparation and the Properties of Some N,N'-Disubstituted-ethylenediaminedipropionic Acids. Journal of the American Chemical Society 72: 5357-5361 (1950).

Mathiowitz, E. and Langer, R., Polyanhydride microspheres as drug carriers I. Hot-melt microencapsulation. Journal of Controlled Release 5:13-22 (1987).

Mathiowitz, E. et al., Novel microcapsules for delivery systems. Reactive Polymers 6: 275-283 (1987).

Mathiowitz, E. et al., Polyanhydride microspheres as drug carriers II. Microencapsulation by solvent removal. Journal of Applied Polymer Sciences 35: 755-774 (1988).

Mendelsohn, J.D. et al., Rational design of cytophilic and cytophobic polyelectrolyte multilayer thin films. Biomacromolecules 4(1): 96-106 (2003).

Miller, A. Cationic Liposomes for Gene Therapy. Angewandte Chemie International Edition 37: 1768-1785 (1998).

Mintzer et al., Nonviral vectors for gene delivery. Chem Rev. Feb. 2009;109(2):259-302.

Morrissey, D. et al., Potent and persistent in vivo anti-HBV activity of chemically modified siRNAs, Nature Biotechnology, 23(8):1002-1007 (2005).

Moure et al., Chem. Eur. J. (2001) 17:7927-7939.

Narang, A.S. et al., Cationic lipids with increased DNA binding affinity for nonviral gene transfer in dividing and nondividing cells. Bioconjugate Chemistry 16(1): 156-168 (2005).

Navarro, G. et al., Phospholipid-polyethylenimine conjugate-based micelle-like nanoparticles for siRNA delivery. Drug Delivery and Translational Research 1: 25-33 (2011).

Neamnark, A. et al., Aliphatic lipid substitution on 2 kDa polyethylenimine improves plasmid delivery and transgene expression. Molecular Pharmaceutics 6(6): 1798-1815 (2009).

Ng, J. et al., LincRNAs join the pluripotency alliance, Nature Genetics, 42:1035-1036 (2010).

Nguyen, D.N. et al., A novel high-throughput cell-based method for integrated quantification of type I interferons and in vitro screening of immunostimulatory RNA drug delivery. Biotechnology and Bioengineering 103(4): 664-675 (2009).

Nguyen, D.N. et al., Drug delivery-mediated control of RNA immunostimulation. Molecular Therapy 17(9): 1555-1562 (2009).

Nori, A. et al., Tat-conjugated synthetic macromolecules facilitate cytoplasmic drug delivery to human ovarian carcinoma cells, Bioconj. Chem., 14(1): 44-50 (2003).

Parrish, D.A. and Mathias, L.J., Five- and six-membered ring opening of pyroglutamic diketopiperazine. Journal of Organic Chemistry 67(6): 1820-1826 (2002).

Peer et al., Nanocarriers as an emerging platform for cancer therapy. Nat Nanotechnol. Dec. 2007;2(12):751-60. doi: 10.1038/nnano.2007.387.

Peppas, N.A. et al., Hydrogels in Biology and Medicine: From Molecular Principles to Bionanotechnology. Advanced Materials 18: 1345-1360 (2006).

Philipp, A. et al., Hydrophobically modified oligoethylenimines as highly efficient transfection agents for siRNA delivery. Bioconjugate Chemistry 20(11): 2055-2061 (2009).

Pons, M. et al., Liposomes obtained by the ethanol injection method, International Journal of Pharmacology, 95:51-56 (1993).

Prata, C.A. et al., Lipophilic peptides for gene delivery. Bioconjugate Chemistry 19(2): 418-420 (2008).

Putnam, D. Polymers for gene delivery across length scales. Nature Materials 5: 439-451 (2006).

Putnam, D. and Langer, R., Poly(4-hydroxy-l-proline ester): Low-Temperature Polycondensation and Plasmid DNA Complexation. Macromolecules 32(11): 3658-3662 (1999).

Ratner, B.D. and Bryant, S., Biomaterials: where we have been and where we are going. Annual Review of Biomedical Engineering 6:41-75 (2004).

Rogers et al., Biochemistry (1964), 3(12), 1850-5.

Ryng, S. et al., Synthesis and structure elucidation of 5-aminomethinimino-3-methyl-4-isoxazolecarboxylic acid phenylamides and their immunological activity. Arch. Pharm. Pharm. Med. Chem 330(11):319-26 (1997).

Sahay, G. et al., Endocytosis of nanomedicines. Journal of Controlled Release 145: 182-195 (2010).

Sakiyama-Elbert, S.E. and Hubbell, J.A., Functional Biomaterials: Design of Novel Biomaterials. Annual Review of Materials Research 31: 183-201 (2001).

Scheel et al., Therapeutic anti-tumor immunity triggered by injections of immunostimulating single-stranded RNA. Eur J Immunol. Oct. 2006;36(10):2807-16.

(56) References Cited

OTHER PUBLICATIONS

Semple, S.C. et al., Rational Design of Cationic Lipids for siRNA Delivery, Nature Biotechnology, 28(2):172-176 (2010).
Sen et al., Surfactin: biosynthesis, genetics and potential applications. Adv Exp Med Biol. 2010;672:316-23.
Shchori E., Poly(secondary Amine)s from Diacrylates and Diamines. Journal of Polymer Science 21(6):413-15 (1983).
Sherwood, R.F. Advanced drug delivery reviews: enzyme prodrug therapy, Adv. Drug Del. Rev., 22: 269-288 (1996).
Siegwart, D.J. et al., Combinatorial synthesis of chemically diverse core-shell nanoparticles for intracellular delivery. Proceedings of the National Academy of the Sciences of the USA 108(32):12996-123001 (2011).
Stern, L. et al., A novel antitumor prodrug platform designed to be cleaved by the endoprotease legumain, Bioconj. Chem., 20: 500-510 (2009).
STN-CAS database Registry No. 1067642-37-8. Entered STN-CAS database on Oct. 29, 2008.
Swali et al., Solid-Phase Dendrimer Synthesis and the Generation of Super-High-Loading Resin Beads for Combinatorial Chemistry. J Org Chem Am Chem Soc. 1997;62:4902-03.
Szoka, F. and Papahadjopoulos, D., Comparative properties and methods of preparation of lipid vesicles (liposomes). Annual Review of Biophysics Bioengineering 9: 467-508 (1980).
Tan, S. et al., Engineering Nanocarriers for siRNA Delivery. Small 7(7): 841-856 (2011).
Tang, F. and Hughes, J. et al., Introduction of a Disulfide Bond into a Cationic Lipid Enhances Transgene Expression of Plasmid DNA, Biochemical and Biophysical Research Communications, 242(1):141-145 (1998).
Tang, M.X. et al., In vitro gene delivery by degraded polyamidoamine dendrimers. Bioconjugate Chemistry 7(6): 703-714 (1996).
Tarcha, P.J. et al., Synthesis and characterization of chemically condensed oligoethylenimine containing beta-aminopropionamide linkages for siRNA delivery. Biomaterials 28: 3731-3740 (2007).
Terp et al., Differential efficacy of DOTAP enantiomers for siRNA delivery in vitro. International Journal of Pharmaceutics, 430: 328-334 (2012).
Thiel et al., Therapeutic applications of DNA and RNA aptamers. Oligonucleotides. Sep. 2009;19(3):209-22. doi: 10.1089/oli.2009.0199.
Thompson, P.E. et al., Antiamebic action of 5-chloro-7-diethylaminomethyl-8-quinolinol and of other substituted 8-quinolinols in vitro and in experimental animals. American Journal of Tropical Medicine and Hygiene 2(4): 224-248 (1955).
Toki, B.E. et al., Protease-mediated fragmentation of p-amidobenzyl ethers: a new strategy for the activation of anticancer prodrugs, J. Org. Chem., 67(6): 1866-1872 (2002).
Tranchant, I. et al., Physicochemical optimisation of plasmid delivery by cationic lipids. Journal of Gene Medicine 6: S24-S35 (2004).
Tsvetkov, D.E. et al., Neoglycoconjugates based on dendrimeric poly(aminoamides). Russian Journal of Bioorganic Chemistry 28(6): 470-486 (2002).
Urban-Klein, B. et al., RNAi-mediated gene-targeting through systemic application of polyethylenimine (PEI)-complexed siRNA in vivo. Gene Therapy 12(5): 461-466 (2005).
Van Balen, G.P. et al., Liposome/water lipophilicity: methods, information content, and pharmaceutical applications. Medicinal Research Reviews 24(3): 299-324 (2004).
Van De Wetering, P. et al., Structure-activity relationships of water-soluble cationic methacrylate/methacrylamide polymers for nonviral gene delivery. Bioconjugate Chemistry 10(4): 589-597 (1999).
Vandenbroucke, R.E. et al., Prolonged gene silencing in hepatoma cells and primary hepatocytes after small interfering RNA delivery with biodegradable poly(beta-amino esters). Journal of Gene Medicine 10: 783-794 (2008).
Veronese, F.M. et al., PEG-doxorubicin conjugates: influence of polymer structure on drug release, in vitro cytotoxicity, biodistribution, and antitumor activity, Bioconj. Chem., 16(4): 775-784 (2005).
Von Harpe et al., Characterization of commercially available and synthesized polyethylenimines for gene delivery. Journal of Controlled Release 69(2):309-322 (2000).
Walde, P. et al., Preparation of Vesicles (Liposomes). Encyclopedia of Nanoscience and Nanotechnology. Nalwa, ed. American Scientific Publishers, Los Angeles 9:43-79 (2004).
Weinstein et al., RNAi nanomedicines: challenges and opportunities within the immune system. Nanotechnology. Jun. 11, 2010;21(23):232001. doi: 10.1088/0957-4484/21/23/232001. Epub May 13, 2010.
Werth, S. et al., A low molecular weight fraction of polyethylenimine (PEI) displays increased transfection efficiency of DNA and siRNA in fresh or lyophilized complexes. Journal of Controlled Release 112: 257-270 (2006).
Wetzer, B. et al., Reducible cationic lipids for gene transfer, Biochem. J., 356:747-756 (2001).
White, J.E. et al., Poly(hydroxyaminoethers): A New Family of Epoxy-Based Thermoplastics. Advanced Materials 12(23): 1791-1800 (2000).
White, J.E. et al., Step-growth polymerization of 10,11-epoxyundecanoic acid. Synthesis and properties of a new hydroxy-functionalized thermopastic polyester. Advanced Materials 48: 3990-3998 (2007).
Whitehead, K.A. et al., Knocking down barriers: advances in siRNA delivery. Nature Reviews Drug Discovery 8(2): 129-139 (2009).
Wu, J. et al., Cationic lipid polymerization as a novel approach for constructing new DNA delivery agents. Bioconjugate Chemistry 12(2): 251-257 (2001).
Yokoe, H. and Meyer, T., Spatial Dynamics of GFP-tagged proteins investigated by local fluorescence enhancement, Nature Biotechnology, 14(10):1252-1256 (1996).
Yoneda et al., A cell-penetrating peptidic GRP78 ligand for tumor cell-specific prodrug therapy, Bioorg. Med. Chern. Lett., 18(5): 1632-1636 (2008).
Yoshioka, Y. and Calvert, P., Epoxy-based Electroactive Polymer Gels. Experimental Mechanics 42(4): 404-408 (2002).
Zagridullin, P.H. et al., Monobasic amines. II. Cycloalkylation and hydroxyalkylation of cyclic and acyclic di- and polyamines. Journal of Organic Chemistry 26(1):184-88. Russian (1990).
Zamora et al., RNA interference therapy in lung transplant patients infected with respiratory syncytial virus. Am J Respir Crit Care Med. Feb. 15, 2011;183(4):531-8. doi: 10.1164/rccm.201003-04220C. Epub Sep. 17, 2010.
Zaugg, H.E. et al., 3-Carboxy-2,5-piperazinedione and Derivatives. Journal of American Chemical Society 78(11):2626-2631 (1956).
Zauner, W.et al., Polylysine-based transfection systems utilizing receptor-mediated delivery. Advanced Drug Delivery Reviews 30(1-3):97-113(1998).
Zintchenko, A. et al., Simple modifications of branched PEI lead to highly efficient siRNA carriers with low toxicity. Bioconjugate Chemistry 19(7):1448-1455 (2008).

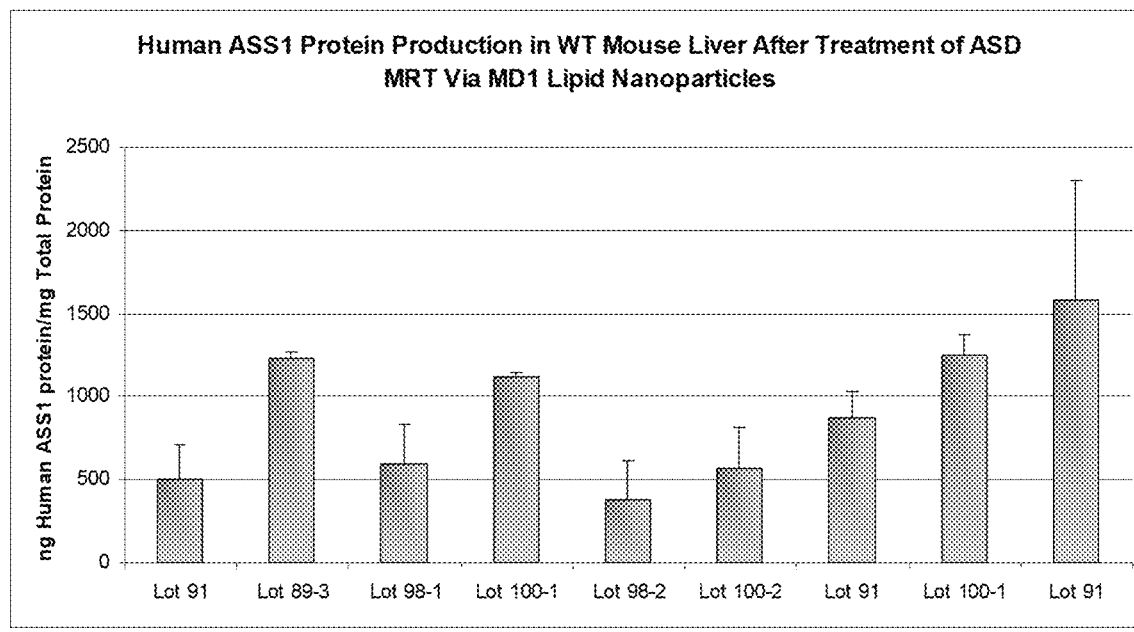

STEREOCHEMICALLY ENRICHED COMPOSITIONS FOR DELIVERY OF NUCLEIC ACIDS

RELATED APPLICATIONS

This application is a continuation of U.S. application Ser. No. 14/749,027, filed Jun. 24, 2015, which claims the benefit of U.S. Provisional Application No. 62/016,512, filed on Jun. 24, 2014, the disclosures of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Aug. 24, 2015, is named MRT_1154US2_Sequence_Listing.txt and is 5,563 bytes in size.

BACKGROUND

Delivery of nucleic acids using lipids has been explored extensively for treatment of various diseases. There remains a great need for lipids and/or lipids compositions that can deliver nucleic acids, such as short interfering RNA (siRNA) and messenger RNA (mRNA) with high efficiency and low toxicity.

SUMMARY

Among other things, the present invention provides compositions comprising stereochemically enriched lipids for delivering mRNA. The invention is based, in part, on the surprising discovery that compositions comprising stereochemically enriched lipid of formula I, below, are highly effective and have unexpectedly low toxicity in delivering mRNA and producing encoded protein in vivo:

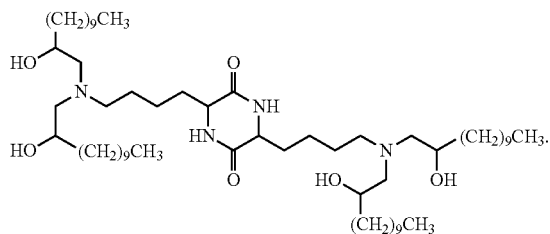

I

The present inventors found that when used for mRNA delivery, stereochemically enriched compositions of I have surprisingly low toxicity compared to stereochemically non-enriched, or stereochemically less enriched, compositions of the same lipid, as evidenced, for example, by the dramatically lower alanine aminotransferase (ALT) and aspartate aminotransferase (AST) expression levels. See Table 1.

In some embodiments, the present invention provides a composition comprising one or more chemical entities of formula I, each of which is a compound of formula I:

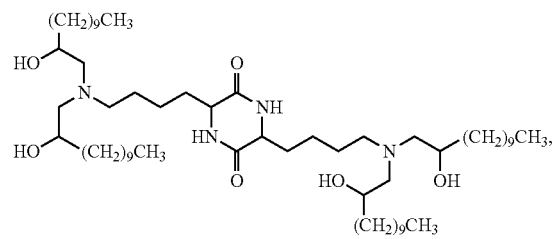

I a pharmaceutically acceptable salt thereof, a solvate thereof, or a solvate of a pharmaceutically acceptable salt thereof, the composition characterized in that greater than or equal to a first threshold amount of the total amount of chemical entities of formula I in the composition are chemical entities of formula I.a, I.b.1, I.b.2, I.c, I.d, I.e, I.f, I.g, or I.h, each of which is independently as defined and described below.

In some embodiments, the present invention provides a composition comprising one or more chemical entities of formula I, each of which is a compound of formula I:

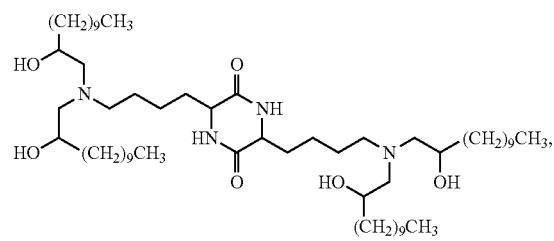

I a pharmaceutically acceptable salt thereof, a solvate thereof, or a solvate of a pharmaceutically acceptable salt thereof, the composition characterized in that greater than or equal to a first threshold amount of the total amount of chemical entities of formula I in the composition:

are chemical entities of formula I.a:

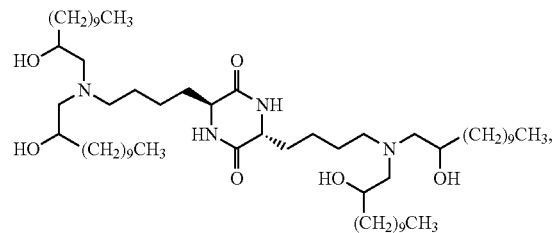

I.a wherein the first threshold amount is 50%; or are chemical entities of formula I.b.1:

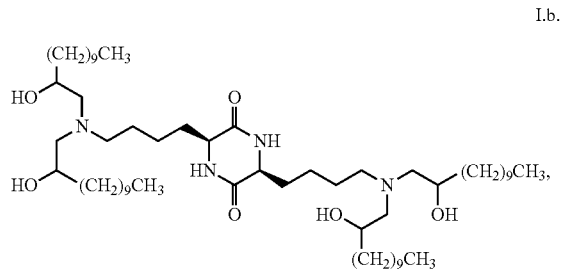

I.b.1 wherein the first threshold amount is 25%; or
are chemical entities of formula I.b.2:

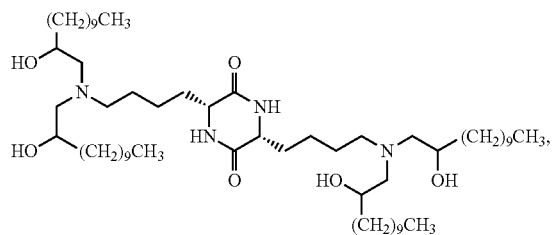

I.b.2 wherein the first threshold amount is 25%.

In some embodiments, the present invention provides a composition comprising one or more chemical entities of formula I, each of which is a compound of formula I:

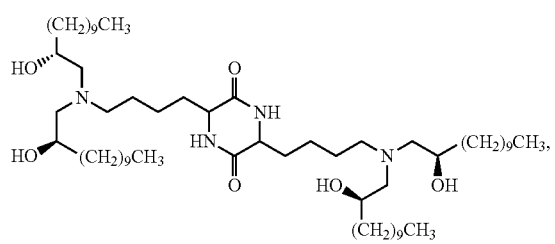

I a pharmaceutically acceptable salt thereof, a solvate thereof, or a solvate of a pharmaceutically acceptable salt thereof, the composition characterized in that greater than a first threshold amount of the total amount of chemical entities of formula I in the composition:
are chemical entities of formula I.c:

I.c

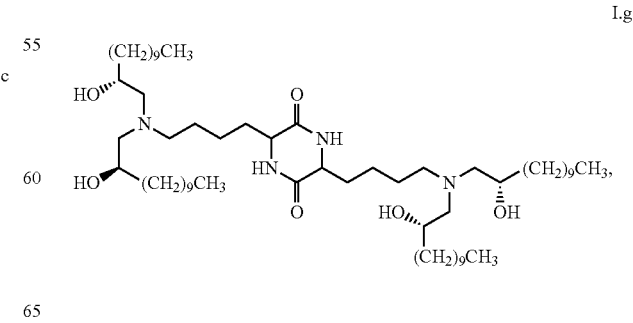

wherein the first threshold amount is 6.25%; or are chemical entities of formula I.d:

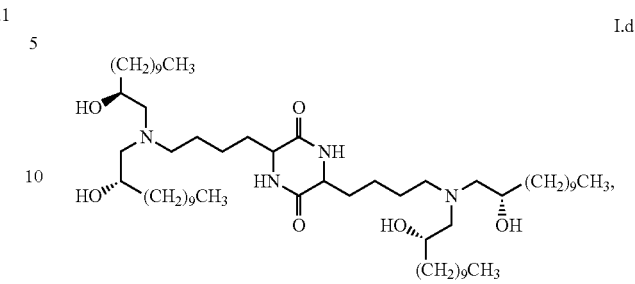

I.d wherein the first threshold amount is 6.25%; or
are chemical entities of formula I.e:

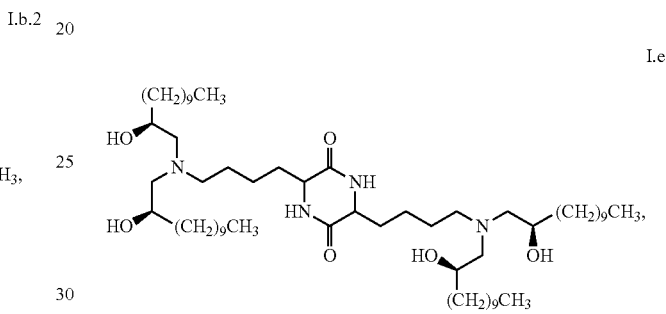

I.e wherein the first threshold amount is 25%; or
are chemical entities of formula I.f:

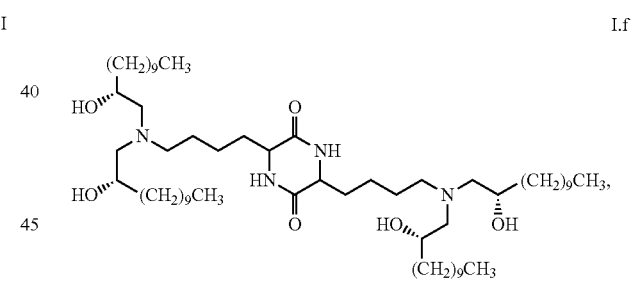

I.f wherein the first threshold amount is 25%; or
are chemical entities of formula I.g:

I.g wherein the first threshold amount is 12.5%; or are chemical entities of formula I.h:

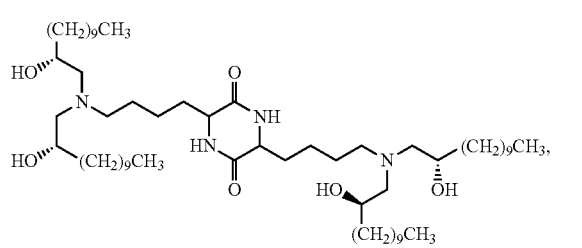

I.h wherein the first threshold amount is 25%.

In some embodiments, the first threshold amount is 50%, 60%, 70%, 80%, 85%, 90%, 91%, 92%, 93%, 94%, 95%, 96%, 97%, 98% or 99%. In some embodiments, the first threshold amount is 50%. In some embodiments, the first threshold amount is 70%. In some embodiments, the first threshold amount is 80%. In some embodiments, the first threshold amount is 95%.

In some embodiments, the present invention provides a composition comprising one or more chemical entities of formula I, each of which is a compound of formula I:

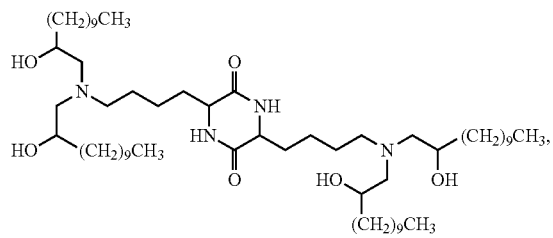

I a pharmaceutically acceptable salt thereof, a solvate thereof, or a solvate of a pharmaceutically acceptable salt thereof, the composition characterized in that greater than or equal to a first threshold amount of the total amount of chemical entities of formula I in the composition are chemical entities of a first formula selected from formulae I.a, I.b.1, I.b.2, I.c, I.d, I.e, I.f, I.g, or I.h; and greater than or equal to a second threshold amount of the total amount of the chemical entities of the first formula in the composition are chemical entities of the same stereoisomer of the first formula.

In some embodiments, greater than or equal to the first threshold amount of the total amount of chemical entities of formula I in the composition are chemical entities of formula I.a.

In some embodiments, greater than or equal to a second threshold amount of the total amount of chemical entities of formula I.a in the composition is a chemical entity of formula I.a.i:

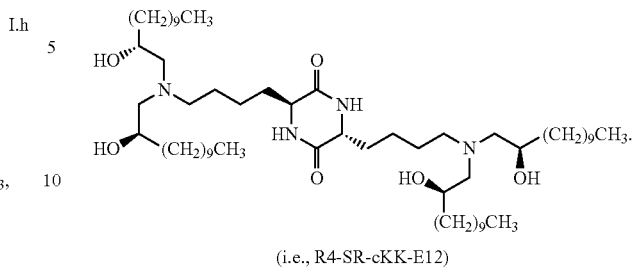

I.a.i (i.e., R4-SR-cKK-E12)

In some embodiments, greater than or equal to a second threshold amount of the total amount of chemical entities of formula I.a in the composition is a chemical entity of formula I.a.ii:

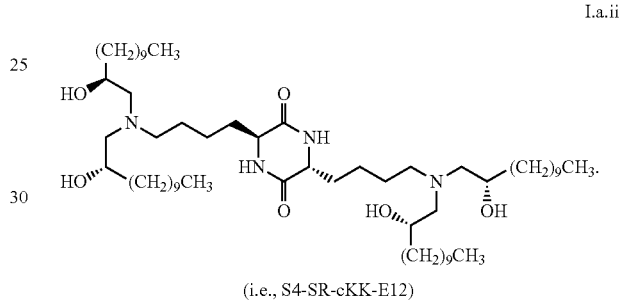

I.a.ii (i.e., S4-SR-cKK-E12)

In some embodiments, greater than or equal to the first threshold amount of the total amount of chemical entities of formula I in the composition are chemical entities of formula I.b.1.

In some embodiments, greater than or equal to a second threshold amount of the total amount of chemical entities of formula I.b.1 in the composition is a chemical entity of formula I.b.1.i:

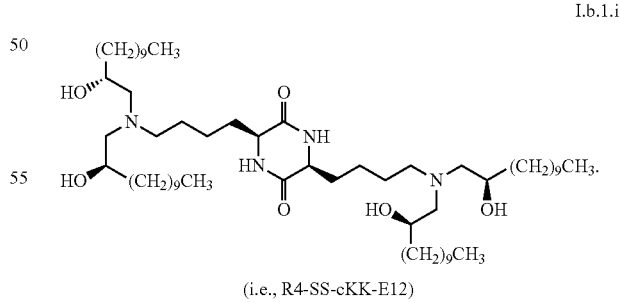

I.b.1.i (i.e., R4-SS-cKK-E12)

In some embodiments, greater than or equal to a second threshold amount of the total amount of chemical entities of formula I.b.1 in the composition is a chemical entity of formula I.b.1.ii:

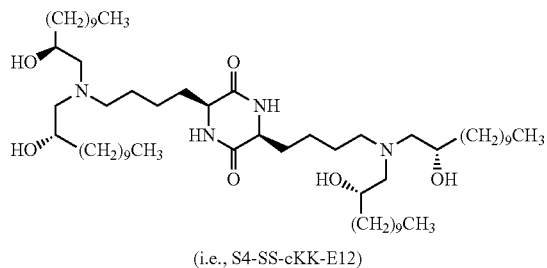

(i.e., S4-SS-cKK-E12)

In some embodiments, greater than or equal to the first threshold amount of the total amount of chemical entities of formula I in the composition are chemical entities of formula I.b.2.

In some embodiments, greater than or equal to a second threshold amount of the total amount of chemical entities of formula I.b.2 in the composition is a chemical entity of formula I.b.2.i:

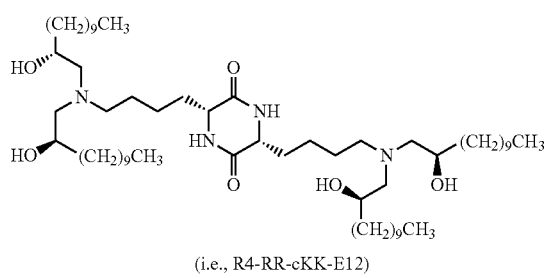

(i.e., R4-RR-cKK-E12)

In some embodiments, greater than or equal to a second threshold amount of the total amount of chemical entities of formula I.b.2 in the composition is a chemical entity of formula I.b.2.ii:

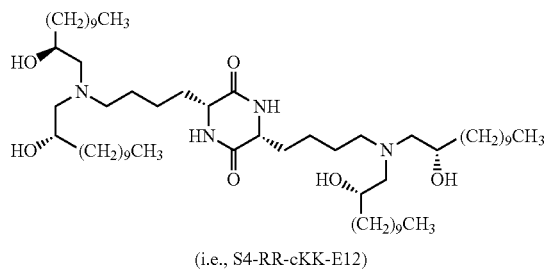

(i.e., S4-RR-cKK-E12)

In some embodiments, the second threshold amount is 50%, 60%, 70%, 80%, 85%, 90%, 91%, 92%, 93%, 94%, 95%, 96%, 97%, 98% or 99%. In some embodiments, the second threshold amount is 50%. In some embodiments, the second threshold amount is 70%. In some embodiments, the second threshold amount is 80%. In some embodiments, the second threshold amount is 95%.

In some embodiments, the present invention provides a composition comprising one or more chemical entities of formula I, each of which is a compound of formula I:

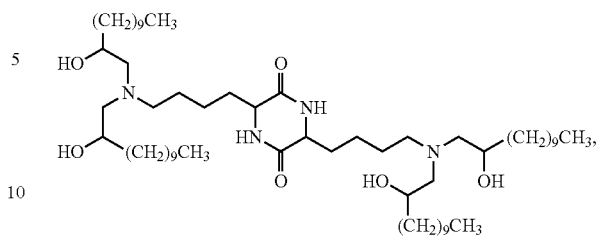

a pharmaceutically acceptable salt thereof, a solvate thereof, or a solvate of a pharmaceutically acceptable salt thereof, the composition characterized in that greater than or equal to a third threshold amount of the total amount of chemical entities of formula I in the composition are chemical entities of formula I.

In some embodiments, the present invention provides a composition comprising one or more chemical entities of formula I, each of which is a compound of formula I:

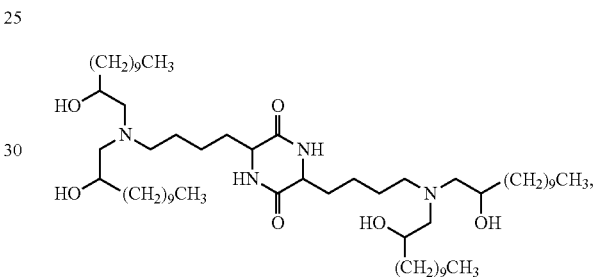

a pharmaceutically acceptable salt thereof, a solvate thereof, or a solvate of a pharmaceutically acceptable salt thereof, the composition characterized in that greater than or equal to a third threshold amount of the total amount of chemical entities of formula I in the composition are chemical entities of the same stereoisomer of formula I.

In some embodiments, a stereoisomer of formula I has the structure of formula I.a.i, I.a.ii, I.b.1.i, I.b.1.ii, I.b.2.i, or I.b.2.ii.

In some embodiments, greater than or equal to the third threshold amount of the total amount of the composition is a chemical entity of formula I.a.i, I.a.ii, I.b.1.i, I.b.1.ii, I.b.2.i, or I.b.2.ii. In some embodiments, greater than or equal to the third threshold amount of the total amount of the composition is a chemical entity of formula I.a.i. In some embodiments, greater than or equal to the third threshold amount of the total amount of the composition is a chemical entity of formula I.a.ii. In some embodiments, greater than or equal to the third threshold amount of the total amount of the composition is a chemical entity of formula I.b.1.i. In some embodiments, greater than or equal to the third threshold amount of the total amount of the composition is a chemical entity of formula I.b.1.ii. In some embodiments, greater than or equal to the third threshold amount of the total amount of the composition is a chemical entity of formula I.b.2.i. In some embodiments, greater than or equal to the third threshold amount of the total amount of the composition is a chemical entity of formula I.b.2.ii.

In some embodiments, the third threshold amount is 50%, 60%, 70%, 80%, 85%, 90%, 91%, 92%, 93%, 94%, 95%, 96%, 97%, 98% or 99% (w/w). In some embodiments, the third threshold amount is 50% (w/w). In some embodiments, the third threshold amount is 70% (w/w). In some embodiments, the third threshold amount is 80% (w/w). In some embodiments, the third threshold amount is 85% (w/w). In some embodiments, the third threshold amount is 95% (w/w).

In some embodiments, a provided composition further comprises one or more mRNA for mRNA delivery and expression of the encoded protein in vivo.

In some embodiments, the present invention provides methods for highly efficient delivery and expression of mRNA and encoded protein in vivo. In some embodiments, the present invention provides a method of delivery of mRNA in vivo, comprising administering to a subject in need of delivery a provided composition which comprises an mRNA. In some embodiments, due to their low toxicity, a provide composition permits more delivered mRNA, higher protein expression level and/or lower administration frequency, thereby providing a more potent, safer, and more patent-friendly mRNA therapy.

BRIEF DESCRIPTION OF THE DRAWING

FIG. 1 depicts the results of in vivo human ASS1 protein production in wild type mouse liver upon treatment with lipid nanoparticles that include compounds of formula I.

DEFINITIONS

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Amino acid: As used herein, term "amino acid," in its broadest sense, refers to any compound and/or substance that can be incorporated into a polypeptide chain. In some embodiments, an amino acid has the general structure $H_2N—C(H)(R)—COHO$. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxyl- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Chemical entity: As used herein, the term "chemical entity" includes a compound, salt, or solvate thereof, or any combination of compounds, salts, or solvates thereof.

Delivery: As used herein, the term "delivery" encompasses both local and systemic delivery. For example, delivery of mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery).

Expression: As used herein, "expression" of a nucleic acid sequence refers to translation of an mRNA into a polypeptide, assemble multiple polypeptides (e.g., heavy chain or light chain of antibody) into an intact protein (e.g., antibody) and/or post-translational modification of a polypeptide or fully assembled protein (e.g., antibody). In this application, the terms "expression" and "production," and grammatical equivalent, are used inter-changeably.

Functional: As used herein, a "functional" biological molecule is a biological molecule in a form in which it exhibits a property and/or activity by which it is characterized.

Half-life: As used herein, the term "half-life" is the time required for a quantity such as nucleic acid or protein concentration or activity to fall to half of its value as measured at the beginning of a time period.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Local distribution or delivery: As used herein, the terms "local distribution," "local delivery," or grammatical equivalent, refer to tissue specific delivery or distribution. Typically, local distribution or delivery requires a protein (e.g., enzyme) encoded by mRNAs be translated and expressed intracellularly or with limited secretion that avoids entering the patient's circulation system.

messenger RNA (mRNA): As used herein, the term "messenger RNA (mRNA)" refers to a polynucleotide that encodes at least one polypeptide. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

In some embodiments, the mRNA comprises one or more nonstandard nucleotide residues. The nonstandard nucleotide residues may include, e.g., 5-methyl-cytidine ("5mC"), pseudouridine, and/or 2-thio-uridine ("2sU"). See, e.g., U.S. Pat. No. 8,278,036 or WO2011012316 for a discussion of such residues and their incorporation into mRNA. The mRNA may be RNA, which is defined as RNA in which 25% of U residues are 2-thio-uridine and 25% of C residues are 5-methylcytidine. Teachings for the use of RNA are disclosed US Patent Publication US20120195936 and internation publication WO2011012316, both of which are hereby incorporated by reference in their entirety. The presence of nonstandard nucleotide residues may render an mRNA more stable and/or less immunogenic than a control mRNA with the same sequence but containing only standard residues. In further embodiments, the mRNA may comprise one or more nonstandard nucleotide residues chosen from isocytosine, pseudoisocytosine, 5-bromouracil, 5-propynyluracil, 6-aminopurine, 2-aminopurine, inosine, diaminopurine and 2-chloro-6-aminopurine cytosine, as well as combinations of these modifications and other nucleobase modifications. Certain embodiments may further include additional modifications to the furanose ring or nucleobase. Additional modifications may include, for example, sugar modifications or substitutions (e.g., one or more of a 2'-O-alkyl modification, a locked nucleic acid (LNA)). In some embodiments, the RNAs may be complexed or hybridized with additional polynucleotides and/or peptide polynucleotides (PNA). In embodiments where the sugar modification is a 2'-O-alkyl modification, such modification may include, but are not limited to a 2'-deoxy-2'-fluoro modification, a 2'-O-methyl modification, a 2'-O-methoxyethyl modification and a 2'-deoxy modification. In certain embodiments, any of these modifications may be present in 0-100% of the nucleotides—for example, more than 0%, 1%, 10%, 25%, 50%, 75%, 85%, 90%, 95%, or 100% of the constituent nucleotides individually or in combination.

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre and post natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Polymer: As used herein, a "polymer" refers to a compound comprised of at least 3 (e.g., at least 10, 20, 30, 40, 50, 60, 70, 80, 90, 100, etc.) repeating covalently bound structural units.

Salt: As used herein, the term "salt" or "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or rnalonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate. digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N+(C1-4alkyl)4 salts. Representative alkali or alkaline earth metal salts include sodium, lithium, potassium, calcium, magnesium, and the like. Further pharmaceutically acceptable salts include, when appropriate, non-toxic ammonium. quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quarternization of an amine using an appropriate electrophile, e.g., an alkyl halide, to form a quarternized alkylated amino salt.

Systemic distribution or delivery: As used herein, the terms "systemic distribution," "systemic delivery," or grammatical equivalent, refer to a delivery or distribution mechanism or approach that affect the entire body or an entire organism. Typically, systemic distribution or delivery is accomplished via body's circulation system, e.g., blood stream. Compared to the definition of "local distribution or delivery."

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Target tissues: As used herein, the term "target tissues" refers to any tissue that is affected by a disease to be treated. In some embodiments, target tissues include those tissues that display disease-associated pathology, symptom, or feature.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION

The present invention provides, among other things, lipid compositions and methods for delivering mRNA in vivo using stereochemically enriched lipid compositions.

Lipid Compositions

In some embodiments, the present invention provides a composition comprising one or more chemical entities of formula I, each of which is a compound of formula I, a pharmaceutically acceptable salt thereof, a solvate thereof, or a solvate of a pharmaceutically acceptable salt thereof, the composition characterized in that greater than or equal to a first threshold amount of the total amount of chemical entities of formula I in the composition are chemical entities of formula I.a, I.b.1, I.b.2, I.c, I.d, I.e, I.f, I.g, or I.h.

In some embodiments, a provided composition is characterized in that greater than a first threshold amount of the total amount of chemical entities of formula I in the composition are chemical entities of formula I.a, I.b.1, I.b.2, I.c, I.d, I.e, I.f, I.g, or I.h. In some embodiments, a provided composition is characterized in that a first threshold amount of the total amount of chemical entities of formula I in the composition are chemical entities of formula I.a, I.b.1, I.b.2, I.c, I.d, I.e, I.f, I.g, or I.h.

As used herein, a "chemical entity" of a formula is a compound of the formula, a pharmaceutically acceptable salt thereof, a solvate thereof, or a solvate of a pharmaceutically acceptable salt thereof.

In some embodiments, the first threshold amount is 50%, 60%, 70%, 80%, 85%, 90%, 91%, 92%, 93%, 94%, 95%, 96%, 97%, 98% or 99%. In some embodiments, the first threshold amount is 50%. In some embodiments, the first threshold amount is 70%. In some embodiments, the first threshold amount is 80%. In some embodiments, the first threshold amount is 95%.

In some embodiments, the composition is characterized in that greater than or equal to a first threshold amount of the total amount of chemical entities of formula I in the composition are chemical entities of formula I.a. In some embodiments, the composition is characterized in that greater than a first threshold amount of the total amount of chemical entities of formula I in the composition are chemical entities of formula I.a. In some embodiments, the composition is characterized in that a first threshold amount of the total amount of chemical entities of formula I in the composition are chemical entities of formula I.a. In some embodiments, a first threshold amount is 50%. In some embodiments, a first threshold amount is 70%. In some embodiments, a first threshold amount is 80%. In some embodiments, a first threshold amount is 90%. In some embodiments, a first threshold amount is 95%.

In some embodiments, the composition is characterized in that greater than or equal to a first threshold amount of the total amount of chemical entities of formula I in the composition are chemical entities of formula I.b.1. In some embodiments, the composition is characterized in that greater than a first threshold amount of the total amount of chemical entities of formula I in the composition are chemical entities of formula I.b.1. In some embodiments, the composition is characterized in that a first threshold amount of the total amount of chemical entities of formula I in the composition are chemical entities of formula I.b.1. In some embodiments, a first threshold amount is 25%. In some embodiments, a first threshold amount is 50%. In some embodiments, a first threshold amount is 70%. In some embodiments, a first threshold amount is 80%. In some embodiments, a first threshold amount is 90%. In some embodiments, a first threshold amount is 95%.

In some embodiments, the composition is characterized in that greater than or equal to a first threshold amount of the total amount of chemical entities of formula I in the composition are chemical entities of formula I.b.2. In some embodiments, the composition is characterized in that greater than a first threshold amount of the total amount of chemical entities of formula I in the composition are chemical entities of formula I.b.2. In some embodiments, the composition is characterized in that a first threshold amount of the total amount of chemical entities of formula I in the composition are chemical entities of formula I.b.2. In some embodiments, a first threshold amount is 25%. In some embodiments, a first threshold amount is 50%. In some embodiments, a first threshold amount is 70%. In some embodiments, a first threshold amount is 80%. In some embodiments, a first threshold amount is 90%. In some embodiments, a first threshold amount is 95%.

In some embodiments, the composition is characterized in that greater than or equal to a first threshold amount of the total amount of chemical entities of formula I in the composition are chemical entities of formula I.c. In some embodiments, the composition is characterized in that greater than a first threshold amount of the total amount of chemical entities of formula I in the composition are chemical entities of formula I.c. In some embodiments, the composition is characterized in that a first threshold amount of the total amount of chemical entities of formula I in the composition are chemical entities of formula I.c. In some embodiments, a first threshold amount is 6.25%. In some embodiments, a first threshold amount is 12.5%. In some embodiments, a first threshold amount is 25%. In some embodiments, a first threshold amount is 50%. In some embodiments, a first threshold amount is 70%. In some embodiments, a first threshold amount is 80%. In some embodiments, a first threshold amount is 90%. In some embodiments, a first threshold amount is 95%.

In some embodiments, the composition is characterized in that greater than or equal to a first threshold amount of the total amount of chemical entities of formula I in the composition are chemical entities of formula I.d. In some embodiments, the composition is characterized in that greater than a first threshold amount of the total amount of chemical entities of formula I in the composition are chemical entities of formula I.d. In some embodiments, the composition is characterized in that a first threshold amount of the total amount of chemical entities of formula I in the composition are chemical entities of formula I.d. In some embodiments, a first threshold amount is 6.25%. In some embodiments, a first threshold amount is 12.5%. In some embodiments, a first threshold amount is 25%. In some embodiments, a first threshold amount is 50%. In some embodiments, a first threshold amount is 70%. In some embodiments, a first threshold amount is 80%. In some embodiments, a first threshold amount is 90%. In some embodiments, a first threshold amount is 95%.

In some embodiments, the composition is characterized in that greater than or equal to a first threshold amount of the total amount of chemical entities of formula I in the composition are chemical entities of formula I.e. In some embodiments, the composition is characterized in that greater than a first threshold amount of the total amount of chemical entities of formula I in the composition are chemical entities of formula I.e. In some embodiments, the composition is characterized in that a first threshold amount of the total amount of chemical entities of formula I in the composition are chemical entities of formula I.e. In some embodiments, a first threshold amount is 25%. In some embodiments, a first threshold amount is 50%. In some embodiments, a first threshold amount is 70%. In some embodiments, a first threshold amount is 80%. In some embodiments, a first threshold amount is 90%. In some embodiments, a first threshold amount is 95%.

In some embodiments, the composition is characterized in that greater than or equal to a first threshold amount of the total amount of chemical entities of formula I in the composition are chemical entities of formula I.f. In some embodiments, the composition is characterized in that greater than a first threshold amount of the total amount of chemical entities of formula I in the composition are chemical entities of formula I.f. In some embodiments, the composition is characterized in that a first threshold amount of the total amount of chemical entities of formula I in the composition are chemical entities of formula I.f. In some embodiments, a first threshold amount is 25%. In some embodiments, a first threshold amount is 50%. In some embodiments, a first threshold amount is 70%. In some embodiments, a first threshold amount is 80%. In some embodiments, a first threshold amount is 90%. In some embodiments, a first threshold amount is 95%.

In some embodiments, the composition is characterized in that greater than or equal to a first threshold amount of the total amount of chemical entities of formula I in the composition are chemical entities of formula I.g. In some embodiments, the composition is characterized in that greater than a first threshold amount of the total amount of chemical entities of formula I in the composition are chemical entities of formula I.g. In some embodiments, the composition is characterized in that a first threshold amount of the total amount of chemical entities of formula I in the composition are chemical entities of formula I.g. In some embodiments, a first threshold amount is 12.5%. In some embodiments, a first threshold amount is 25%. In some embodiments, a first threshold amount is 50%. In some embodiments, a first threshold amount is 70%. In some embodiments, a first threshold amount is 80%. In some embodiments, a first threshold amount is 90%. In some embodiments, a first threshold amount is 95%.

In some embodiments, the composition is characterized in that greater than or equal to a first threshold amount of the total amount of chemical entities of formula I in the composition are chemical entities of formula I.h. In some embodiments, the composition is characterized in that greater than a first threshold amount of the total amount of chemical entities of formula I in the composition are chemical entities of formula I.h. In some embodiments, the composition is characterized in that a first threshold amount of the total amount of chemical entities of formula I in the composition are chemical entities of formula I.h. In some embodiments, a first threshold amount is 25%. In some embodiments, a first threshold amount is 50%. In some embodiments, a first threshold amount is 70%. In some embodiments, a first threshold amount is 80%. In some embodiments, a first threshold amount is 90%. In some embodiments, a first threshold amount is 95%.

In some embodiments, the present invention provides a composition comprising one or more chemical entities of formula I, each of which is a compound of formula I:

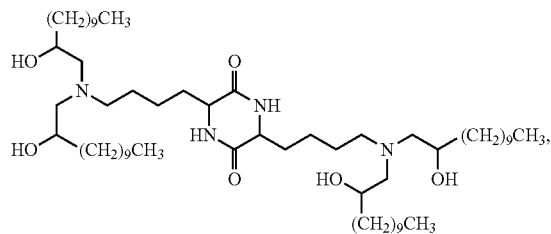

I a pharmaceutically acceptable salt thereof, a solvate thereof, or a solvate of a pharmaceutically acceptable salt thereof, the composition characterized in that greater than or equal to
 a first threshold amount of the total amount of chemical entities of formula I in the composition are chemical entities of a first formula selected from formulae I.a, I.b.1, I.b.2, I.c, I.d, I.e, I.f, I.g, and I.h; and
greater than or equal to a second threshold amount of the total amount of the chemical entities of the first formula in the composition are chemical entities of the same stereoisomer of the first formula.

In some embodiments, greater than a first threshold amount of the total amount of chemical entities of formula I in the composition are chemical entities of a first formula selected from formulae I.a, I.b.1, I.b.2, I.c, I.d, I.e, I.f, I.g, and I.h. In some embodiments, a first threshold amount of the total amount of chemical entities of formula I in the composition are chemical entities of a first formula selected from formulae I.a, I.b.1, I.b.2, I.c, I.d, I.e, I.f, I.g, and I.h. In some embodiments, greater than a second threshold amount of the total amount of the chemical entities of the first formula in the composition are chemical entities of the same stereoisomer of the first formula. In some embodiments, a second threshold amount of the total amount of the chemical entities of the first formula in the composition are chemical entities of the same stereoisomer of the first formula.

In some embodiments, a first formula is formula I.a. In some embodiments, greater than or equal to the first threshold amount of the total amount of chemical entities of formula I in the composition are chemical entities of formula I.a, and greater than or equal to a second threshold amount of the total amount of the chemical entities of formula I.a in the composition are chemical entities of the same stereoisomer of formula I.a.

In some embodiments, a stereoisomer of formula I.a has the structure of formula I.a.i:

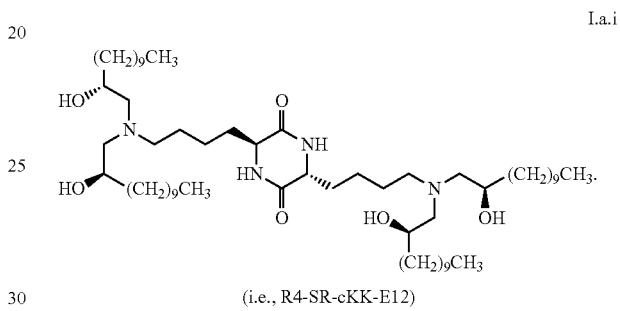

(i.e., R4-SR-cKK-E12)

In some embodiments, a stereoisomer of formula I.a has the structure of formula I.a.ii:

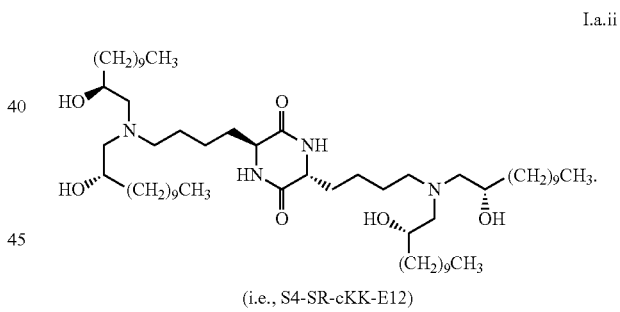

(i.e., S4-SR-cKK-E12)

In some embodiments, a stereoisomer of formula I.a has the structure of formula I.a.iii:

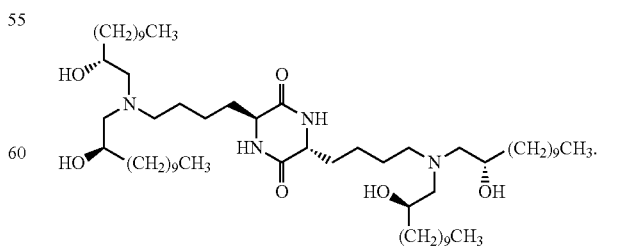

In some embodiments, a stereoisomer of formula I.a has the structure of formula I.a.iv:

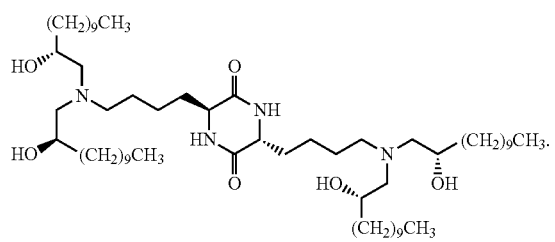

I.a.iv

In some embodiments, a stereoisomer of formula I.a has the structure of formula I.a.v:

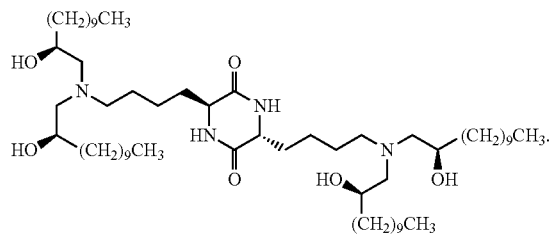

I.a.v

In some embodiments, a stereoisomer of formula I.a has the structure of formula I.a.vi:

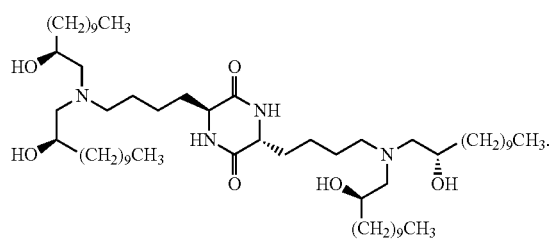

I.a.vi

In some embodiments, a stereoisomer of formula I.a has the structure of formula I.a.vii:

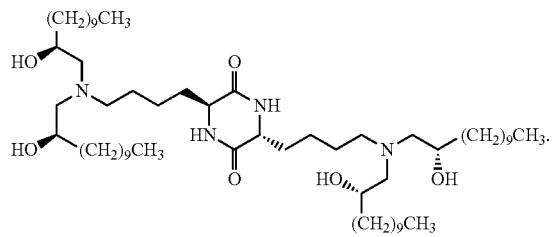

I.a.vii

In some embodiments, a stereoisomer of formula I.a has the structure of formula I.a.viii:

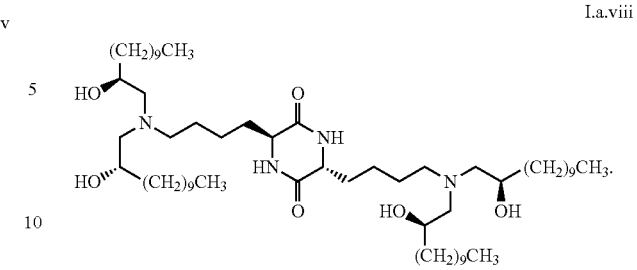

I.a.viii

In some embodiments, a stereoisomer of formula I.a has the structure of formula I.a.ix:

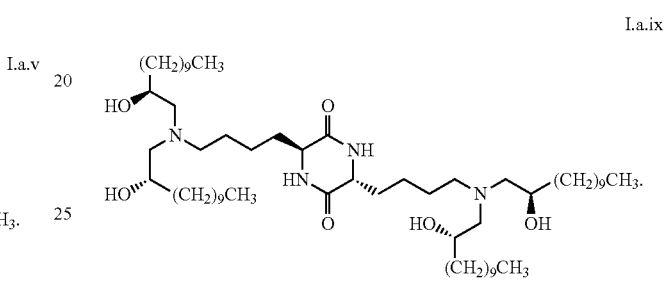

I.a.ix

In some embodiments, a stereoisomer of formula I.a has the structure of formula I.a.x:

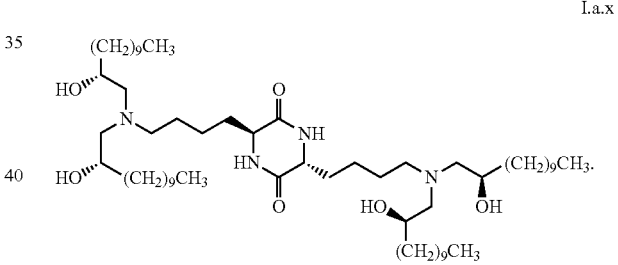

I.a.x

In some embodiments, greater than or equal to a second threshold amount of the total amount of chemical entities of formula I.a in the composition are chemical entities of formula I.a.i. In some embodiments, greater than or equal to a second threshold amount of the total amount of chemical entities of formula I.a in the composition are chemical entities of formula I.a.ii. In some embodiments, greater than or equal to a second threshold amount of the total amount of chemical entities of formula I.a in the composition are chemical entities of formula I.a.iii. In some embodiments, greater than or equal to a second threshold amount of the total amount of chemical entities of formula I.a in the composition are chemical entities of formula I.a.iv. In some embodiments, greater than or equal to a second threshold amount of the total amount of chemical entities of formula I.a in the composition are chemical entities of formula I.a.v. In some embodiments, greater than or equal to a second threshold amount of the total amount of chemical entities of formula I.a in the composition are chemical entities of formula I.a.vi. In some embodiments, greater than or equal to a second threshold amount of the total amount of chemical entities of formula I.a in the composition are chemical entities of formula I.a.vii. In some embodiments, greater than or equal to a second threshold amount of the total amount of chemical entities of formula I.a in the composition are chemical entities of formula I.a.viii. In some embodiments, greater than or equal to a second threshold amount of the total amount of chemical entities of formula I.a in the composition are chemical entities of formula I.a.ix.

In some embodiments, a first formula is formula I.b.1. In some embodiments, greater than or equal to the first threshold amount of the total amount of chemical entities of formula I in the composition are chemical entities of formula I.b.1, and greater than or equal to a second threshold amount of the total amount of the chemical entities of formula I.b.1 in the composition are chemical entities of the same stereoisomer of formula I.b.1.

In some embodiments, a stereoisomer of formula I.b.1 has the structure of formula I.b.1.i (i.e., R4-SS-cKK-E12).

In some embodiments, a stereoisomer of formula I.b.1 has the structure of formula I.b.1.ii (i.e., S4-SS-cKK-E12).

In some embodiments, a stereoisomer of formula I.b.1 has the structure of formula I.b.1.iii:

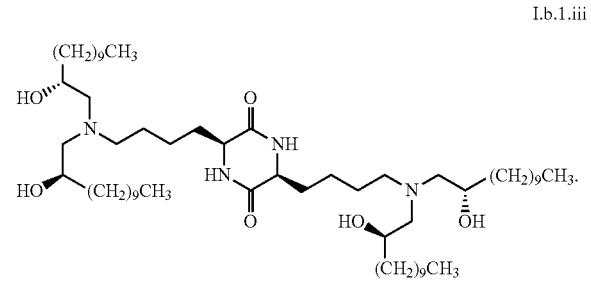

I.b.1.iii

In some embodiments, a stereoisomer of formula I.b.1 has the structure of formula I.b.1.iv:

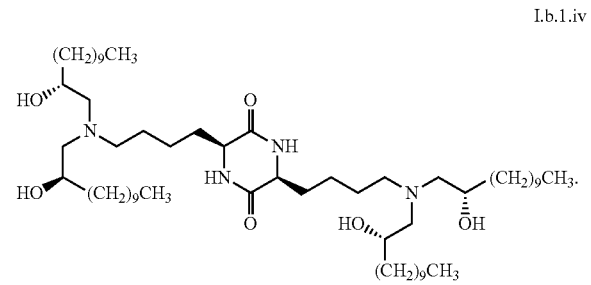

I.b.1.iv

In some embodiments, a stereoisomer of formula I.b.1 has the structure of formula I.b.1.v:

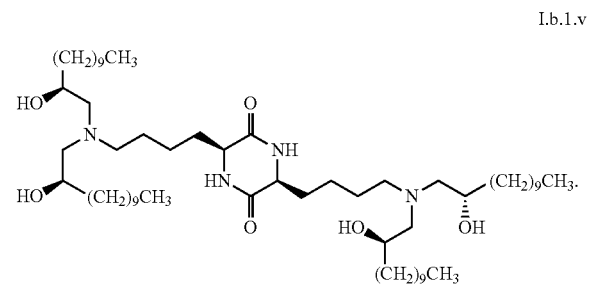

I.b.1.v

In some embodiments, a stereoisomer of formula I.b.1 has the structure of formula I.b.1.vi:

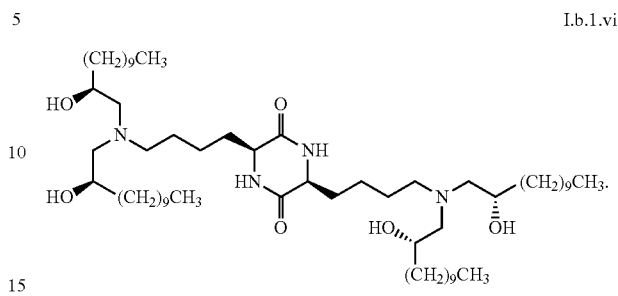

I.b.1.vi

In some embodiments, greater than or equal to a second threshold amount of the total amount of chemical entities of formula I.b.1 in the composition are chemical entities of formula I.b.1.i. In some embodiments, greater than or equal to a second threshold amount of the total amount of chemical entities of formula I.b.1 in the composition are chemical entities of formula I.b.1.ii. In some embodiments, greater than or equal to a second threshold amount of the total amount of chemical entities of formula I.b.1 in the composition are chemical entities of formula I.b.1.iii. In some embodiments, greater than or equal to a second threshold amount of the total amount of chemical entities of formula I.b.1 in the composition are chemical entities of formula I.b.1.iv. In some embodiments, greater than or equal to a second threshold amount of the total amount of chemical entities of formula I.b.1 in the composition are chemical entities of formula I.b.1.v. In some embodiments, greater than or equal to a second threshold amount of the total amount of chemical entities of formula I.b.1 in the composition are chemical entities of formula I.b.1.vi.

In some embodiments, a first formula is formula I.b.2. In some embodiments, greater than or equal to the first threshold amount of the total amount of chemical entities of formula I in the composition are chemical entities of formula I.b.2, and greater than or equal to a second threshold amount of the total amount of the chemical entities of formula I.b.2 in the composition are chemical entities of the same stereoisomer of formula I.b.2.

In some embodiments, a stereoisomer of formula I.b.2 has the structure of formula I.b.2.i (i.e., R4-RR-cKK-E12).

In some embodiments, a stereoisomer of formula I.b.2 has the structure of formula I.b.2.ii (i.e., S4-RR-cKK-E12).

In some embodiments, a stereoisomer of formula I.b.2 has the structure of formula I.b.2.iii:

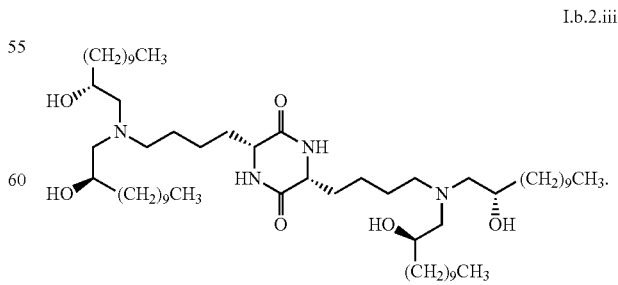

I.b.2.iii

In some embodiments, a stereoisomer of formula I.b.2 has the structure of formula I.b.2.iv:

I.b.2.iv

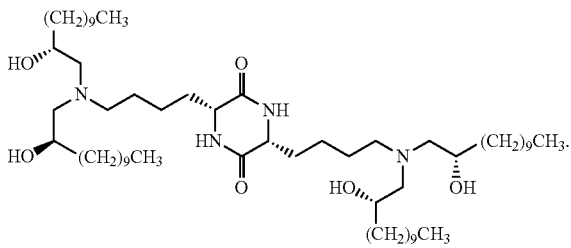

In some embodiments, a stereoisomer of formula I.b.2 has the structure of formula I.b.2.v:

I.b.2.v

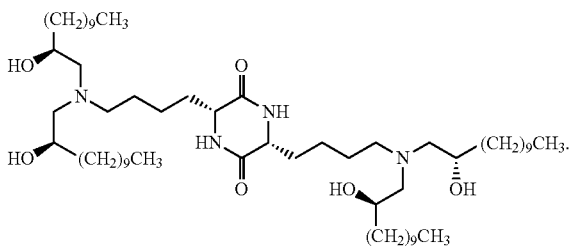

In some embodiments, a stereoisomer of formula I.b.2 has the structure of formula I.b.2.vi:

I.b.2.vi

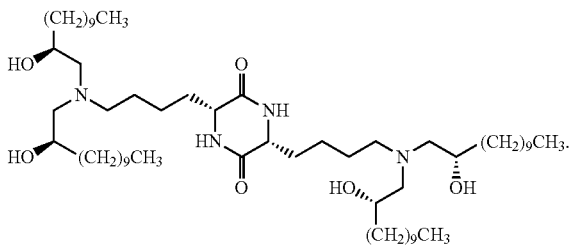

In some embodiments, greater than or equal to a second threshold amount of the total amount of chemical entities of formula I.b.2 in the composition are chemical entities of formula I.b.2.i. In some embodiments, greater than or equal to a second threshold amount of the total amount of chemical entities of formula I.b.2 in the composition are chemical entities of formula I.b.2.ii. In some embodiments, greater than or equal to a second threshold amount of the total amount of chemical entities of formula I.b.2 in the composition are chemical entities of formula I.b.2.iii. In some embodiments, greater than or equal to a second threshold amount of the total amount of chemical entities of formula I.b.2 in the composition are chemical entities of formula I.b.2.iv. In some embodiments, greater than or equal to a second threshold amount of the total amount of chemical entities of formula I.b.2 in the composition are chemical entities of formula I.b.2.v. In some embodiments, greater than or equal to a second threshold amount of the total amount of chemical entities of formula I.b.2 in the composition are chemical entities of formula I.b.2.vi.

In some embodiments, a first formula is formula I.c. In some embodiments, greater than or equal to the first threshold amount of the total amount of chemical entities of formula I in the composition are chemical entities of formula I.c, and greater than or equal to a second threshold amount of the total amount of the chemical entities of formula I.c in the composition are chemical entities of the same stereoisomer of formula I.c. In some embodiments, a stereoisomer of formula I.c has the structure of formula I.a.i. In some embodiments, a stereoisomer of formula I.c has the structure of formula I.b.1.i. In some embodiments, a stereoisomer of formula I.c has the structure of formula I.b.2.i. In some embodiments, greater than or equal to a second threshold amount of the total amount of chemical entities of formula I.c in the composition are chemical entities of formula I.a.i. In some embodiments, greater than or equal to a second threshold amount of the total amount of chemical entities of formula I.c in the composition are chemical entities of formula I.b.1.i. In some embodiments, greater than or equal to a second threshold amount of the total amount of chemical entities of formula I.c in the composition are chemical entities of formula I.b.2.i.

In some embodiments, a first formula is formula I.d. In some embodiments, greater than or equal to the first threshold amount of the total amount of chemical entities of formula I in the composition are chemical entities of formula I.d, and greater than or equal to a second threshold amount of the total amount of the chemical entities of formula I.d in the composition are chemical entities of the same stereoisomer of formula I.d. In some embodiments, a stereoisomer of formula I.d has the structure of formula I.a.ii. In some embodiments, a stereoisomer of formula I.d has the structure of formula I.b.1.ii. In some embodiments, a stereoisomer of formula I.d has the structure of formula I.b.2.ii. In some embodiments, greater than or equal to a second threshold amount of the total amount of chemical entities of formula I.d in the composition are chemical entities of formula I.a.ii. In some embodiments, greater than or equal to a second threshold amount of the total amount of chemical entities of formula I.d in the composition are chemical entities of formula I.b.1.ii. In some embodiments, greater than or equal to a second threshold amount of the total amount of chemical entities of formula I.d in the composition are chemical entities of formula I.b.2.ii.

In some embodiments, a first formula is formula I.e. In some embodiments, greater than or equal to the first threshold amount of the total amount of chemical entities of formula I in the composition are chemical entities of formula I.e, and greater than or equal to a second threshold amount of the total amount of the chemical entities of formula I.e in the composition are chemical entities of the same stereoisomer of formula I.e. In some embodiments, a stereoisomer of formula I.e has the structure of formula I.a.iii. In some embodiments, a stereoisomer of formula I.e has the structure of formula I.a.v. In some embodiments, a stereoisomer of formula I.e has the structure of formula I.b.1.iii. In some embodiments, a stereoisomer of formula I.e has the structure of formula I.b.2.iii. In some embodiments, greater than or equal to a second threshold amount of the total amount of chemical entities of formula I.e in the composition are chemical entities of formula I.a.iii. In some embodiments, greater than or equal to a second threshold amount of the total amount of chemical entities of formula I.e in the composition are chemical entities of formula I.a.v. In some embodiments, greater than or equal to a second threshold amount of the total amount of chemical entities of formula I.e in the composition are chemical entities of formula I.b.1.iii. In some embodiments, greater than or equal to a second threshold amount of the total amount of chemical entities of formula I.e in the composition are chemical entities of formula I.b.2.iii.

In some embodiments, a first formula is formula I.f. In some embodiments, greater than or equal to the first threshold amount of the total amount of chemical entities of formula I in the composition are chemical entities of formula I.f, and greater than or equal to a second threshold amount of the total amount of the chemical entities of formula I.f in the composition are chemical entities of the same stereoisomer of formula I.f. In some embodiments, a stereoisomer of formula I.f has the structure of formula I.a.vii. In some embodiments, a stereoisomer of formula I.f has the structure of formula I.a.ix. In some embodiments, a stereoisomer of formula I.f has the structure of formula I.b.1.vi. In some embodiments, a stereoisomer of formula I.f has the structure of formula I.b.2.vi. In some embodiments, greater than or equal to a second threshold amount of the total amount of chemical entities of formula I.f in the composition are chemical entities of formula I.a.iii. In some embodiments, greater than or equal to a second threshold amount of the total amount of chemical entities of formula I.f in the composition are chemical entities of formula I.a.ix. In some embodiments, greater than or equal to a second threshold amount of the total amount of chemical entities of formula I.f in the composition are chemical entities of formula I.b.1.vi. In some embodiments, greater than or equal to a second threshold amount of the total amount of chemical entities of formula I.f in the composition are chemical entities of formula I.b.2.vi.

In some embodiments, a first formula is formula I.g. In some embodiments, greater than or equal to the first threshold amount of the total amount of chemical entities of formula I in the composition are chemical entities of formula I.g, and greater than or equal to a second threshold amount of the total amount of the chemical entities of formula I.g in the composition are chemical entities of the same stereoisomer of formula I.g. In some embodiments, a stereoisomer of formula I.g has the structure of formula I.a.iv. In some embodiments, a stereoisomer of formula I.g has the structure of formula I.a.viii. In some embodiments, a stereoisomer of formula I.g has the structure of formula I.b.1.iv. In some embodiments, a stereoisomer of formula I.g has the structure of formula I.b.2.iv. In some embodiments, greater than or equal to a second threshold amount of the total amount of chemical entities of formula I.g in the composition are chemical entities of formula I.a.iv. In some embodiments, greater than or equal to a second threshold amount of the total amount of chemical entities of formula I.g in the composition are chemical entities of formula I.a.viii. In some embodiments, greater than or equal to a second threshold amount of the total amount of chemical entities of formula I.g in the composition are chemical entities of formula I.b.1.iv. In some embodiments, greater than or equal to a second threshold amount of the total amount of chemical entities of formula I.g in the composition are chemical entities of formula I.b.2.iv.

In some embodiments, a first formula is formula I.h. In some embodiments, greater than or equal to the first threshold amount of the total amount of chemical entities of formula I in the composition are chemical entities of formula I.h, and greater than or equal to a second threshold amount of the total amount of the chemical entities of formula I.h in the composition are chemical entities of the same stereoisomer of formula I.h. In some embodiments, a stereoisomer of formula I.h has the structure of formula I.a.vi. In some embodiments, a stereoisomer of formula I.h has the structure of formula I.b.1.v. In some embodiments, a stereoisomer of formula I.h has the structure of formula I.b.2.v. In some embodiments, greater than or equal to a second threshold amount of the total amount of chemical entities of formula I.h in the composition are chemical entities of formula I.a.vi. In some embodiments, greater than or equal to a second threshold amount of the total amount of chemical entities of formula I.h in the composition are chemical entities of formula I.b.1.v. In some embodiments, greater than or equal to a second threshold amount of the total amount of chemical entities of formula I.h in the composition are chemical entities of formula I.b.2.v.

In some embodiments, the second threshold amount is 10%, 20%, 30%, 40%, 50%, 60%, 70%, 80%, 85%, 90%, 91%, 92%, 93%, 94%, 95%, 96%, 97%, 98% or 99%. In some embodiments, the second threshold amount is 50%. In some embodiments, the second threshold amount is 70%. In some embodiments, the second threshold amount is 80%. In some embodiments, the second threshold amount is 85%. In some embodiments, the second threshold amount is 90%. In some embodiments, the second threshold amount is 95%.

In some embodiments, the present invention provides a composition comprising one or more chemical entities of formula I, each of which is a compound of formula I:

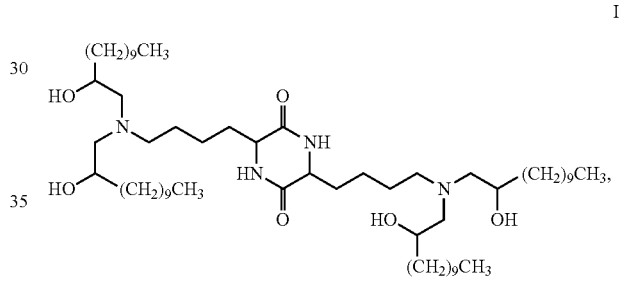

a pharmaceutically acceptable salt thereof, a solvate thereof, or a solvate of a pharmaceutically acceptable salt thereof, the composition characterized in that greater than or equal to a third threshold amount of the total amount of chemical entities of formula I in the composition are chemical entities of formula I.

In some embodiments, a provided composition is characterized in that greater than a third threshold amount of the total amount of chemical entities of formula I in the composition are chemical entities of formula I. In some embodiments, a provided composition is characterized in that a third threshold amount of the total amount of chemical entities of formula I in the composition are chemical entities of formula I.

In some embodiments, a provided composition is characterized in that greater than or equal to a third threshold amount of the total amount of chemical entities of formula I in the composition are chemical entities of formula I.a, I.b.1, I.b.2, I.c, I.d, I.e, I.f, I.g, or I.h. In some embodiments, a provided composition is characterized in that greater than or equal to a third threshold amount of the total amount of chemical entities of formula I in the composition are chemical entities of formula I.a. In some embodiments, a provided composition is characterized in that greater than or equal to a third threshold amount of the total amount of chemical entities of formula I in the composition are chemical entities of formula I.b.1. In some embodiments, a provided composition is characterized in that greater than or equal to a third threshold amount of the total amount of chemical entities of formula I in the composition are chemical entities of formula I.b.2. In some embodiments, a provided composition is characterized in that greater than or equal to a third threshold amount of the total amount of chemical entities of formula I in the composition are chemical entities of formula I.c. In some embodiments, a provided composition is characterized in that greater than or equal to a third threshold amount of the total amount of chemical entities of formula I in the composition are chemical entities of formula I.d. In some embodiments, a provided composition is characterized in that greater than or equal to a third threshold amount of the total amount of chemical entities of formula I in the composition are chemical entities of formula I.e. In some embodiments, a provided composition is characterized in that greater than or equal to a third threshold amount of the total amount of chemical entities of formula I in the composition are chemical entities of formula I.f. In some embodiments, a provided composition is characterized in that greater than or equal to a third threshold amount of the total amount of chemical entities of formula I in the composition are chemical entities of formula I.g. In some embodiments, a provided composition is characterized in that greater than or equal to a third threshold amount of the total amount of chemical entities of formula I in the composition are chemical entities of formula I.h.

In some embodiments, a provided composition is characterized in that greater than or equal to a third threshold amount of the total amount of chemical entities of formula I in the composition are chemical entities of formula I.a.i, I.a.ii, I.a.iii, I.a.iv, I.a.v, I.a.vi, I.a.vii, I.a.viii, I.a.ix, I.b.1.i, I.b.1.ii, I.b.1.iii, I.b.1.iv, I.b.1.v, I.b.1.vi, I.b.2.i, I.b.2.ii, I.b.2.iii, I.b.2.iv, I.b.2.v, and I.b.2.vi.

In some embodiments, the present invention provides a composition comprising one or more chemical entities of formula I, each of which is a compound of formula I:

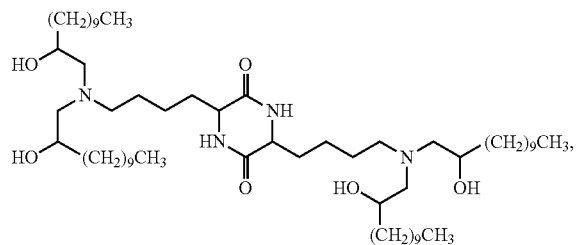

I a pharmaceutically acceptable salt thereof, a solvate thereof, or a solvate of a pharmaceutically acceptable salt thereof, the composition characterized in that greater than or equal to a third threshold amount of the total amount of chemical entities of formula I in the composition are chemical entities of the same stereoisomer of formula I.

In some embodiments, a provided composition is characterized in that greater than a third threshold amount of the total amount of chemical entities of formula I in the composition are chemical entities of the same stereoisomer of formula I. In some embodiments, a provided composition is characterized in that a third threshold amount of the total amount of chemical entities of formula I in the composition are chemical entities of the same stereoisomer of formula I.

In some embodiments, a stereoisomer of formula I has the structure of formula I.a.i, I.a.ii, I.a.iii, I.a.iv, I.a.v, I.a.vi, I.a.vii, I.a.viii, or I.a.ix. In some embodiments, a stereoisomer of formula I has the structure of formula I.a.i. In some embodiments, a stereoisomer of formula I has the structure of formula I.a.ii. In some embodiments, a stereoisomer of formula I has the structure of formula I.a.iii. In some embodiments, a stereoisomer of formula I has the structure of formula I.a.iv. In some embodiments, a stereoisomer of formula I has the structure of formula I.a.v. In some embodiments, a stereoisomer of formula I has the structure of formula I.a.vi. In some embodiments, a stereoisomer of formula I has the structure of formula I.a.vii. In some embodiments, a stereoisomer of formula I has the structure of formula I.a.viii. In some embodiments, a stereoisomer of formula I has the structure of formula I.a.ix.

In some embodiments, a stereoisomer of formula I has the structure of formula I.b.1.i, I.b.1.ii, I.b.1.iii, I.b.1.iv, I.b.1.v, or I.b.1.vi. In some embodiments, a stereoisomer of formula I has the structure of formula I.b.1.i. In some embodiments, a stereoisomer of formula I has the structure of formula I.b.1.ii. In some embodiments, a stereoisomer of formula I has the structure of formula I.b.1.iii. In some embodiments, a stereoisomer of formula I has the structure of formula I.b.1.iv. In some embodiments, a stereoisomer of formula I has the structure of formula I.b.1.v. In some embodiments, a stereoisomer of formula I has the structure of formula I.b.1.vi.

In some embodiments, a stereoisomer of formula I has the structure of formula I.b.2.i, I.b.2.ii, I.b.2.iii, I.b.2.iv, I.b.2.v, or I.b.2.vi. In some embodiments, a stereoisomer of formula I has the structure of formula I.b.2.i. In some embodiments, a stereoisomer of formula I has the structure of formula I.b.2.ii. In some embodiments, a stereoisomer of formula I has the structure of formula I.b.2.iii. In some embodiments, a stereoisomer of formula I has the structure of formula I.b.2.iv. In some embodiments, a stereoisomer of formula I has the structure of formula I.b.2.v. In some embodiments, a stereoisomer of formula I has the structure of formula I.b.2.vi.

In some embodiments, the third threshold amount is 50%, 60%, 70%, 80%, 85%, 90%, 91%, 92%, 93%, 94%, 95%, 96%, 97%, 98% or 99% (w/w). In some embodiments, the third threshold amount is 50% (w/w). In some embodiments, the third threshold amount is 70% (w/w). In some embodiments, the third threshold amount is 80% (w/w). In some embodiments, the third threshold amount is 85% (w/w). In some embodiments, the third threshold amount is 90% (w/w). In some embodiments, the third threshold amount is 95% (w/w). In some embodiments, the third threshold amount is 96% (w/w). In some embodiments, the third threshold amount is 97% (w/w). In some embodiments, the third threshold amount is 98% (w/w). In some embodiments, the third threshold amount is 99% (w/w).

In some embodiments, the present invention provides a composition comprising one or more chemical entities of formula I, each of which is a compound of formula I:

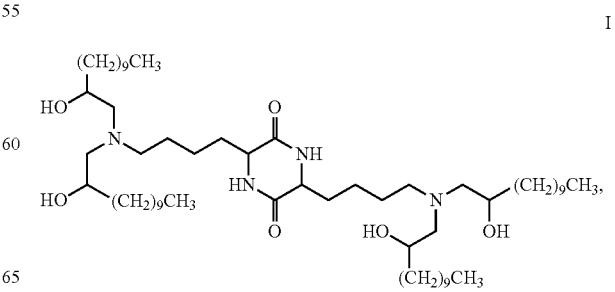

I a pharmaceutically acceptable salt thereof, a solvate thereof, or a solvate of a pharmaceutically acceptable salt thereof, the composition characterized in that greater than a third threshold amount of the total amount of chemical entities of formula I in the composition are chemical entities of formula I.a.i:

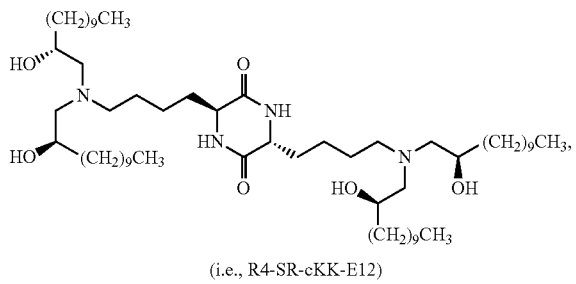

(i.e., R4-SR-cKK-E12)

wherein the third threshold amount is 50%.

In some embodiments, the present invention provides a composition comprising one or more chemical entities of formula I, each of which is a compound of formula I:

I

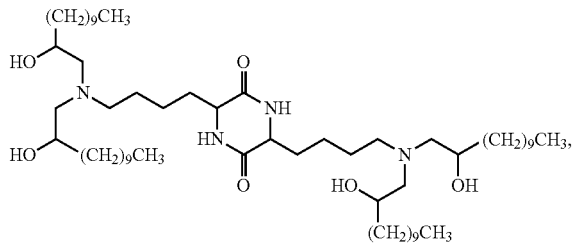

a pharmaceutically acceptable salt thereof, a solvate thereof, or a solvate of a pharmaceutically acceptable salt thereof, the composition characterized in that greater than a third threshold amount of the total amount of chemical entities of formula I in the composition are chemical entities of formula I.a.ii:

I.a.ii

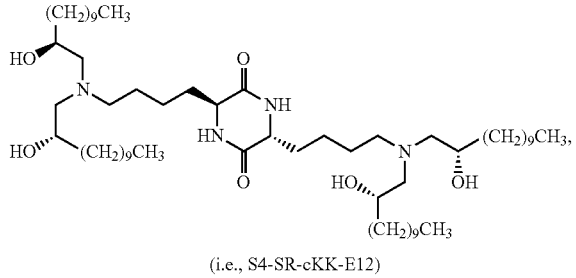

(i.e., S4-SR-cKK-E12)

wherein the third threshold amount is 50%.

In some embodiments, the present invention provides a composition comprising one or more chemical entities of formula I, each of which is a compound of formula I:

I

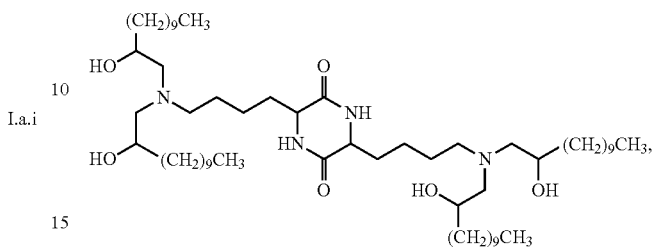

a pharmaceutically acceptable salt thereof, a solvate thereof, or a solvate of a pharmaceutically acceptable salt thereof, the composition characterized in that greater than a third threshold amount of the total amount of chemical entities of formula I in the composition are chemical entities of formula I.b.1.i:

I.b.1.i

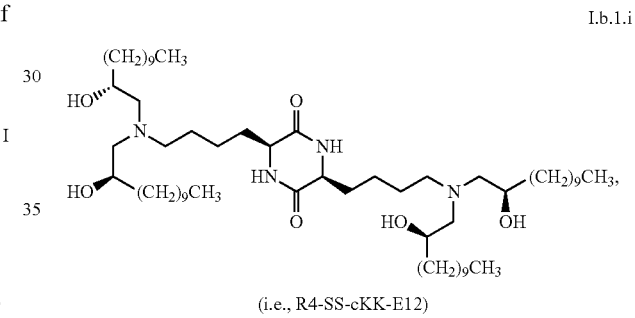

(i.e., R4-SS-cKK-E12)

wherein the third threshold amount is 50%.

In some embodiments, the present invention provides a composition comprising one or more chemical entities of formula I, each of which is a compound of formula I:

I

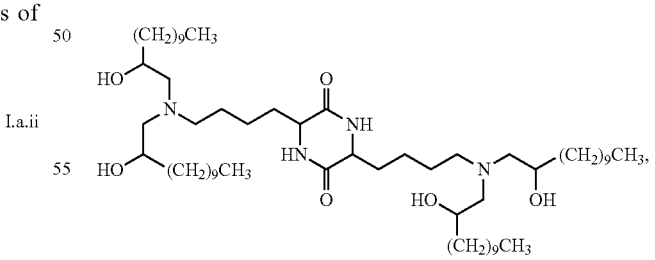

a pharmaceutically acceptable salt thereof, a solvate thereof, or a solvate of a pharmaceutically acceptable salt thereof, the composition characterized in that greater than a third threshold amount of the total amount of chemical entities of formula I in the composition are chemical entities of formula I.b.1.ii:

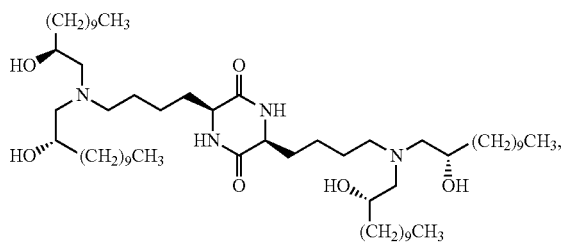

I.b.1.ii (i.e., S4-SS-cKK-E12)

wherein the third threshold amount is 50%.

In some embodiments, the present invention provides a composition comprising one or more chemical entities of formula I, each of which is a compound of formula I:

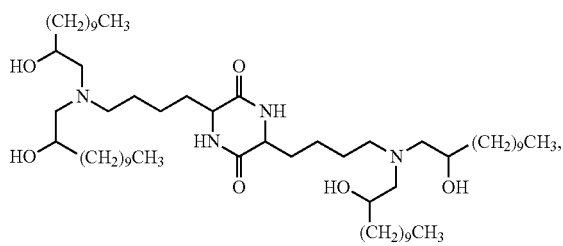

I a pharmaceutically acceptable salt thereof, a solvate thereof, or a solvate of a pharmaceutically acceptable salt thereof, the composition characterized in that greater than a third threshold amount of the total amount of chemical entities of formula I in the composition are chemical entities of formula I.b.2.i:

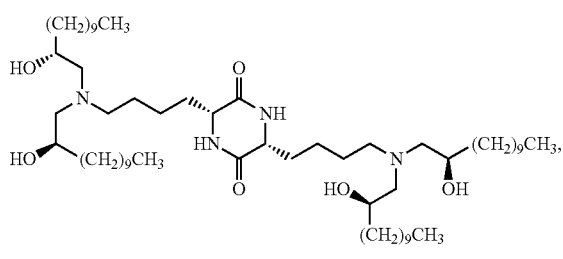

I.b.2.i (i.e., R4-RR-cKK-E12)

wherein the third threshold amount is 50%.

In some embodiments, the present invention provides a composition comprising one or more chemical entities of formula I, each of which is a compound of formula I:

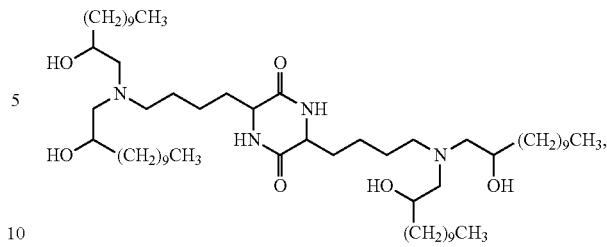

I a pharmaceutically acceptable salt thereof, a solvate thereof, or a solvate of a pharmaceutically acceptable salt thereof, the composition characterized in that greater than a third threshold amount of the total amount of chemical entities of formula I in the composition are chemical entities of formula I.b.2.ii:

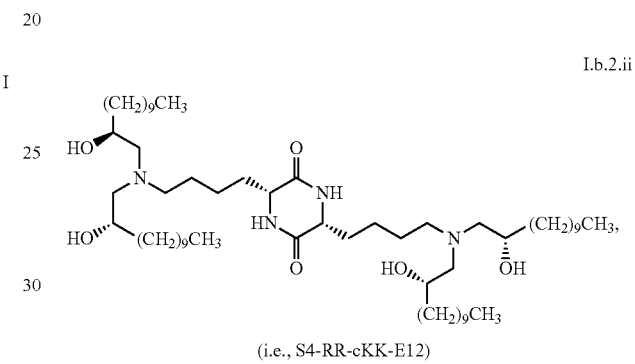

I.b.2.ii (i.e., S4-RR-cKK-E12)

wherein the third threshold amount is 50%.

In some embodiments, the second threshold amount is 50%, 60%, 70%, 80%, 85%, 90%, 91%, 92%, 93%, 94%, 95%, 96%, 97%, 98% or 99%. In some embodiments, the second threshold amount is 50%. In some embodiments, the second threshold amount is 70%. In some embodiments, the second threshold amount is 80%. In some embodiments, the second threshold amount is 95%.

Liposomes for the Delivery of Agents, Such as mRNA

Among other things, the present invention provides composition comprising a lipid compound described herein for delivery of therapeutic agents. In some embodiments, a composition provided is a lipid based nanoparticle, such as a liposome. As used herein, the term "liposome" refers to any lamellar, multilamellar, or solid lipid nanoparticle vesicle. Typically, a liposome as used herein can be formed by mixing one or more lipids or by mixing one or more lipids and polymer(s). Thus, the term "liposome" as used herein encompasses both lipid and polymer based nanoparticles. In particular, a liposome according to the present invention incorporates a lipid compound described herein as a cationic lipid component. As a non-limiting example, a liposome according to the present invention includes a composition comprising one or more chemical entities of formula I. A suitable liposome may also contain second or additional cationic lipids, helper lipids (e.g., non-cationic lipids and/or cholesterol-based lipids), PEG-modified lipids, and/or polymers.

In some embodiments, cationic lipid(s) (e.g., the composition comprising one or more chemical entities of formula I) constitute(s) about 30-50% (e.g., about 30-45%, about 30-40%, about 35-50%, about 35-45%, or about 35-40%) of the liposome by molar ratio. In some embodiments, the cationic lipid (e.g., the composition comprising one or more chemical entities of formula I) constitutes about 30%, about 35%, about 40%, about 45%, or about 50% of the liposome by molar ratio. In some embodiments, the liposome comprises a second lipid or additional cationic lipids.

Second or Additional Cationic Lipids

In some embodiments, liposomes may comprise a second or additional cationic lipid. As used herein, the phrase "cationic lipid" refers to any of a number of lipid species that have a net positive charge at a selected pH, such as physiological pH. Several cationic lipids have been described in the literature, many of which are commercially available. Particularly suitable cationic lipids for use in the compositions and methods of the invention include those described in international patent publications WO 2010/053572 (and particularly, C12-200 described at paragraph [00225]), WO 2012/170930 and WO 2013063468 each of which is incorporated herein by reference in its entirety. In certain embodiments, the compositions and methods of the invention employ a lipid nanoparticles comprising an ionizable cationic lipid described in International Patent Application No. PCT/US2013/034602, filed Mar. 29, 2013, Publ. No. WO 2013/149140 (incorporated herein by reference), such as, e.g., (15Z,18Z)—N,N-dimethyl-6-(9Z,12Z)-octadeca-9,12-dien-1-yl)tetracosa-15,18-dien-1-amine (HGT5000), (15Z, 18Z)—N,N-dimethyl-6-((9Z,12Z)-octadeca-9,12-dien-1-yl)tetracosa-4,15,18-trien-1-amine (HGT5001), and (15Z, 18Z)—N,N-dimethyl-6-((9Z,12Z)-octadeca-9,12-dien-1-yl)tetracosa-5,15,18-trien-1-amine (HGT5002).

In some embodiments, the second or additional cationic lipid N-[1-(2,3-dioleyloxy)propyl]-N,N,N-trimethylammonium chloride or "DOTMA" is used. (Feigner et al. (Proc. Nat'l Acad. Sci. 84, 7413 (1987); U.S. Pat. No. 4,897,355). DOTMA can be formulated alone or can be combined with the neutral lipid, dioleoylphosphatidyl-ethanolamine or "DOPE" or other cationic or non-cationic lipids into a liposomal transfer vehicle or a lipid nanoparticle, and such liposomes can be used to enhance the delivery of nucleic acids into target cells. Other suitable cationic lipids include, for example, 5-carboxyspermylglycinedioctadecylamide or "DOGS," 2,3-dioleyloxy-N-[2(spermine-carboxamido) ethyl]-N,N-dimethyl-1-propanaminium or "DOSPA" (Behr et al. Proc. Nat.'l Acad. Sci. 86, 6982 (1989); U.S. Pat. Nos. 5,171,678; 5,334,761), 1,2-Dioleoyl-3-Dimethylammonium-Propane or "DODAP", 1,2-Dioleoyl-3-Trimethylammonium-Propane or "DOTAP". Additional exemplary cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethylammonium chloride or "DODAC", N,N-distearyl-N,N-dimethyl-arnrnonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis,cis-9,12-octadecadienoxy)propane or "CLinDMA", 2-[5'-(cholest-5-en-3-beta-oxy)-3'-oxapentoxy)-3-dimethy 1-1-(cis,cis-9',1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[1,3]-dioxolane or "DLin- -DMA", 2,2-dilinoleyl-4-dimethylaminoethyl-[1,3]-dioxolane or "DLin-K-XTC2-DMA", and 2-(2,2-di((9Z,12Z)-octadeca-9,12-dien-1-yl)-1,3-dioxolan-4-yl)-N,N-dimethylethanamine (DLin-KC2-DMA)) (See, WO 2010/042877; Semple et al., Nature Biotech. 28: 172-176 (2010)), or mixtures thereof. (Heyes, J., et al., J Controlled Release 107: 276-287 (2005); Morrissey, D V., et al., Nat. Biotechnol. 23(8): 1003-1007 (2005); PCT Publication WO2005/121348A1). In some embodiments, one or more of the cationic lipids comprise at least one of an imidazole, dialkylamino, or guanidinium moiety.

In some embodiments, the second or additional cationic lipid may be chosen from XTC (2,2-Dilinoleyl-4-dimethylaminoethyl-[1,3]-dioxolane), MC3 (((6Z,9Z,28Z,31Z)-heptatriaconta-6,9,28,31-tetraen-19-yl 4-(dimethylamino)butanoate), ALNY-100 ((3aR,5s,6aS)—N,N-dimethyl-2,2-di ((9Z,12Z)-octadeca-9,12-dienyl)tetrahydro-3aH-cyclopenta [d][1,3]dioxol-5-amine)), NC98-5 (4,7,13-tris(3-oxo-3-(undecylamino)propyl)-N1,N16-diundecyl-4,7,10,13-tetraazahexadecane-1,16-diamide), DODAP (1,2-dioleyl-3-dimethylammonium propane), HGT4003 (WO 2012/170889, the teachings of which are incorporated herein by reference in their entirety), ICE (WO 2011/068810, the teachings of which are incorporated herein by reference in their entirety), HGT5000 (international patent publication WO/2013/149140, the teachings of which are incorporated herein by reference in their entirety) or HGT5001 (cis or trans) (WO/2013/149140), aminoalcohol lipidoids such as those disclosed in WO2010/053572, DOTAP (1,2-dioleyl-3-trimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" J. Contr. Rel. 2005, 107, 276-287), DLin-KC2-DMA (Semple, S. C. et al. "Rational Design of Cationic Lipids for siRNA Delivery" Nature Biotech. 2010, 28, 172-176), C12-200 (Love, K. T. et al. "Lipid-like materials for low-dose in vivo gene silencing" PNAS 2010, 107, 1864-1869).

Non-Cationic/Helper Lipids

In some embodiments, provided liposomes contain one or more non-cationic ("helper") lipids. As used herein, the phrase "non-cationic lipid" refers to any neutral, zwitterionic or anionic lipid. As used herein, the phrase "anionic lipid" refers to any of a number of lipid species that carry a net negative charge at a selected H, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), or a mixture thereof.

In some embodiments, such non-cationic lipids may be used alone, but are preferably used in combination with other excipients, for example, cationic lipids. In some embodiments, the non-cationic lipid may comprise a molar ratio of about 5% to about 90%, or about 10% to about 70% of the total lipid present in a liposome. In some embodiments, a non-cationic lipid is a neutral lipid, i.e., a lipid that does not carry a net charge in the conditions under which the composition is formulated and/or administered. In some embodiments, the percentage of non-cationic lipid in a liposome may be greater than 5%, greater than 10%, greater than 20%, greater than 30%, or greater than 40%.

Cholesterol-Based Lipids

In some embodiments, provided liposomes comprise one or more cholesterol-based lipids. For example, suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE. In some embodiments, the cholesterol-based lipid may comprise a molar ration of about 2% to about 30%, or about 5% to about 20% of the total lipid present in a liposome. In some embodiments, The percentage of cholesterol-based lipid in the lipid nanoparticle may be greater than 5, %, 10%, greater than 20%, greater than 30%, or greater than 40%.

PEGylated Lipids

In some embodiments, provided liposomes comprise one or more PEGylated lipids. For example, the use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention in combination with one or more of the cationic and, in some embodiments, other lipids together which comprise the liposome. Contemplated PEG-modified lipids include, but are not limited to, a polyethylene glycol chain of up to 5 kDa in length covalently attached to a lipid with alkyl chain(s) of $C_6$-$C_{20}$ length. In some embodiments, a PEG-modified or PEGylated lipid is PEGylated cholesterol or PEG-2K. The addition of such components may prevent complex aggregation and may also provide a means for increasing circulation lifetime and increasing the delivery of the lipid-nucleic acid composition to the target cell, (Klibanov et al. (1990) FEBS Letters, 268 (1): 235-237), or they may be selected to rapidly exchange out of the formulation in vivo (see U.S. Pat. No. 5,885,613).

In some embodiments, particularly useful exchangeable lipids are PEG-ceramides having shorter acyl chains (e.g., $C_{14}$ or $C_{18}$). The PEG-modified phospholipid and derivitized lipids of the present invention may comprise a molar ratio from about 0% to about 15%, about 0.5% to about 15%, about 1% to about 15%, about 4% to about 10%, or about 2% of the total lipid present in the liposome.

According to various embodiments, the selection of second or additional cationic lipids, non-cationic lipids and/or PEG-modified lipids which comprise the lipid nanoparticle, as well as the relative molar ratio of such lipids to each other, is based upon the characteristics of the selected lipid(s), the nature of the intended target cells, the characteristics of the mRNA to be delivered. Additional considerations include, for example, the saturation of the alkyl chain, as well as the size, charge, pH, pKa, fusogenicity and toxicity of the selected lipid(s). Thus the molar ratios may be adjusted accordingly. In some embodiments, the percentage of PEG-modified lipid in a liposome may be greater than 1%, greater than 2%, greater than 5%, greater than 10%, or greater than 15%.

Polymers

In some embodiments, a suitable liposome according to the present invention further includes a polymer, in combination with one or more cationic lipids as described and, in some embodiments, other carriers including various lipids described herein. Thus, in some embodiments, liposomal delivery vehicles, as used herein, also encompass polymer containing nanoparticles. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDA, e.g., 25 kDa branched PEI (Sigma #408727).

Therapeutic Agents

The present invention may be used to delivery any therapeutic agents. Specifically, any therapeutic agents to be administered to a subject may be delivered using the complexes, picoparticles, nanoparticles, microparticles, micelles, or liposomes, described herein. The agent may be an organic molecule (e.g., a therapeutic agent, a drug), inorganic molecule, nucleic acid, protein, amino acid, peptide, polypeptide, polynucleotide, targeting agent, isotopically labeled organic or inorganic molecule, vaccine, immunological agent, etc. In certain embodiments of the present invention, the agent to be delivered may be a mixture of agents.

In certain embodiments, the therapeutic agents are organic molecules with pharmaceutical activity, e.g., a drug. In certain embodiments, the drug is an antibiotic, anti-viral agent, anesthetic, steroidal agent, anti-inflammatory agent, anti-neoplastic agent, anti-cancer agent, antigen, vaccine, antibody, decongestant, antihypertensive, sedative, birth control agent, progestational agent, anti-cholinergic, analgesic, anti-depressant, anti-psychotic, I3-adrenergic blocking agent, diuretic, cardiovascular active agent, vasoactive agent, non-steroidal anti-inflammatory agent, nutritional agent, etc.

Diagnostic agents include gases; metals; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodinebased materials.

Therapeutic and prophylactic agents include, but are not limited to, antibiotics, nutritional supplements, and vaccines. Vaccines may comprise isolated proteins or peptides, inactivated organisms and viruses, dead organisms and viruses, genetically altered organisms or viruses, and cell extracts.

Polynucleotides

The present invention may be used to deliver any polynucleotide. In certain embodiments, the polynucleotide is an interfering RNA (RNAi). The phenomenon of RNAi is discussed in greater detail, for example, in the following references: Elbashir et al., 2001, *Genes Dev.*, 15:188; Fire et al., 1998, *Nature*, 391:806; Tabara et al., 1999, *Cell*, 99:123; Hammond et al., *Nature*, 2000, 404:293; Zamore et al., 2000, *Cell*, 101:25; Chakraborty, 2007, *Curr. Drug Targets*, 8:469; and Morris and Rossi, 2006, *Gene Ther.*, 13:553. In certain embodiments, the polynucleotide is a dsRNA (double-stranded RNA). In certain embodiments, the polynucleotide is an siRNA (short interfering RNA). In certain embodiments, the polynucleotide is an shRNA (short hairpin RNA). In certain embodiments, the polynucleotide is an miRNA (micro RNA). Micro RNAs (miRNAs) are genomically encoded non-coding RNAs of about 21-23 nucleotides in length that help regulate gene expression, particularly during development. See, e.g., Bartel, 2004, *Cell,* 116:281; Novina and Sharp, 2004, *Nature,* 430:161; and U.S. Patent Publication 2005/0059005; also reviewed in Wang and Li, 2007, *Front. Biosci.,* 12:3975; and Zhao, 2007, *Trends Biochem. Sci.,* 32:189. In certain embodiments, the polynucleotide is an antisense RNA.

In certain embodiments, the polynucleotide may be provided as an antisense agent or RNA interference (RNAi). See, e.g., Fire et al., *Nature* 391:806-811, 1998. Antisense therapy is meant to include, e.g., administration or in situ provision of single- or double-stranded oligonucleotides or their derivatives which specifically hybridize, e.g., bind, under cellular conditions, with cellular mRNA and/or genomic DNA, or mutants thereof, so as to inhibit expression of the encoded protein, e.g., by inhibiting transcription and/or translation. See, e.g., Crooke "Molecular mechanisms of action of antisense drugs" *Biochim. Biophys. Acta* 1489(1):31-44, 1999; Crooke "Evaluating the mechanism of action of antiproliferative antisense drugs" *Antisense Nucleic Acid Drug Dev.* 10(2):123-126, discussion 127, 2000; Methods in Enzymology volumes 313-314, 1999. The binding may be by conventional base pair complementarity, or, for example, in the case of binding to DNA duplexes, through specific interactions in the major groove of the double helix (i.e., triple helix formation). See, e.g., Chan et al., *J. Mol. Med.* 75(4):267-282, 1997.

In some embodiments, dsRNA, siRNA, shRNA, miRNA, antisense RNA, and/or RNAi can be designed and/or predicted using one or more of a large number of available algorithms. To give but a few examples, the following resources can be utilized to design and/or predict polynucleotides: algorithms found at Alnylum Online, Dharmacon Online, OligoEngine Online, Molecula Online, Ambion Online, BioPredsi Online, RNAi Web Online, Chang Bioscience Online, Invitrogen Online, LentiWeb Online GenScript Online, Protocol Online; Reynolds et al., 2004, *Nat. Biotechnol.,* 22:326; Naito et al., 2006, *Nucleic Acids Res.,* 34:W448; Li et al., 2007, *RNA,* 13:1765; Yiu et al., 2005, *Bioinformatics,* 21:144; and Jia et al., 2006, *BMC Bioinformatics,* 7: 271.

The polynucleotides may be of any size or sequence, and they may be single- or double-stranded. In certain embodiments, the polynucleotide is greater than 100 base pairs long. In certain embodiments, the polynucleotide is greater than 1000 base pairs long and may be greater than 10,000 base pairs long. The polynucleotide may be provided by any means known in the art. In certain embodiments, the polynucleotide has been engineered using recombinant techniques. See, e.g., Ausubel et al., *Current Protocols in Molecular Biology* (John Wiley & Sons, Inc., New York, 1999); *Molecular Cloning: A Laboratory Manual,* 2nd Ed., ed. by Sambrook, Fritsch, and Maniatis (Cold Spring Harbor Laboratory Press: 1989). The polynucleotide may also be obtained from natural sources and purified from contaminating components found normally in nature. The polynucleotide may also be chemically synthesized in a laboratory. In certain embodiments, the polynucleotide is synthesized using standard solid phase chemistry.

The polynucleotide may be modified by chemical or biological means. In certain embodiments, these modifications lead to increased stability of the polynucleotide. Modifications include methylation, phosphorylation, end-capping, etc.

mRNA

The present invention can be used to deliver any mRNA. mRNA is typically thought of as the type of RNA that carries information from DNA to the ribosome. The existence of mRNA is usually very brief and includes processing and translation, followed by degradation. Typically, in eukaryotic organisms, mRNA processing comprises the addition of a "cap" on the N-terminal (5') end, and a "tail" on the C-terminal (3') end. A typical cap is a 7-methylguanosine cap, which is a guanosine that is linked through a 5'-5'-triphosphate bond to the first transcribed nucleotide. The presence of the cap is important in providing resistance to nucleases found in most eukaryotic cells. The tail is typically a polyadenylation event whereby a polyadenylyl moiety is added to the 3' end of the mRNA molecule. The presence of this "tail" serves to protect the mRNA from exonuclease degradation. Messenger RNA typically is translated by the ribosomes into a series of amino acids that make up a protein.

Any mRNA capable of being translated into one or more peptides (e.g., proteins) or peptide fragments is contemplated as within the scope of the present invention. In some embodiments, an mRNA encodes one or more naturally occurring peptides. In some embodiments, an mRNA encodes one or more modified or non-natural peptides.

In some embodiments an mRNA encodes an intracellular protein. In some embodiments, an mRNA encodes a cytosolic protein. In some embodiments, an mRNA encodes a protein associated with the actin cytoskeleton. In some embodiments, an mRNA encodes a protein associated with the plasma membrane. In some specific embodiments, an mRNA encodes a transmembrane protein. In some specific embodiments an mRNA encodes an ion channel protein. In some embodiments, an mRNA encodes a perinuclear protein. In some embodiments, an mRNA encodes a nuclear protein. In some specific embodiments, an mRNA encodes a transcription factor. In some embodiments, an mRNA encodes a chaperone protein. In some embodiments, an mRNA encodes an intracellular enzyme (e.g., mRNA encoding an enzyme associated with urea cycle or lysosomal storage metabolic disorders). In some embodiments, an mRNA encodes a protein involved in cellular metabolism, DNA repair, transcription and/or translation. In some embodiments, an mRNA encodes an extracellular protein. In some embodiments, an mRNA encodes a protein associated with the extracellular matrix. In some embodiments an mRNA encodes a secreted protein. In specific embodiments, an mRNA used in the composition and methods of the invention may be used to express functional proteins or enzymes that are excreted or secreted by one or more target cells into the surrounding extracellular fluid (e.g., mRNA encoding hormones and/or neurotransmitters).

Synthesis of mRNA mRNAs according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application.

In some embodiments, for the preparation of mRNA according to the invention, a DNA template is transcribed in vitro. A suitable DNA template typically has a promoter, for example a T3, T7 or SP6 promoter, for in vitro transcription, followed by desired nucleotide sequence for desired mRNA and a termination signal.

Desired mRNA sequence(s) according to the invention may be determined and incorporated into a DNA template using standard methods. For example, starting from a desired amino acid sequence (e.g., an enzyme sequence), a virtual reverse translation is carried out based on the degenerated genetic code. Optimization algorithms may then be used for selection of suitable codons. Typically, the G/C content can be optimized to achieve the highest possible G/C content on one hand, taking into the best possible account the frequency of the tRNAs according to codon usage on the other hand. The optimized RNA sequence can be established and displayed, for example, with the aid of an appropriate display device and compared with the original (wild-type) sequence. A secondary structure can also be analyzed to calculate stabilizing and destabilizing properties or, respectively, regions of the RNA.

Modified mRNA

In some embodiments, mRNA according to the present invention may be synthesized as unmodified or modified mRNA. Typically, mRNAs are modified to enhance stability. Modifications of mRNA can include, for example, modifications of the nucleotides of the RNA. An modified mRNA according to the invention can thus include, for example, backbone modifications, sugar modifications or base modifications. In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxy-methylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, β-D-mannosyl-queosine, wybutosine, and phosphoramidates, phosphorothioates, peptide nucleotides, methylphosphonates, 7-deazaguanosine, 5-methylcytosine and inosine. The preparation of such analogues is known to a person skilled in the art e.g. from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosures of which are incorporated by reference in their entirety.

In some embodiments, mRNAs (e.g., enzyme encoding mRNAs) may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g. cytidine 5'-O-(1-thiophosphate)), boranophosphates, positively charged guanidinium groups etc., which means by replacing the phosphodiester linkage by other anionic, cationic or neutral groups.

In some embodiments, mRNAs (e.g., enzyme encoding mRNAs) may contain sugar modifications. A typical sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-ara-cytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate).

In some embodiments, mRNAs (e.g., enzyme encoding mRNAs) may contain modifications of the bases of the nucleotides (base modifications). A modified nucleotide which contains a base modification is also called a base-modified nucleotide. Examples of such base-modified nucleotides include, but are not limited to, 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallyl-cytidine 5'-triphosphate, 5-aminoallyl-uridine 5'-triphosphate, 5-bromocytidine 5'-triphosphate, 5-bromouridine 5'-triphosphate, 5-iodo-cytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, O6-methylguanosine 5'-triphosphate, pseudouridine 5'-triphosphate, puromycin 5'-triphosphate or xanthosine 5'-triphosphate.

Cap Structure

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

Thus, in some embodiments, mRNAs (e.g., enzyme encoding mRNAs) include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G (5')ppp(5')A and G(5')ppp(5')G.

In some embodiments, naturally occurring cap structures comprise a 7-methyl guanosine that is linked via a triphosphate bridge to the 5'-end of the first transcribed nucleotide, resulting in a dinucleotide cap of $m^7G(5')ppp(5')N$, where N is any nucleoside. In vivo, the cap is added enzymatically. The cap is added in the nucleus and is catalyzed by the enzyme guanylyl transferase. The addition of the cap to the 5' terminal end of RNA occurs immediately after initiation of transcription. The terminal nucleoside is typically a guanosine, and is in the reverse orientation to all the other nucleotides, i.e., G(5')ppp(5')GpNpNp.

A common cap for mRNA produced by in vitro transcription is $m^7G(5')ppp(5')G$, which has been used as the dinucleotide cap in transcription with T7 or SP6 RNA polymerase in vitro to obtain RNAs having a cap structure in their 5'-termini. The prevailing method for the in vitro synthesis of capped mRNA employs a pre-formed dinucleotide of the form $m^7G(5')ppp(5')G$ ("$m^7GpppG$") as an initiator of transcription.

To date, a usual form of a synthetic dinucleotide cap used in in vitro translation experiments is the Anti-Reverse Cap Analog ("ARCA") or modified ARCA, which is generally a modified cap analog in which the 2' or 3' OH group is replaced with —$OCH_3$.

Additional cap analogs include, but are not limited to, chemical structures selected from the group consisting of $m^7GpppG$, $m^7GpppA$, $m^7GpppC$; unmethylated cap analogs (e.g., GpppG); dimethylated cap analog (e.g., $m^{2,7}GpppG$), trimethylated cap analog (e.g., $m^{2,2,7}GpppG$), symmetrical cap analogs (e.g., $m^7Gpppm^7G$), or anti reverse cap analogs (e.g., ARCA; $m^{7,2'Ome}GpppG$, $m^{7,2'd}GpppG$, $m^{7,2'Ome}GpppG$, $m^{7,3'd}GpppG$ and their tetraphosphate derivatives) (see, e.g., Jemielity, J. et al., "Novel 'anti-reverse' cap analogs with superior translational properties", RNA, 9: 1108-1122 (2003)).

In some embodiments, a suitable cap is a 7-methyl guanylate ("$m^7G$") linked via a triphosphate bridge to the 5'-end of the first transcribed nucleotide, resulting in $m^7G$(5')ppp(5')N, where N is any nucleoside. A preferred embodiment of a $m^7G$ cap utilized in embodiments of the invention is $m^7G(5')ppp(5')G$.

In some embodiments, the cap is a Cap0 structure. Cap0 structures lack a 2'-O-methyl residue of the ribose attached to bases 1 and 2. In some embodiments, the cap is a Cap1 structure. Cap1 structures have a 2'-O-methyl residue at base 2. In some embodiments, the cap is a Cap2 structure. Cap2 structures have a 2'-O-methyl residue attached to both bases 2 and 3.

A variety of $m^7G$ cap analogs are known in the art, many of which are commercially available. These include the $m^7GpppG$ described above, as well as the ARCA 3'-OCH3 and 2'-OCH3 cap analogs (Jemielity, J. et al., RNA, 9: 1108-1122 (2003)). Additional cap analogs for use in embodiments of the invention include N7-benzylated dinucleoside tetraphosphate analogs (described in Grudzien, E. et al., RNA, 10: 1479-1487 (2004)), phosphorothioate cap analogs (described in Grudzien-Nogalska, E., et al., RNA, 13: 1745-1755 (2007)), and cap analogs (including biotinylated cap analogs) described in U.S. Pat. Nos. 8,093,367 and 8,304,529, incorporated by reference herein.

Tail Structure

Typically, the presence of a "tail" serves to protect the mRNA from exonuclease degradation. The poly A tail is thought to stabilize natural messengers and synthetic sense RNA. Therefore, in certain embodiments a long poly A tail can be added to an mRNA molecule thus rendering the RNA more stable. Poly A tails can be added using a variety of art-recognized techniques. For example, long poly A tails can be added to synthetic or in vitro transcribed RNA using poly A polymerase (Yokoe, et al. Nature Biotechnology. 1996; 14: 1252-1256). A transcription vector can also encode long poly A tails. In addition, poly A tails can be added by transcription directly from PCR products. Poly A may also be ligated to the 3' end of a sense RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)).

In some embodiments, mRNAs (e.g., enzyme encoding mRNAs) include a 3' poly(A) tail structure. Typically, the length of the poly A tail can be at least about 10, 50, 100, 200, 300, 400 at least 500 nucleotides (SEQ ID NO: 1). In some embodiments, a poly-A tail on the 3' terminus of mRNA typically includes about 10 to 300 adenosine nucleotides (e.g., about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). In some embodiments, mRNAs include a 3' poly(C) tail structure. A suitable poly-C tail on the 3' terminus of mRNA typically include about 10 to 200 cytosine nucleotides (SEQ ID NO: 2) (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, the length of the poly A or poly C tail is adjusted to control the stability of a modified sense mRNA molecule of the invention and, thus, the transcription of protein. For example, since the length of the poly A tail can influence the half-life of a sense mRNA molecule, the length of the poly A tail can be adjusted to modify the level of resistance of the mRNA to nucleases and thereby control the time course of polynucleotide expression and/or polypeptide production in a target cell.

5' and 3' Untranslated Region

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Exemplary 3' and/or 5' UTR sequences can be derived from mRNA molecules which are stable (e.g., globin, actin, GAPDH, tubulin, histone, or citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

According to various embodiments, any size mRNA may be encapsulated by provided liposomes. In some embodiments, the provided liposomes may encapsulate mRNA of greater than about 0.5 kb, 1 kb, 1.5 kb, 2 kb, 2.5 kb, 3 kb, 3.5 kb, 4 kb, 4.5 kb, or 5 kb in length.

Liposomes

The liposomes for use in provided compositions can be prepared by various techniques which are presently known in the art. For example, multilamellar vesicles (MLV) may be prepared according to conventional techniques, such as by depositing a selected lipid on the inside wall of a suitable container or vessel by dissolving the lipid in an appropriate solvent, and then evaporating the solvent to leave a thin film on the inside of the vessel or by spray drying. An aqueous phase may then added to the vessel with a vortexing motion which results in the formation of MLVs. Uni-lamellar vesicles (ULV) can then be formed by homogenization, sonication or extrusion of the multi-lamellar vesicles. In addition, unilamellar vesicles can be formed by detergent removal techniques.

In certain embodiments, provided compositions comprise a liposome wherein an agent, such as a nucleic acid e.g., mRNA, is associated on both the surface of the liposome and encapsulated within the same liposome. For example, during preparation of the compositions of the present invention, cationic liposomes may associate with the mRNA through electrostatic interactions. For example, during preparation of the compositions of the present invention, cationic liposomes may associate with the mRNA through electrostatic interactions.

In some embodiments, the compositions and methods of the invention comprise mRNA encapsulated in a liposome. In some embodiments, the one or more mRNA species may be encapsulated in the same liposome. In some embodiments, the one or more mRNA species may be encapsulated in different liposomes. In some embodiments, the mRNA is encapsulated in one or more liposomes, which differ in their lipid composition, molar ratio of lipid components, size, charge (Zeta potential), targeting ligands and/or combinations thereof. In some embodiments, the one or more liposome may have a different composition of cationic lipids, neutral lipid, PEG-modified lipid and/or combinations thereof. In some embodiments the one or more lipisomes may have a different molar ratio of cationic lipid, neutral lipid, cholesterol and PEG-modified lipid used to create the liposome.

The process of incorporation of a desired therapeutic agent, such as a nucleic acid (e.g., mRNA), into a liposome is often referred to as "loading". Exemplary methods are described in Lasic, et al., FEBS Lett., 312: 255-258, 1992, which is incorporated herein by reference. The liposome-incorporated nucleic acids may be completely or partially located in the interior space of the liposome, within the bilayer membrane of the liposome, or associated with the exterior surface of the liposome membrane. The incorporation of a nucleic acid into liposomes is also referred to herein as "encapsulation" wherein the nucleic acid is entirely contained within the interior space of the liposome. The purpose of incorporating a mRNA into a transfer vehicle, such as a liposome, is often to protect the nucleic acid from an environment which may contain enzymes or chemicals that degrade nucleic acids and/or systems or receptors that cause the rapid excretion of the nucleic acids. Accordingly, in some embodiments, a suitable delivery vehicle is capable of enhancing the stability of the mRNA contained therein and/or facilitate the delivery of mRNA to the target cell or tissue.

Liposome Size

Suitable liposomes in accordance with the present invention may be made in various sizes. In some embodiments, provided liposomes may be made smaller than previously known mRNA encapsulating liposomes. In some embodiments, decreased size of liposomes is associated with more efficient delivery of mRNA. Selection of an appropriate liposome size may take into consideration the site of the target cell or tissue and to some extent the application for which the liposome is being made.

In some embodiments, an appropriate size of liposome is selected to facilitate systemic distribution of antibody encoded by the mRNA. In some embodiments, it may be desirable to limit transfection of the mRNA to certain cells or tissues. For example, to target hepatocytes a liposome may be sized such that its dimensions are smaller than the fenestrations of the endothelial layer lining hepatic sinusoids in the liver; in such cases the liposome could readily penetrate such endothelial fenestrations to reach the target hepatocytes.

Alternatively or additionally, a liposome may be sized such that the dimensions of the liposome are of a sufficient diameter to limit or expressly avoid distribution into certain cells or tissues. For example, a liposome may be sized such that its dimensions are larger than the fenestrations of the endothelial layer lining hepatic sinusoids to thereby limit distribution of the liposomes to hepatocytes.

In some embodiments, a suitable liposome has a size of or less than about 500 nm, 450 nm, 400 nm, 350 nm, 300 nm, 250 nm, 200 nm, 150 nm, 125 nm, 110 nm, 100 nm, 95 nm, 90 nm, 85 nm, 80 nm, 75 nm, 70 nm, 65 nm, 60 nm, 55 nm, or 50 nm. In some embodiments, a suitable liposome has a size no greater than about 250 nm (e.g., no greater than about 225 nm, 200 nm, 175 nm, 150 nm, 125 nm, 100 nm, 75 nm, or 50 nm). In some embodiments, a suitable liposome has a size ranging from about 10-250 nm (e.g., ranging from about 10-225 nm, 10-200 nm, 10-175 nm, 10-150 nm, 10-125 nm, 10-100 nm, 10-75 nm, or 10-50 nm). In some embodiments, a suitable liposome has a size ranging from about 100-250 nm (e.g., ranging from about 100-225 nm, 100-200 nm, 100-175 nm, 100-150 nm). In some embodiments, a suitable liposome has a size ranging from about 10-100 nm (e.g., ranging from about 10-90 nm, 10-80 nm, 10-70 nm, 10-60 nm, or 10-50 nm).

A variety of alternative methods known in the art are available for sizing of a population of liposomes. One such sizing method is described in U.S. Pat. No. 4,737,323, incorporated herein by reference. Sonicating a liposome suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomes may be determined by quasi-electric light scattering (QELS) as described in Bloomfield, Ann. Rev. Biophys. Bioeng., 10:421-150 (1981), incorporated herein by reference. Average liposome diameter may be reduced by sonication of formed liposomes. Intermittent sonication cycles may be alternated with QELS assessment to guide efficient liposome synthesis.

Pharmaceutical Compositions

To facilitate delivery of an agent, such as a nucleic acid e.g., mRNA, and/or expression of mRNA in vivo, delivery vehicles such as liposomes can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition.

Provided liposomally-encapsulated agents, such as a nucleic acid e.g., mRNA and compositions containing the same, may be administered and dosed in accordance with current medical practice, taking into account the clinical condition of the subject, the site and method of administration, the scheduling of administration, the subject's age, sex, body weight and other factors relevant to clinicians of ordinary skill in the art. The "effective amount" for the purposes herein may be determined by such relevant considerations as are known to those of ordinary skill in experimental clinical research, pharmacological, clinical and medical arts. In some embodiments, the amount administered is effective to achieve at least some stabilization, improvement or elimination of symptoms and other indicators as are selected as appropriate measures of disease progress, regression or improvement by those of skill in the art. For example, a suitable amount and dosing regimen is one that causes at least transient protein (e.g., enzyme) production.

Suitable routes of administration include, for example, oral, rectal, vaginal, transmucosal, pulmonary including intratracheal or inhaled, or intestinal administration; parenteral delivery, including intradermal, transdermal (topical), intramuscular, subcutaneous, intramedullary injections, as well as intrathecal, direct intraventricular, intravenous, intraperitoneal, and/or intranasal administration.

Alternately or additionally, liposomally encapsulated agents, such as a nucleic acid e.g., mRNA and compositions of the invention may be administered in a local rather than systemic manner, for example, via injection of the pharmaceutical composition directly into a targeted tissue, preferably in a sustained release formulation. Local delivery can be affected in various ways, depending on the tissue to be targeted. For example, aerosols containing compositions of the present invention can be inhaled (for nasal, tracheal, or bronchial delivery); compositions of the present invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing provided compositions complexed with therapeutic molecules or ligands can even be surgically administered, for example in association with a polymer or other structure or substance that can allow the compositions to diffuse from the site of implantation to surrounding cells. Alternatively, they can be applied surgically without the use of polymers or supports.

In some embodiments, provided liposomes and/or compositions are formulated such that they are suitable for extended-release of the agent, e.g., mRNA contained therein. Such extended-release compositions may be conveniently administered to a subject at extended dosing intervals. For example, in one embodiment, the compositions of the present invention are administered to a subject twice day, daily or every other day. In a preferred embodiment, the compositions of the present invention are administered to a subject twice a week, once a week, every ten days, every two weeks, every three weeks, or more preferably every four weeks, once a month, every six weeks, every eight weeks, every other month, every three months, every four months, every six months, every eight months, every nine months or annually. Also contemplated are compositions and liposomes which are formulated for depot administration (e.g., intramuscularly, subcutaneously, intravitreally) to either deliver or release a mRNA over extended periods of time. Preferably, the extended-release means employed are combined with modifications made to the mRNA to enhance stability.

Also contemplated herein are lyophilized pharmaceutical compositions comprising one or more of the liposomes disclosed herein and related methods for the use of such compositions as disclosed for example, in International Patent Application No. PCT/US2012/041663, filed Jun. 8, 2012, Publ. No. WO 2012/170889, the teachings of which are incorporated herein by reference in their entirety. For example, lyophilized pharmaceutical compositions according to the invention may be reconstituted prior to administration or can be reconstituted in vivo. For example, a lyophilized pharmaceutical composition can be formulated in an appropriate dosage form (e.g., an intradermal dosage form such as a disk, rod or membrane) and administered such that the dosage form is rehydrated over time in vivo by the individual's bodily fluids.

Provided liposomes and compositions may be administered to any desired tissue. In some embodiments, the agent, e.g., mRNA delivered by provided liposomes or compositions is expressed in the tissue in which the liposomes and/or compositions were administered. In some embodiments, the mRNA delivered is expressed in a tissue different from the tissue in which the liposomes and/or compositions were administered Exemplary tissues in which delivered mRNA may be delivered and/or expressed include, but are not limited to the liver, kidney, heart, spleen, serum, brain, skeletal muscle, lymph nodes, skin, and/or cerebrospinal fluid.

According to various embodiments, the timing of expression of delivered agents, e.g., mRNAs, can be tuned to suit a particular medical need. In some embodiments, the expression of the protein encoded by delivered mRNA is detectable 1, 2, 3, 6, 12, 18, 24, 30, 36, 42, 48, 54, 60, 66, and/or 72 hours in serum or target tissues after a single administration of provided liposomes or compositions. In some embodiments, the expression of the protein encoded by the mRNA is detectable 1 day, 2 days, 3 days, 4 days, 5 days, 6 days, and/or 7 days in serum or target tissues after a single administration of provided liposomes or compositions. In some embodiments, the expression of the protein encoded by the mRNA is detectable 1 week, 2 weeks, 3 weeks, and/or 4 weeks in serum or target tissues after a single administration of provided liposomes or compositions. In some embodiments, the expression of the protein encoded by the mRNA is detectable after a month or longer after a single administration of provided liposomes or compositions.

EXAMPLES

Example 1-Synthesis of Racemic Compounds of Formula I

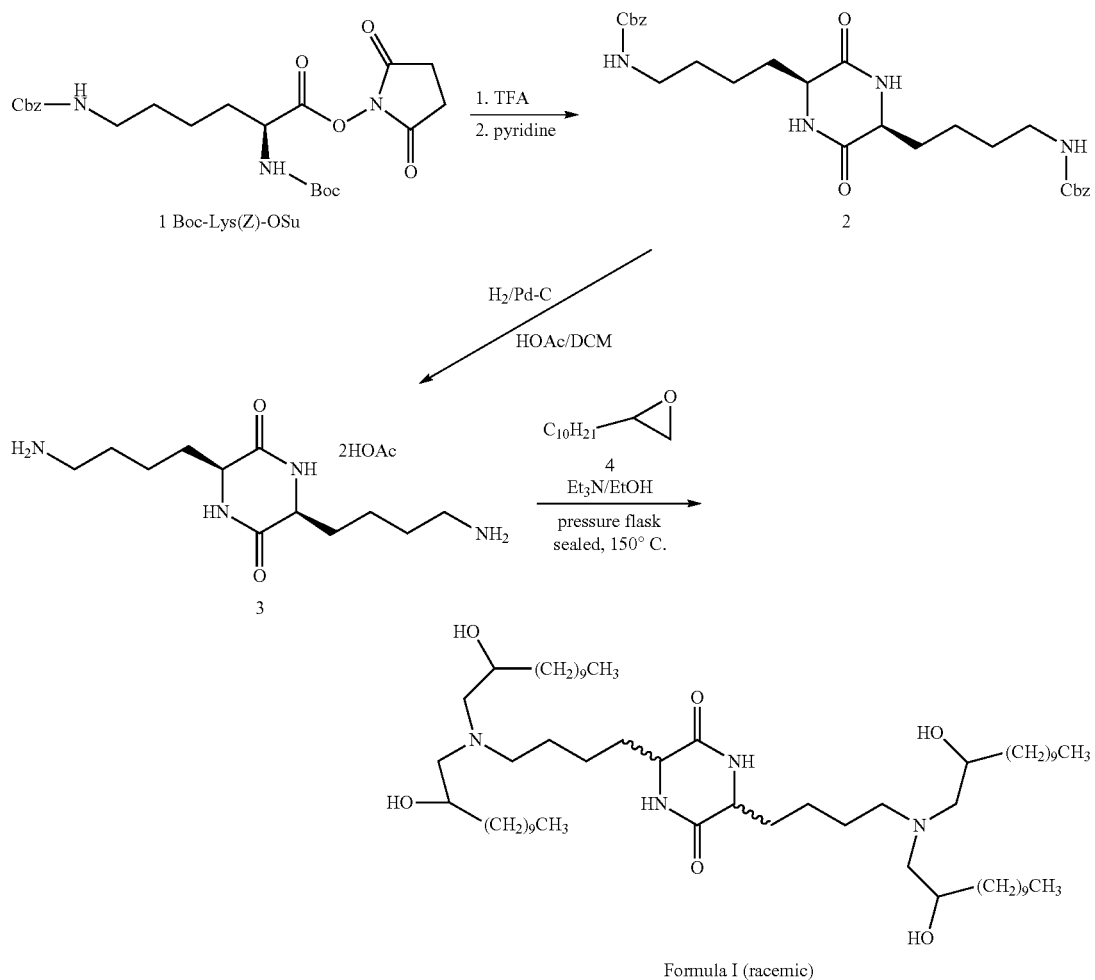

Scheme 1. Synthetic route to racemic compounds of Formula I

Racemic compound 10 was prepared from protected lysine derivative 1, Boc-Lys(Z)-OSu, by cleavage of the alpha-amino tert-butyl carbamate with trifluoroacetic acid and dimerization of the resulting free amine to form 3,6-dioxopiperazine 2. Hydrogenation of 2 over catalytic palladium yields primary diamine 3, which is treated with four equivalents of epoxide 4 and triethylamine to form the racemic 3,6-dioxopiperazine 10 of formula I.

Dibenzyl(((2S,5S)-3,6-dioxopiperazine-2,5-diyl)bis(butane-4,1-diyl))dicarbamate 2

To Boc-Lys(Z)-OSu 1 (50 g) cooled with an ice bath was added TFA (60 mL) slowly. The resulting mixture was stirred for 20 min. The ice bath was removed and stirring was continued for 1 h. TFA was removed by rotary evaporation. The oily residue was dissolved in DMF (80 mL) and added slowly to stirred pyridine (anhydrous, 2.5 L). Mass spectrometry indicated completion of reaction after 1 h. Pyridine was removed by rotary evaporation and the residue was diluted with EtOAc (2 L). After 20 min of stirring the mixture was filtered to give 2 as off-white solid (20 g after overnight vacuum drying. Yield: 73%).

(3S,6S)-3,6-bis(4-Aminobutyl)piperazine-2,5-dione—2HOAc 3

To compound 2 in a mixture of AcOH (550 mL) and DCM (550 mL) was added Pd/C (10%, wet. 10 g). This mixture was stirred under a $H_2$ balloon for 4 h when mass spectrometry indicated completion of reaction. The reaction mixture was flushed with nitrogen for 10 min and filtered through Celite. The Celite was rinsed with MeOH (3×250 mL). The combined filtrate was evaporated and the residue was stirred with EtOAc (1.0 L) for 30 min. Filtration gave 3 as white solid (16.37 g after overnight vacuum drying. Yield: 114%. $^1$H NMR shows clean product but with extra HOAc in sample)

3,6-bis(4-(bis(2-Hydroxydodecyl)amino)butyl)piperazine-2,5-dione 10

To a mixture of 3 (15.87 g, 42.2 mmol) and 4 (57 mL, 261 mmol) in EtOH (75 mL) stirred in a 500 mL pressure flask at room temperature was added Et₃N (23 mL, 165 mmol). The flask was flushed with nitrogen for 5 min and sealed. The mixture (solid and liquid slurry) was stirred for 30 min at room temperature then heated to 150-155° C. (oil bath temperature) and stirred for 5 h. A clear solution was obtained after temperature reached 150° C. After being cooled to room temperature the reaction solution was evaporated and the residue was purified by flash column chromatography 9 times with 0-30% MeOH/DCM as eluent and 2 times with 0-30% MeOH/EtOAc as eluent. Use of DCM to 50% of 75:22:3 DCM/MeOH/NH₄OH (aq.) as eluent led to co-elution of product with a less polar side product. The side product ran closely with product on TLC with 30% MeOH/DCM as developing solvents. It was well separated from product on TLC with 30% MeOH/EtOAc as developing solvents. Pure product fractions from column purifications were pooled and evaporated. The oily residue was dissolved in Et₂O and evaporated. Drying under vacuum overnight removed all solvents and gave the racemic compound 10 as light yellow gel (9.85 g, yield: 24%). HPLC with ELSD detection showed two similar sized peaks with same product mass. Elemental Analysis: (Calc): C, 72.63; H, 12.17; N, 5.64; (Obsd): C, 72.25; H, 12.37; N, 5.68. Mass Spec: 993.8 m/z.

In another run with 7.15 g of 3 and 25.6 mL of 4 the crude product was purified twice with 0-30% MeOH/EtOAc as eluent to give two batches of product: the 1.55 g batch from early fractions and the 7.38 g batch from late fractions. Both batches were pure by ¹H NMR. HPLC with ELSD detection showed two similar sized peaks with same product mass for the 7.38 g batch but only a single product peak for the 1.55 g batch.

Example 2-Synthesis of Chiral Compounds of Formula I.b.1 (i.e., Compound 10)

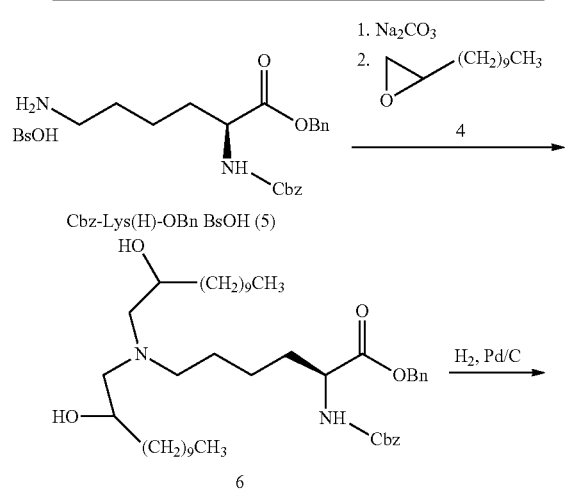

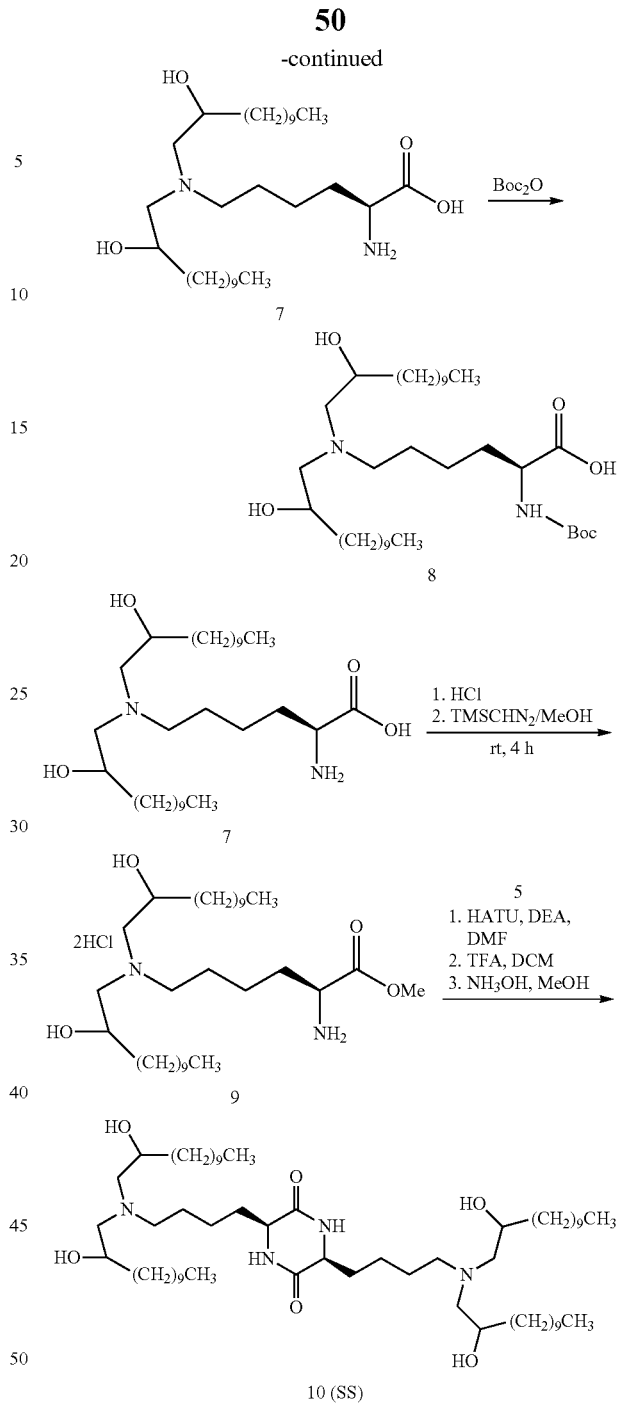

Chiral compound 10 was synthesized via N-alkylation of protected lysine derivative 5 with two equivalents of epoxide 4 to form diol 6. Hydrogenation of diol 6 over catalytic palladium forms alpha amino acid 7, which is divided into two portions. The first portion of alpha amino acid 7 has its alpha amino group protected as the tert-butyl carbamate, upon treatment with Boc anhydride, to form carboxylic acid 8. The second portion of alpha amino acid 7 has its free acid converted to the methyl ester to form amine 9. Carboxylic acid 8 and amine 9 are coupled to an amide intermediate via peptide coupling reagents such as HATU and diethanolamine in aprotic solvent such as DMF, the tert-butyl carbamate group of the amide intermediate is cleaved with trifluoroacetic acid in dichloromethane, and the resulting amino ester product is cyclized to the piperazine-2,5-dione 10. The stereochemistry at all chiral centers is preserved via this route.

Chiral compounds 12-15, below, are prepared via described synthetic routes using respective chiral epoxide starting materials.

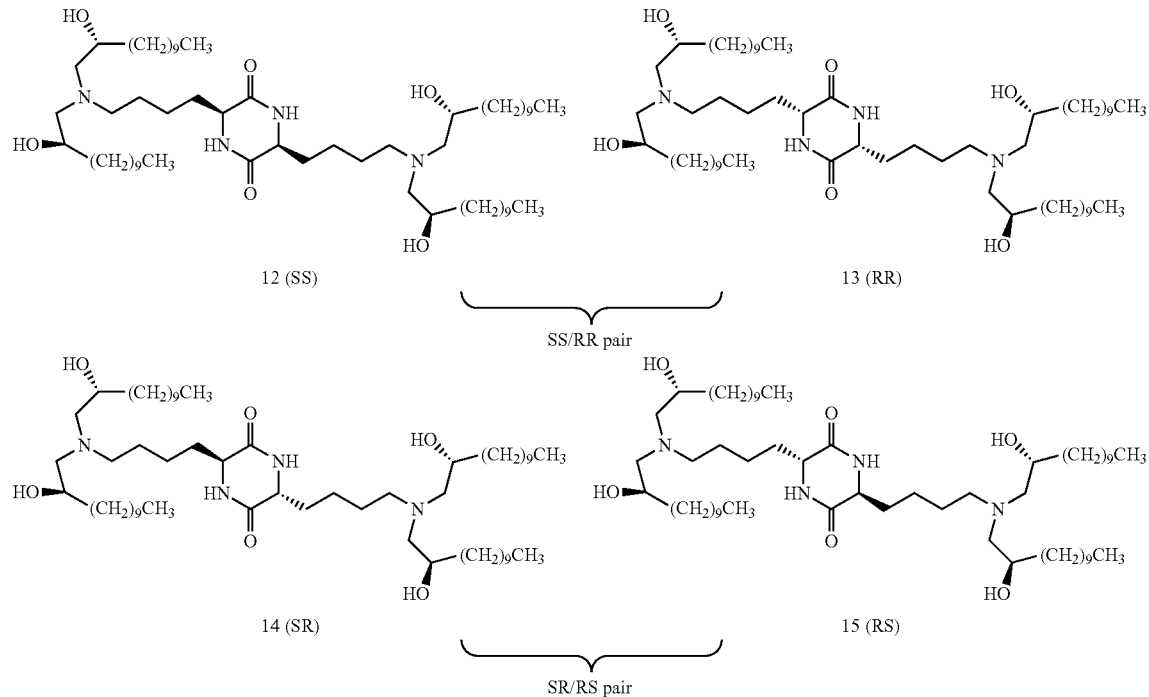

Scheme 3. Chiral compounds 12-15.

12 (SS)  13 (RR)

SS/RR pair 14 (SR)  15 (RS)

SR/RS pair

Example 3-the Compound of Formula I.a.i (i.e., R4-SR-cKK-E12)

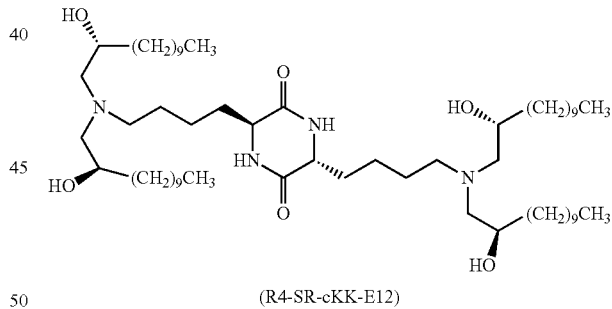

(R4-SR-cKK-E12)

Scheme 4: Synthesis of the compound of Formula I.a.i (i.e., R4-SR-cKK-E12)

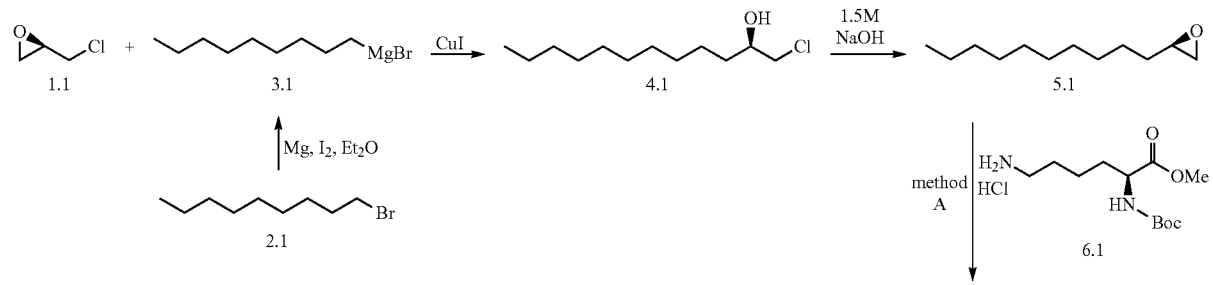

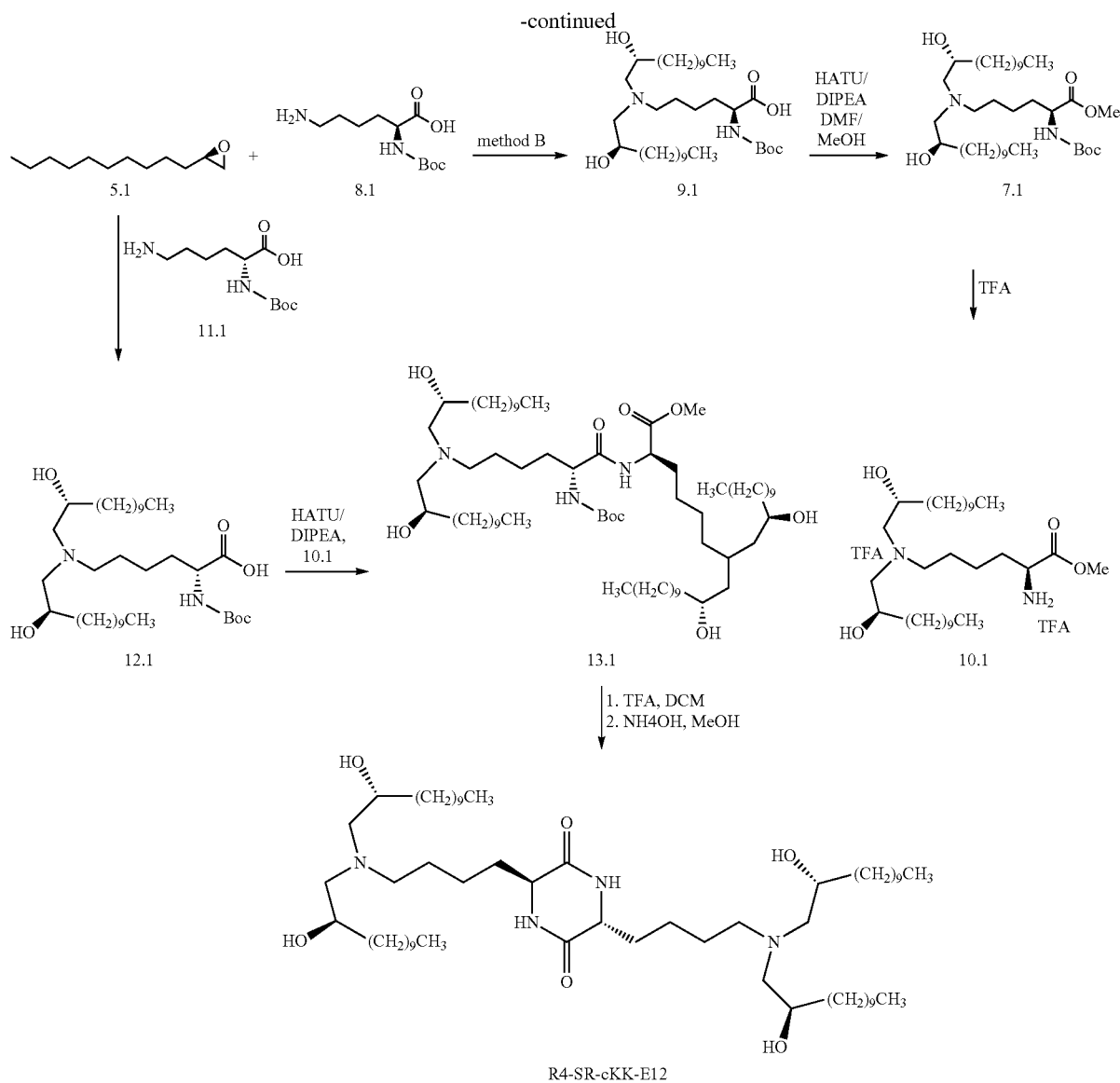

R4-SR-cKK-E12

Synthesis of Compound 3.1:

To a suspension of Mg (60 g, 2.5 mol) in anhydrous Et$_2$O (1000 mL) was added one crystal of iodine, followed by addition of 1-bromononane (25 mL). The reaction was initiated and the solution began to reflux after heating the reaction flask with a water bath. The remaining 1-bromononane (360 mL, 2.0 mol total) was added through an additional funnel in 1.5 h to maintain the reflux. After addition, the reaction solution was heated at reflux with a water bath for an additional 30 min and then it was cooled to room temperature. This ether solution of 3.1 was used directly in the next reaction.

Synthesis of Compound 4.1:

To a suspension of CuI (39 g, 0.2 mol) in anhydrous THF (1000 mL) stirred with a mechanical stirrer at −78° C. in a 5 L three-necked flask was added R-epichlorohydrin (185 g, 2.0 mol) (additional funnel). After addition, the above ether solution of 3.1 was added via a cannula in 1 h. The mixture was stirred at −78° C. for 3.5 hrs, then quenched with saturated aqueous NH$_4$Cl (1500 mL). The organic layer was separated. The aqueous layer was extracted with Et$_2$O (2000 mL). The combined organic phase was washed with brine, dried (over MgSO$_4$), and evaporated under vacuum. The crude product was purified by flash column chromatography (2.5 kg SiO$_2$, eluted with 0-10% EtOAc in Hexanes) to give 292 g of 4.1 (yield: 66%) as a light yellow oil.

Synthesis of Compound 5.1:

To a solution of 4.1 (292 g, 1.33 mol) in MeOH (600 mL) and THF (600 mL) was added aqueous NaOH (1.5M, 1000 mL) through an additional funnel at 0° C. After addition the reaction mixture was stirred at room temperature for 2.5 hrs, TLC showed a major product, very minor amount of starting material (EtOAc:Hexanes=1:9, Rf=0.6). THF and MeOH were removed by rotary evaporation under vacuum. The aqueous residue was extracted with Et$_2$O (600 mL×3). The combined organic phase was washed with brine, dried over MgSO$_4$, and evaporated. The yellow oily residue was purified by column (SiO$_2$, 2.5 kg, eluted with 0-10% EtOAc in hexanes) to afford 205 g (84%) of pure 5.1.

Synthesis of Compound 7.1:

Method A: To a solution of 6.1 (75 g, 0.25 mol) in a mixture of DCM (1000 mL) and MeOH (71 mL) that was being stirred at room temperature was added aqueous Na$_2$CO$_3$ (2.0 M, 135 mL). Organic layer was separated and the aqueous layer was extracted with DCM (250 mL×2). The combined organic phase was dried over Na$_2$SO$_4$ and evaporated under vacuum. The residue was dissolved in MeOH (375 mL), then compound 5.1 (185 g, 1.0 mol) was added. The reaction mixture was stirred at room temperature for 4 days when MS and TLC showed mostly desired product. After concentration, the crude product was purified by flash column chromatography (2.0 kg SiO$_2$, eluted with 0-60% EtOAc in hexanes) to give 7.1 (131 g, 82%) as a pale viscous oil.

Method B:

To a suspension of 8.1 (50 g, 0.2 mol) in MeOH (600 mL) was added DIPEA (45 mL), then compound 5.1 (150 g, 0.813 mol, 4.0 equiv) was added. The reaction mixture was stirred at room temperature for 7 days. Solvents were removed, the residue was purified by column (1.0 kg of SiO$_2$, eluted with 0-30% MeOH in EtOAc) to give 9.1 as a waxy solid (83 g, 67%). To a solution of 9.1 (81 g, 0.13 mol) in DMF (1000 mL) stirred at 0° C. was added HATU (50.1 g, 0.13 mol), followed by DIPEA (92 mL, 0.52 mol). The mixture was stirred at 0° C. for 40 min, and then MeOH (53.2 mL, 10.0 equiv) was added. The resulting mixture was stirred at room temperature overnight. It was then diluted with water (5000 mL) and extracted with EtOAc (500 mL×4). The combined organic phase was washed with brine (600 mL×3), dried over anhydrous MgSO$_4$ and evaporated under vacuum. The crude product was purified by column (1.0 kg of SiO$_2$, eluted with 0-80% EtOAc in hexanes) to give 7.1 (69 g, 55% for 2 steps) as a pale viscous oil.

Synthesis of Compound 10.1:

To a solution of 7.1 (69 g, 0.11 mol) in DCM (200 mL) was added TFA (200 mL), the mixture was stirred at room temperature for 2 hrs, MS detection showed only desired product. All solvents were evaporated under vacuum to give 115 g of a brown colored oil-like product 10.1, which was used in the next step without further purification.

Synthesis of Compound 12.1:

To a suspension of 11.1, Boc-D-lysine (75 g, 0.305 mol) in MeOH (900 mL) were added DIPEA (68 mL) and 5.1 (196 g, 1.06 mol). The mixture was stirred at room temperature for 7 days. Volatiles were removed and the crude product was purified by column (2.5 kg of SiO$_2$, eluted with 0-40% MeOH in EtOAc) to give 118 g (63%) of pure compound 12.1.

Synthesis of Compound 13.1:

To a solution of 12.1 (67.5 g, 0.11 mol) in DMF (600 mL, warm up to 50° C. for 30 min to obtain a homogeneous solution) that was cooled with an ice-bath were added HATU (50 g, 0.12 mol) and DIPEA (95 mL, 0.55 mol). The resulting mixture was stirred at 0° C. for 45 min, then compound 10.1 (115 g, obtained above) in DMF (400 mL) was added using an additional funnel. The mixture was stirred at room temperature overnight. Ether (1000 mL) was added, followed by water (1000 mL). The organic phase was separated; the aqueous was extracted with ether (250 mL×2). The combined organic phase was washed with water, dried over anhydrous MgSO$_4$, filtered and concentrated. The residue was purified by column (1.0 kg of SiO$_2$, eluted with 0-20% MeOH in EtOAc) to give 94.2 g (76%) of compound 13.1.

Synthesis of the Compound of Formula I.a.i (i.e., R4-SR-cKK-E12)

To a solution of 13.1 (94 g, 0.084 mol) in DCM (300 mL) was added TFA (300 mL). The mixture was stirred at room temperature for 2 hrs. MS detection showed complete reaction. Solvents were evaporated under vacuum. The residue was dissolved in DCM (500 mL) and washed with aqueous Na$_2$CO$_3$ (1.0 M, 500 mL). The aqueous wash was back extracted with DCM (100 mL). The combined organic phase was dried over anhydrous NaSO$_4$ and evaporated. The residue was dissolved in MeOH (1500 mL) and cooled with an ice-bath. Aqueous NH$_4$OH (28%, 80 mL) was added through additional funnel. The reaction mixture was allowed to slowly warm up to room temperature and stirred at ambient temperature for 2 days. Volatiles were evaporated under vacuum. The crude product was purified by column (1.0 kg of SiO$_2$, eluted with solvents: 1% NH$_4$OH, 4-9% MeOH, 95-90% EtOAc) to give 34 g of pure R4-SR-cKK-E12 and 22 g of impure R4-SR-cKK-E12. The impure R4-SR-cKK-E12 was re-purified by column to give 12 g of pure R4-SR-cKK-E12. Thus, a total 46 g (55%) of pure R4-SR-cKK-E12 (gummy solid) was obtained.

Example 4-the Compound of Formula I.a.ii (i.e., S4-SR-cKK-E12)

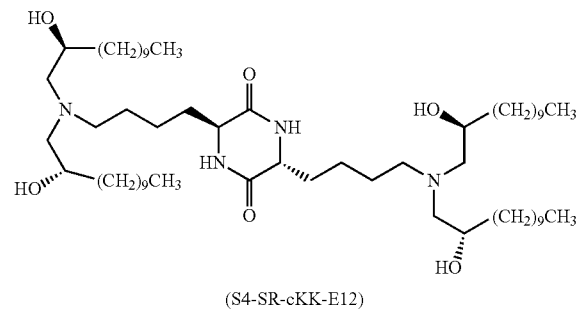

(S4-SR-cKK-E12)

Scheme 5: Synthesis of the compound of Formula I.a.ii (i.e., S4-SR-cKK-E12)

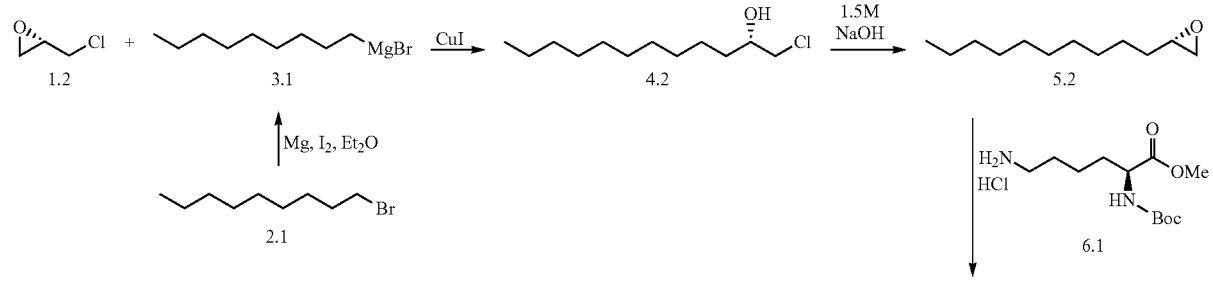

-continued

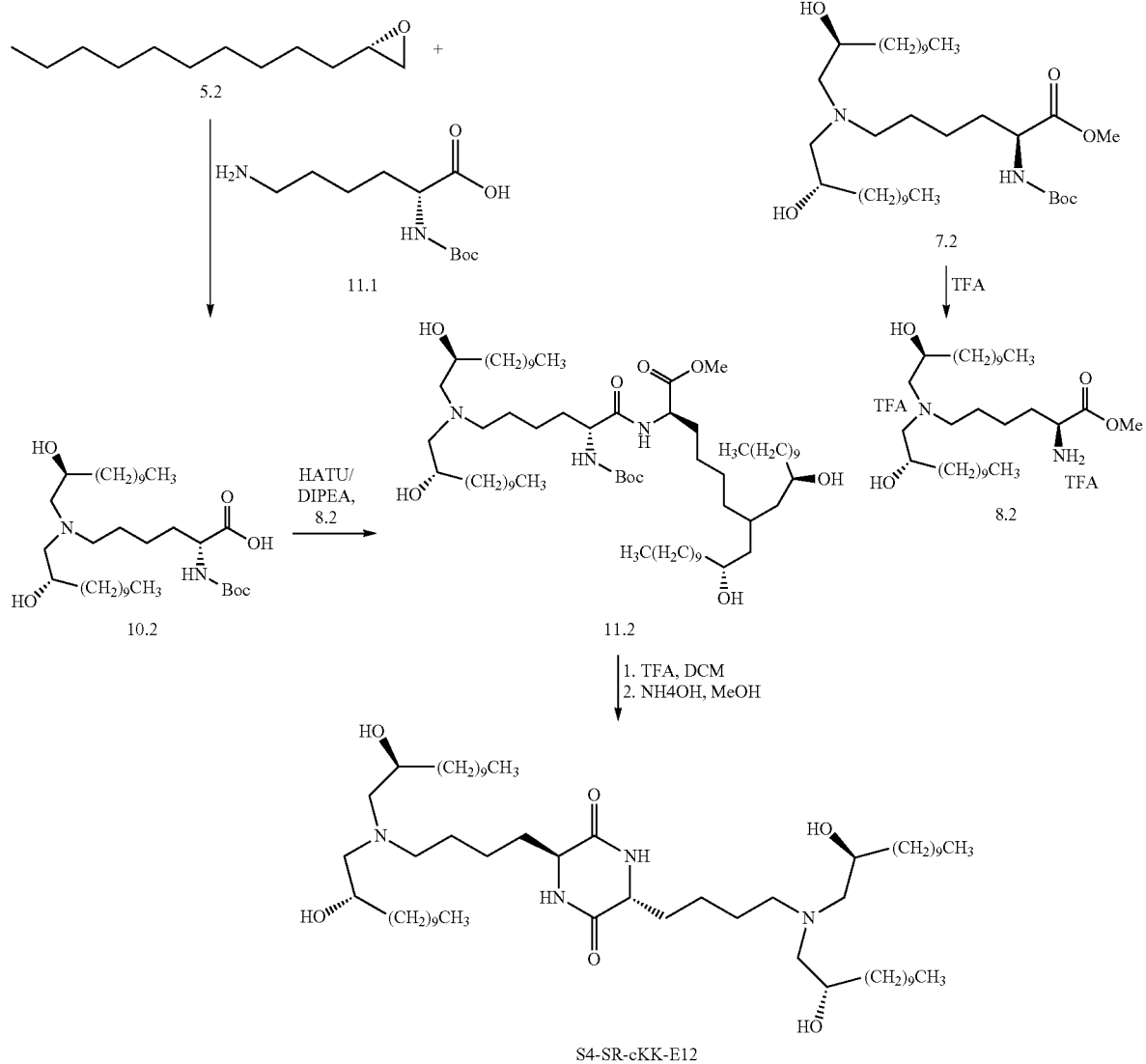

S4-SR-cKK-E12

Synthesis of Compound 3.1:

To a suspension of Mg (30 g, 1.25 mol) in anhydrous $Et_2O$ (600 mL) was added one crystal of iodine, followed by addition of 1-bromononane (30 mL). The reaction was initiated and the solution began to reflux after heating the reaction flask with a water bath. The remaining 1-bromononane (161 mL, 2.0 mol total) was added through an additional funnel in 1.5 h to maintain the reflux. After addition, the reaction solution was heated at reflux with a water bath for an additional 30 min and then it was cooled to room temperature. This ether solution of 3.1 was used directly in the next reaction.

Synthesis of Compound 4.2:

To a suspension of CuI (19 g, 0.1 mol) in anhydrous THF (1000 mL) that was being stirred with a mechanical stirrer at −78° C. in a 5 L three-necked flask was added S-epichlorohydrin (92 g, 1.0 mol) using an additional funnel. After addition, the above ether solution of 3.2 was added via a cannula in 1 h. The mixture was stirred at −78° C. for 3.5 hrs, then quenched with saturated aqueous $NH_4Cl$ (400 mL). The organic layer was separated. The aqueous layer was extracted with $Et_2O$ (1000 mL). The combined organic phase was washed with brine, dried (over $MgSO_4$), and evaporated under vacuum. The crude product was purified by flash column chromatography (2.5 kg $SiO_2$, eluted with 0-10% EtOAc in hexanes) to give 111.6 g of 4.2 (yield: 66%) as a light yellow oil.

Synthesis of Compound 5.2:

To a solution of 4.2 (111.3 g, 0.506 mol) in MeOH (230 mL) and THF (230 mL) was added aqueous NaOH (1.5M, 395 mL) using an additional funnel at 0° C. After addition the reaction mixture was stirred at room temperature for 2.5 hrs, TLC showed a major product and very minor amount of starting material (EtOAc:Hexanes=1:9, Rf=0.6). THF and MeOH were removed by rotary evaporation under vacuum. The aqueous residue was extracted with $Et_2O$ (200 mL×3). The combined organic phase was washed with brine, dried over $MgSO_4$, and evaporated. The yellow oily residue was purified by column ($SiO_2$, 1.0 kg, eluted with 0-10% EtOAc in hexanes) to afford 81 g (87%) of pure 5.2.

Synthesis of Compound 7.2:

To a solution of 6.1 (13 g, 0.044 mol) in a mixture of DCM (100 mL) and MeOH (10 mL) that was being stirred at room temperature was added aqueous $Na_2CO_3$ (2.0 M, 25 mL). Organic layer was separated and the aqueous layer was extracted with DCM (250 mL×2). The combined organic phase was dried over $Na_2SO_4$ and evaporated under vacuum. The residue was dissolved in MeOH (60 mL), then compound 5.2 (32 g, 0.174 mol) was added. The reaction mixture was stirred at room temperature for 4 days when MS and TLC showed mostly desired product. After concentration, the crude product was purified by flash column chromatography (600 g $SiO_2$, eluted with 0-60% EtOAc in hexanes) to give 7.2 (23 g, 85%) as a pale viscous oil.

Synthesis of Compound 8.2:

To a solution of 7.2 (23 g, 0.0366 mol) in DCM (60 mL) was added TFA (60 mL), the mixture was stirred at room temperature for 2 hrs, MS detection showed only desired product. All solvents were evaporated under vacuum to give 40 g of a brown colored oil-like product 8.2, which was used in the next step without further purification.

Synthesis of Compound 10.2:

To a suspension of 11.1, Boc-D-lysine (14 g, 0.057 mol) in MeOH (900 mL) were added TEA (11.6 mL) and 5.2 (42 g, 0.228 mol). The mixture was stirred at room temperature for 7 days. Volatiles were removed and the crude product was purified by column (1.0 kg of $SiO_2$, eluted with 0-40% MeOH in EtOAc) to give 24 g (70%) of pure compound 10.2.

Synthesis of Compound 11.2:

To a solution of 10.2 (9.1 g, 14.82 mmol) in DMF (120 mL) that was being cooled with an ice bath were added HATU (8.4 g, 22.23 mol) and DIPEA (25 mL, 148.2 mmol). The mixture was stirred at 0° C. for 45 min, then compound 8.2 in DMF (80 mL) was added using an additional funnel. The resulting mixture was stirred at room temperature overnight. MS detection showed no starting material. Ether (1000 mL) was added, followed by water (1000 mL). The organic phase was separated, the aqueous was extracted with ether (200 mL×2). The combined organic phase was washed with brine, dried with anhydrous $MgSO_4$, filtered and concentrated. The residue was purified by column (330 g of $SiO_2$, eluted with 0-20% MeOH in EtOAc) to give 10.6 g of desired compound 11.2.

Synthesis of the Compound of Formula I.a.ii (i.e., S4-SR-cKK-E12):

To a solution of 11.2 (10.6 g, 0.084 mol) in DCM (30 mL) was added TFA (30 mL). The mixture was stirred at room temperature for 2 hrs. MS detection showed complete reaction. Solvents were evaporated under vacuum. The residue was dissolved in DCM (150 mL) and washed with aqueous $Na_2CO_3$ (1.0 M, 200 mL). The aqueous wash was back extracted with DCM (100 mL). The combined organic phase was dried over anhydrous $NaSO_4$ and evaporated. The residue was dissolved in MeOH (200 mL) and cooled with an ice-bath. Aqueous $NH_4OH$ (28%, 10 mL) was added using an additional funnel. The reaction mixture was allowed to slowly warm up to room temperature and stirred at ambient temperature for 2 days. Volatiles were evaporated under vacuum. The crude product was purified by column (600 g of $SiO_2$, eluted with solvents: 1% $NH_4OH$, 4-9% MeOH, 95-90% EtOAc) give 5.1 g of pure S4-SR-cKK-E12.

Example 5-the Compound of Formula I.b.1.i (i.e., R4-SS-cKK-E12)

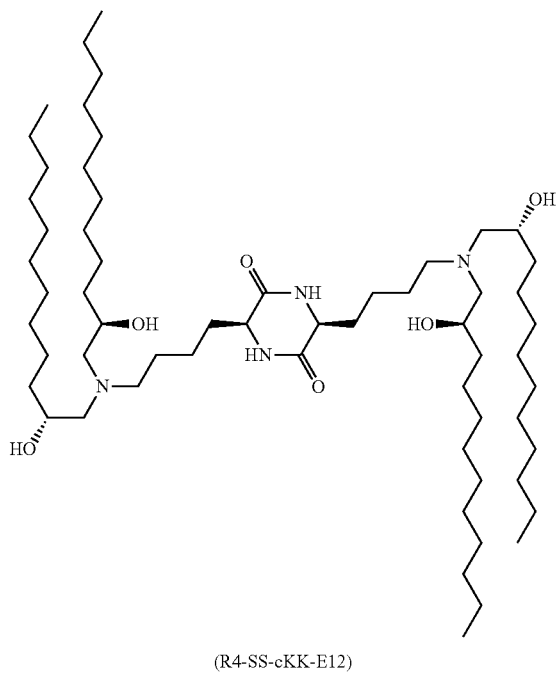 [SMILES: CCCCCCCCCC[C@@H](O)CN(CCCC[C@@H]1NC(=O)[C@H](CCCCN(C[C@H](O)CCCCCCCCCC)C[C@H](O)CCCCCCCCCC)NC1=O)C[C@H](O)CCCCCCCCCC]

(R4-SS-cKK-E12)

Scheme 6: Synthesis of the compound of Formula I.b.1.i (i.e., R4-SS-c-KK-E12).

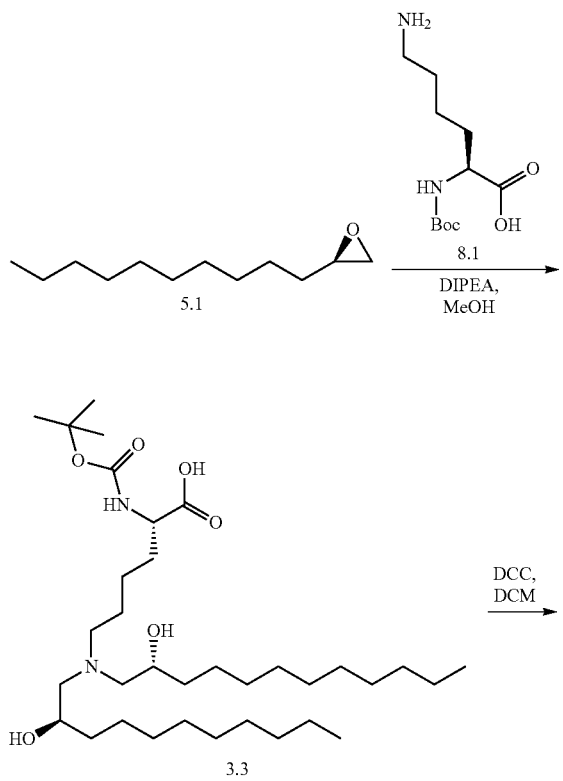

-continued

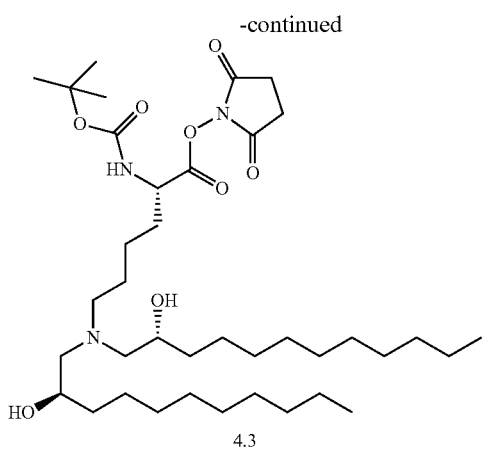

4.3

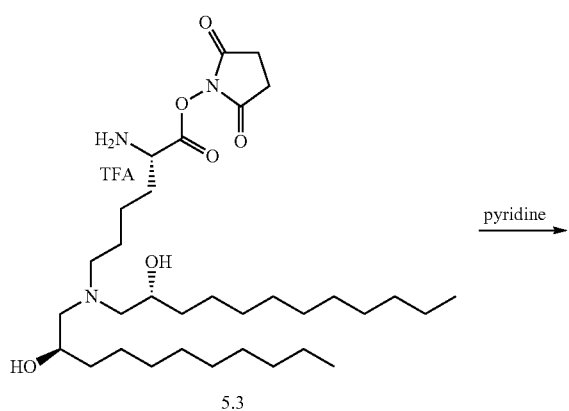

5.3

Synthesis of Compound 3.3 (N²-(tert-butoxycarbonyl)-N⁶,N⁶-bis((R)-2-hydroxydodecyl)-L-lysine):

A mixture of R-epoxide (5.1, 46 g, 250 mmol), Boc-L-Lysine 8.1 (15 g, 61 mmol), and diisopropylethylamine (11 ml) in methanol (80 ml) was stirred at room temperature for 3 d. Volatiles were removed and the yellow oily residue was purified by chromatography on silica gel (330 g) eluting with EtOAc/MeOH (100/0 to 70/30, 20 min) to give product 3.3 as a white solid (9.7 g, 26%).

Synthesis of the Compound of Formula I.b.1.i. (i.e., R4-SS-cKK-E12; ((3S,6S)-3,6-bis(4-(bis((S)-2-hydroxydodecyl)amino)butyl)piperazine-2,5-dione)):

To a solution of 3.3 (7.4 g, 12 mmol) and NHS (1.38 g, 12 mmol) in DCM (280 ml) was added DCC (2.97 g, 14.4 mmol). The reaction mixture was stirred at room temperature for 1.5 h. The solvent was then removed and the residue (crude 4.3) was dissolved in TFA (30 ml). The resulting mixture was stirred at room temperature for 1 h. TFA was then removed and DCM (30 ml) was added to the residue, and co-evaporated to remove residual TFA. The crude 5.3 was dissolved in DCM (30 mL) and added to anhydrous pyridine (480 mL) at 0° C. under N2. The resulting mixture was stirred at room temperature overnight. Pyridine was then removed and the residue was diluted with diethyl ether (300 mL). The white solid formed was removed by filtration. The filtrate was washed with aqueous Na₂CO₃ (1M, 150 ml) and brine (150 ml), dried over Na₂SO₄, and concentrated. The residue was purified by column chromatography five times (one 330 g column followed by four 80 g column) eluting with 3% NH₄OH/7% MeOH/90% EtOAc to give 1.05 g of pure R4-SS-cKK-E12 as pale gum. 1.0 g of R4-SS-cKK-E12.

Example 6-the Compound of Formula I.b.1.ii (i.e., S4-SS-cKK-E12)

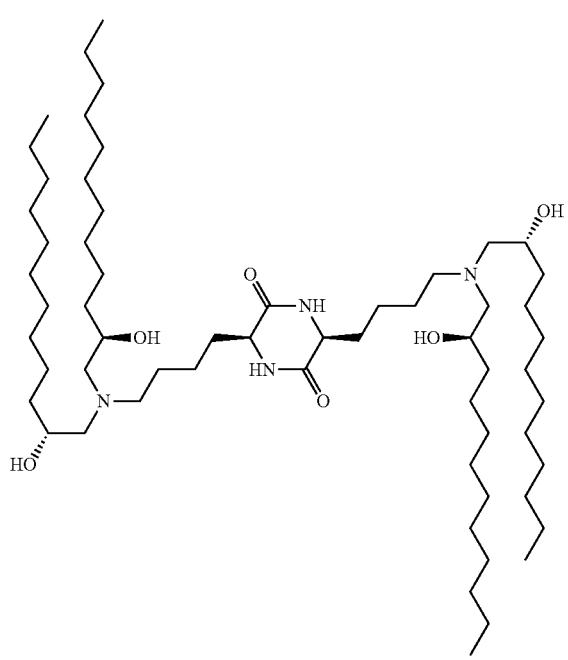

R4-SS-cKK-E12

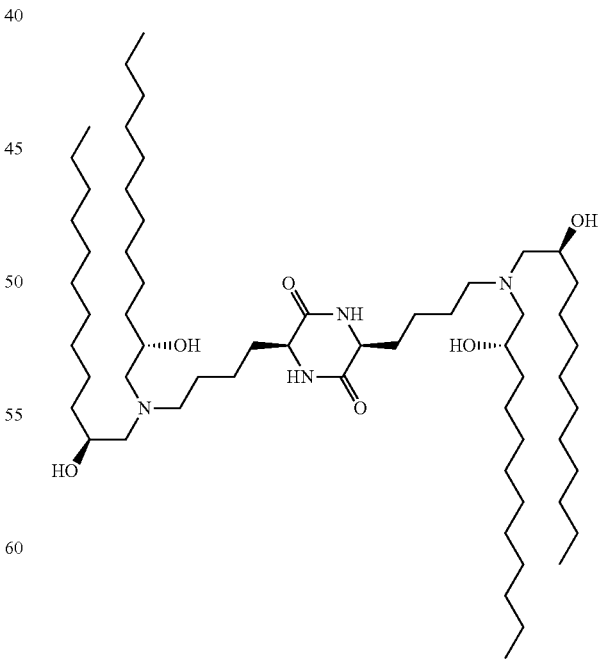

S4-SS-cKK-E12

Scheme 7: Synthesis of the compound of Formula I.b.1.ii
(i.e., S4-SS-c-KK-E12)

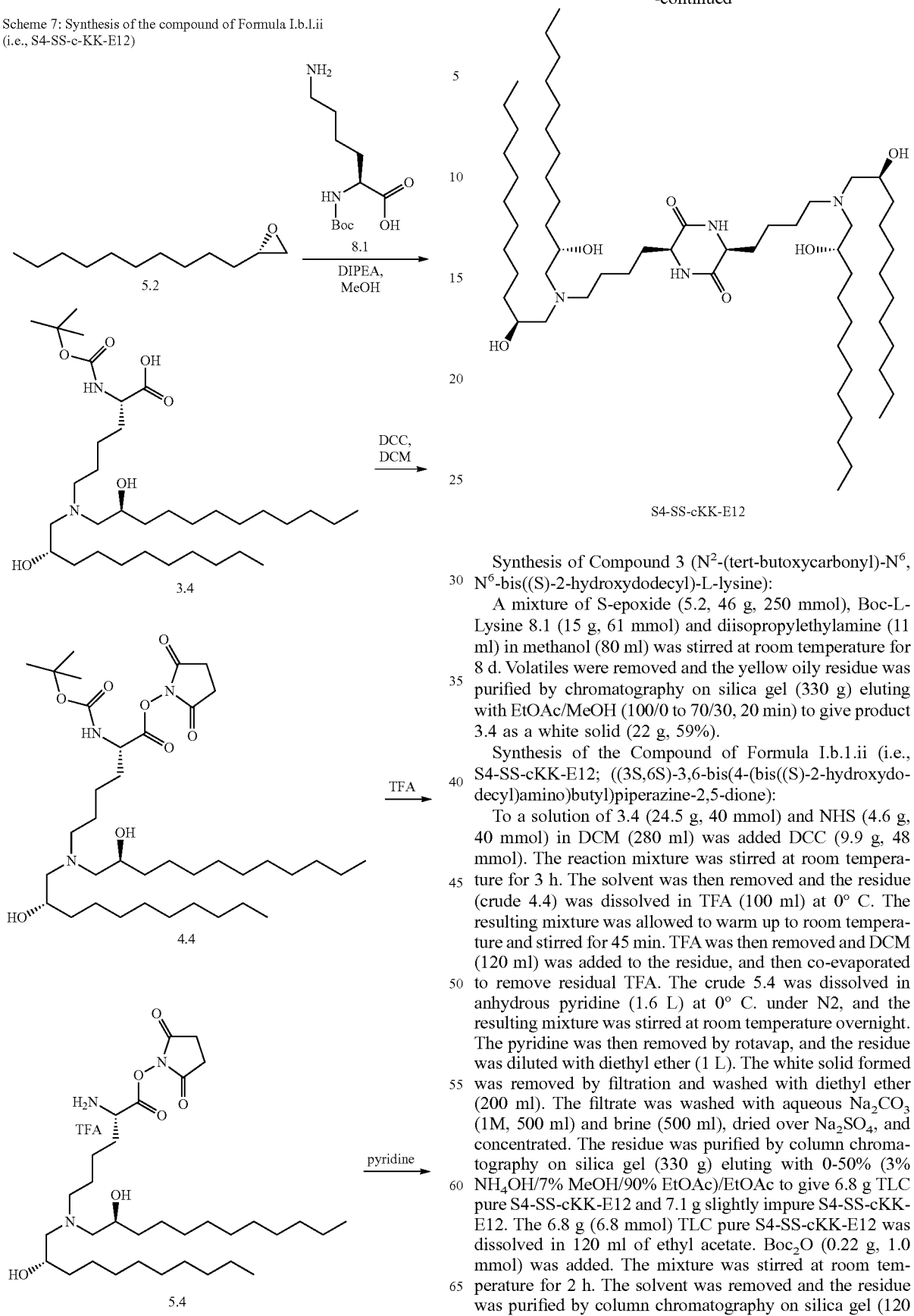

S4-SS-cKK-E12

Synthesis of Compound 3 ($N^2$-(tert-butoxycarbonyl)-$N^6$, $N^6$-bis((S)-2-hydroxydodecyl)-L-lysine):

A mixture of S-epoxide (5.2, 46 g, 250 mmol), Boc-L-Lysine 8.1 (15 g, 61 mmol) and diisopropylethylamine (11 ml) in methanol (80 ml) was stirred at room temperature for 8 d. Volatiles were removed and the yellow oily residue was purified by chromatography on silica gel (330 g) eluting with EtOAc/MeOH (100/0 to 70/30, 20 min) to give product 3.4 as a white solid (22 g, 59%).

Synthesis of the Compound of Formula I.b.1.ii (i.e., S4-SS-cKK-E12; ((3S,6S)-3,6-bis(4-(bis((S)-2-hydroxydodecyl)amino)butyl)piperazine-2,5-dione):

To a solution of 3.4 (24.5 g, 40 mmol) and NHS (4.6 g, 40 mmol) in DCM (280 ml) was added DCC (9.9 g, 48 mmol). The reaction mixture was stirred at room temperature for 3 h. The solvent was then removed and the residue (crude 4.4) was dissolved in TFA (100 ml) at 0° C. The resulting mixture was allowed to warm up to room temperature and stirred for 45 min. TFA was then removed and DCM (120 ml) was added to the residue, and then co-evaporated to remove residual TFA. The crude 5.4 was dissolved in anhydrous pyridine (1.6 L) at 0° C. under N2, and the resulting mixture was stirred at room temperature overnight. The pyridine was then removed by rotavap, and the residue was diluted with diethyl ether (1 L). The white solid formed was removed by filtration and washed with diethyl ether (200 ml). The filtrate was washed with aqueous $Na_2CO_3$ (1M, 500 ml) and brine (500 ml), dried over $Na_2SO_4$, and concentrated. The residue was purified by column chromatography on silica gel (330 g) eluting with 0-50% (3% $NH_4OH$/7% MeOH/90% EtOAc)/EtOAc to give 6.8 g TLC pure S4-SS-cKK-E12 and 7.1 g slightly impure S4-SS-cKK-E12. The 6.8 g (6.8 mmol) TLC pure S4-SS-cKK-E12 was dissolved in 120 ml of ethyl acetate. $Boc_2O$ (0.22 g, 1.0 mmol) was added. The mixture was stirred at room temperature for 2 h. The solvent was removed and the residue was purified by column chromatography on silica gel (120 g) eluting with 0-50% (3% $NH_4OH$/7% MeOH/90%

EtOAc/EtOAc to give 5.7 g (84%) of pure product S4-SS-cKK-E12 which was free of an amine side product.
Example 7-the Compound of Formula I.b.2.i (i.e., R4-RR-cKK-E12)
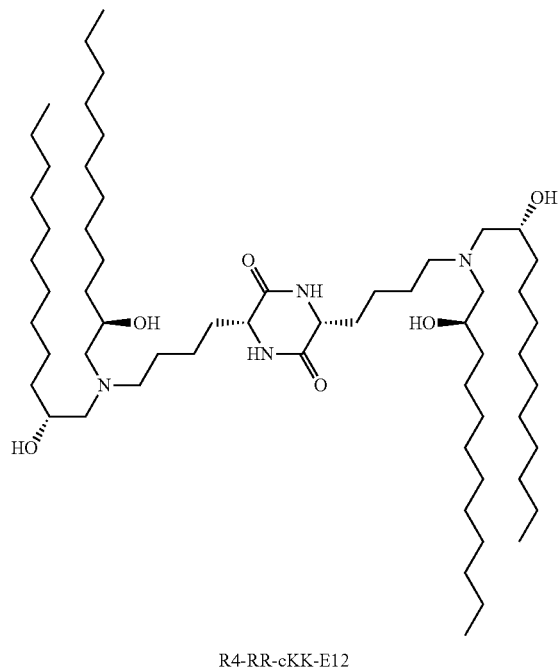 [SMILES: CCCCCCCCCC[C@@H](O)CN(CCCC[C@H]1NC(=O)[C@@H](CCCCN(C[C@H](O)CCCCCCCCCC)C[C@H](O)CCCCCCCCCC)NC1=O)C[C@H](O)CCCCCCCCCC]
R4-RR-cKK-E12
Scheme 8: Synthesis of the compound of Formula I.b.2.i (i.e., R4-RR-cKK-E12)
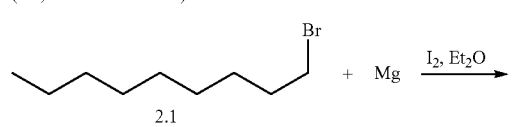
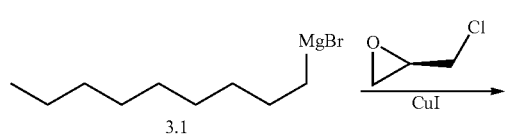
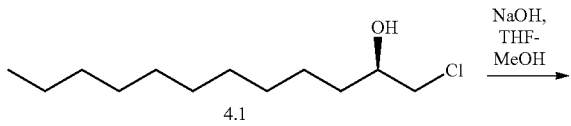
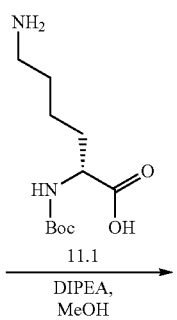
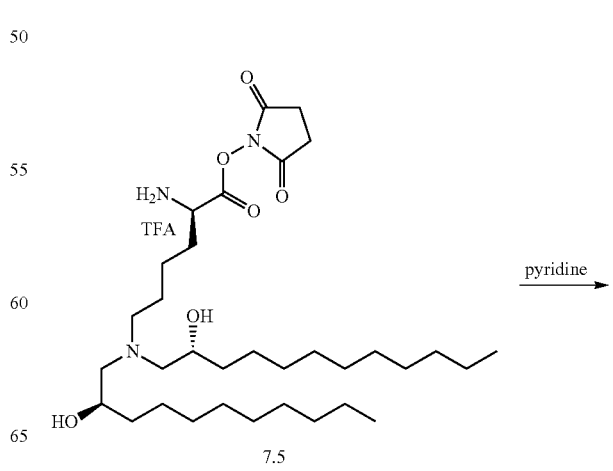

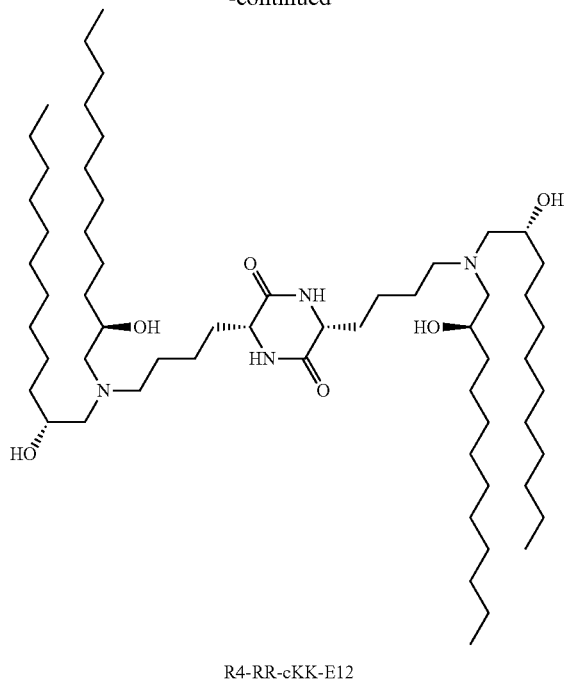

R4-RR-cKK-E12

Synthesis of Compound 3.1:

To magnesium (60 g) suspended in anhydrous Et₂O (0.9 L) was added 1-bromononane 2.1 (20 mL), followed by addition of a catalytic amount of iodine (50 mg). The resulting mixture was heated with a hot water bath until reaction of Mg with 2.1 started. The bath was removed and the remaining 1-bromononane (379.1 mL) was added to maintain a gentle reflux. After addition of 2.1 the reflux was maintained by a hot water bath for another 30 min. The resulting Grignard solution of 3.1 was cooled and used directly in next step.

Synthesis of Compound 4.1:

To CuI (38.1 g) suspended in THF (1.5 L) at −78° C. was added R-(−)-epichlorohydrin (156.8 mL). Then the above Grignard solution of 3.1 was added via a cannula while the reaction temperature was maintained at <−65° C. The resulting reaction mixture was stirred at −78° C. for an additional 3 hour. Then, saturated aqueous ammonium chloride solution (0.8 L) was added carefully, followed by addition of water (1.0 L). The resulting mixture was stirred and allowed to warm up to room temperature. The organic layer was separated, and the aqueous layer was extracted with Et₂O (0.5 L×2). The organic layer was combined with the Et₂O extracts and the resulting solution was washed with brine (0.5 L×2), and dried over anhydrous magnesium sulfate. Solvents were evaporated under vacuum, and the resulting residue was purified on a silica gel column (hexanes to 20% EtOAc/hexanes) to provide 4.1 (243.5 g, 55%) as a yellow oil.

Synthesis of Compound 5.1:

To a solution of 4.1 (243.49 g) in 1:2.6 MeOH-THF (3.6 L) stirred at 0° C. was slowly added aqueous NaOH solution (1.5 M, 0.89 L, 1.33 mole). The resulting mixture was allowed to warm up and stirred at room temperature for 3 h. TLC analysis showed complete disappearance of 4.1. Organic solvents were evaporated, and the aqueous layer was extracted with Et₂O (1 L+500 mL×2). The organic extracts were combined, washed with brine (600 mL), and dried over anhydrous magnesium sulfate. Solvents were evaporated under vacuum to give a residue which was purified on silica gel column (hexanes to 10% EtOAc/hexanes) to provide the epoxide 5.1 (193.7 g, 95%) as a light yellow oil.

Synthesis of Compound 12.1:

A mixture of N-Boc-D-Lysine 11.1 (49.2 g, 0.2 mole) and the epoxide 5.1 (147.2 g, 0.8 mole) in MeOH (1.04 L) was stirred at room temperature. DIPEA (51.9 g, 0.4 mole) was added. The resulting mixture was then stirred for 8 days, and then concentrated to dryness. The residue was purified on a silica gel column (2 kg, MeOH/DCM, 0 to 10%) to give 49.2 g of mostly pure 12.1 (MZ-550-180) and 58.3 g of impure 12.1, which was purified by a second column (1.5 kg, MeOH/EtOAc, 10 to 40%) to give 41.4 g of mostly pure 12.1. The two mostly pure batches were combined and stirred with EtOAc (0.5 L) for 3 h. The mixture was filtered to give 41.4 g pure 12.1 as a white solid. The filtrate was concentrated to dryness. The residue was stirred with EtOAc (0.1 L) for 1 h and filtered to give 10.6 g of pure 12.1. The filtrate was concentrated to dryness and the residue was purified on a silica gel column (330 g, MeOH/EtOAc, 10 to 40%) to give a third batch of 26.9 g pure 12.1. A total of 78.9 g of pure 12.1 was obtained. Yield: 64%

Preparation of the Compound of Formula I.b.2.i (i.e., R4-RR-cKK-E12):

Batch 1: To a solution of 12.1 (6.14 g, 10 mmol) and N-hydroxysuccimide (1.15 g, 10 mmol) in DCM (70 mL) was added DCC (2.47 g, 12 mmol). The resulting mixture was stirred at room temperature for 3 h. Volatiles were evaporated under vacuum to give a residue (NHS ester 6.5), which was dissolved in TFA (25 mL) and stirred for 0.5 h. TFA was removed under vacuum, and the residue (compound 7.5) was cooled to 0° C. Pyridine (anhydrous, 400 mL) was added, and the reaction mixture was stirred at room temperature for 2 h. Pyridine was removed under vacuum, and the residue was suspended in Et₂O (300 mL). The solid was removed by filtration. The filtrate was washed with 1 M Na₂CO₃ aqueous solution (150 mL) and brine (150 mL), dried over anhydrous magnesium sulfate, and concentrated to dryness. The residue was separated by column chromatograph (80 g, 7:3 MeOH—NH₃—H₂O (4× with EtOAc)/EtOAc, 0 to 50%) to give R4-RR-cKK-E12 as gummy solid (2.22 g). Multiple precipitations and triturations from EtOAc gave pure R4-RR-cKK-E12 (0.46 g) as a gum.

Example 8-the Compound of Formula I.b.2.ii (i.e., S4-RR-cKK-E12)

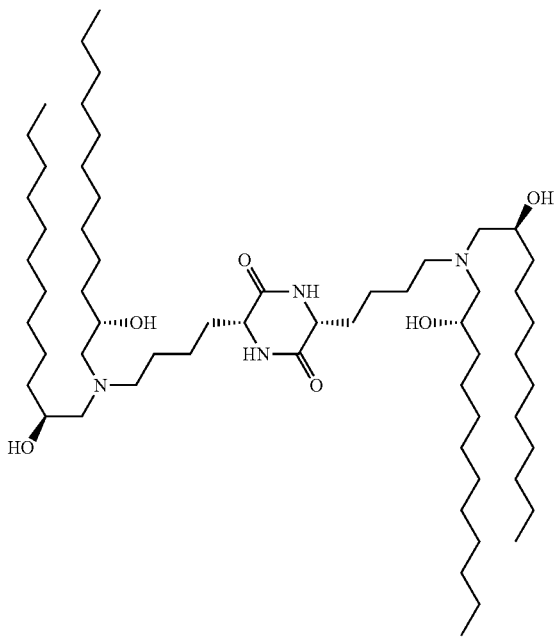

S4-RR-cKK-E12

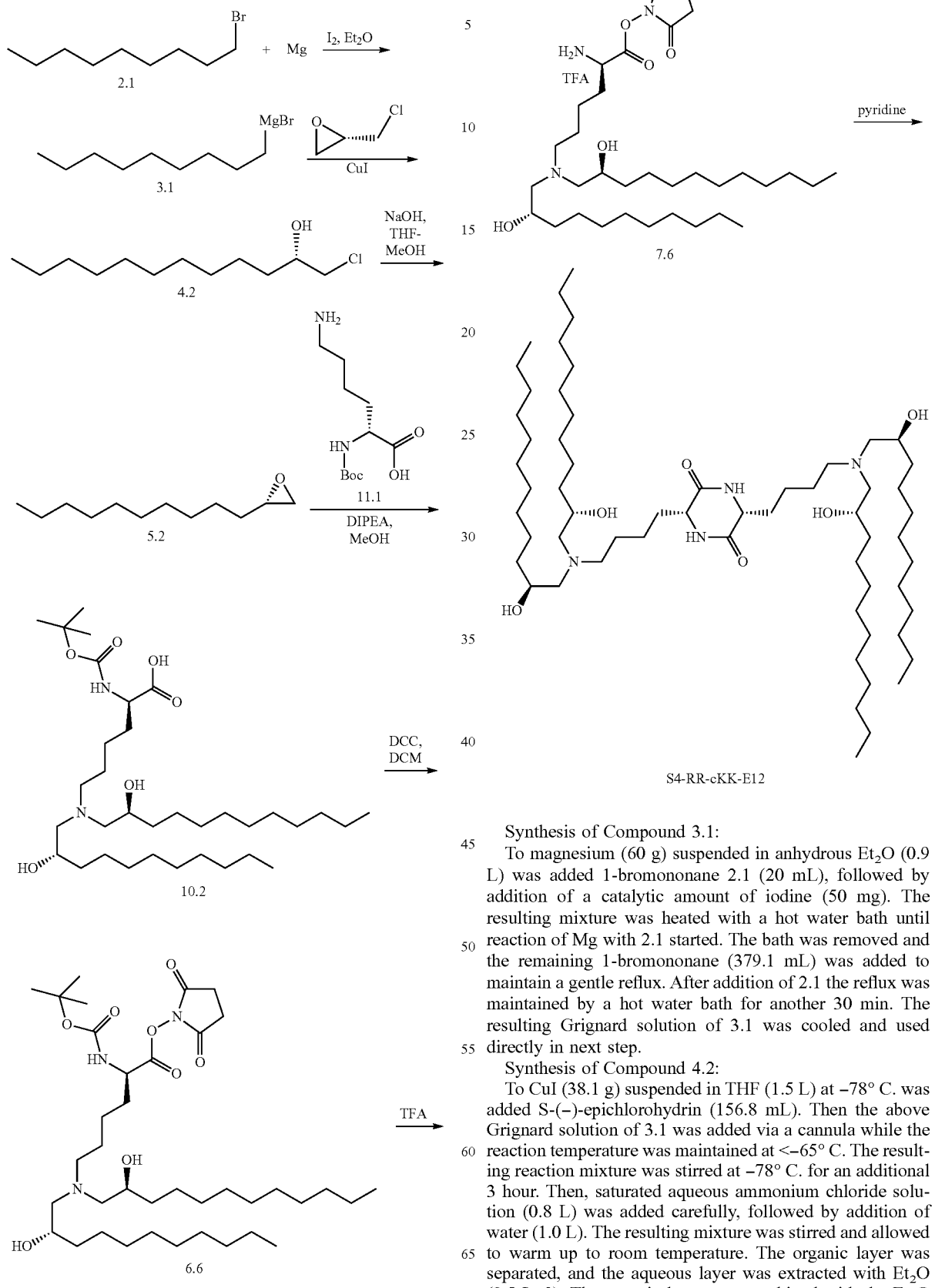

Synthesis of Compound 3.1:

To magnesium (60 g) suspended in anhydrous Et₂O (0.9 L) was added 1-bromononane 2.1 (20 mL), followed by addition of a catalytic amount of iodine (50 mg). The resulting mixture was heated with a hot water bath until reaction of Mg with 2.1 started. The bath was removed and the remaining 1-bromononane (379.1 mL) was added to maintain a gentle reflux. After addition of 2.1 the reflux was maintained by a hot water bath for another 30 min. The resulting Grignard solution of 3.1 was cooled and used directly in next step.

Synthesis of Compound 4.2:

To CuI (38.1 g) suspended in THF (1.5 L) at −78° C. was added S-(−)-epichlorohydrin (156.8 mL). Then the above Grignard solution of 3.1 was added via a cannula while the reaction temperature was maintained at <−65° C. The resulting reaction mixture was stirred at −78° C. for an additional 3 hour. Then, saturated aqueous ammonium chloride solution (0.8 L) was added carefully, followed by addition of water (1.0 L). The resulting mixture was stirred and allowed to warm up to room temperature. The organic layer was separated, and the aqueous layer was extracted with Et₂O (0.5 L×2). The organic layer was combined with the Et₂O extracts and the resulting solution was washed with brine (0.5 L×2), and dried over anhydrous magnesium sulfate. Solvents were evaporated under vacuum, and the residue was purified on a silica gel column (hexanes to 20% EtOAc/hexanes) to provide 4.2 (250.8 g, 57%) as a light yellow oil.

Synthesis of Compound 5.2:

To a solution of 4.2 (250.8 g) in 1:2.6 MeOH-THF (3.9 L) stirred at 0° C. was added slowly aqueous NaOH solution (1.5 M, 1.36 mole, 0.90 L). The resulting mixture was allowed to warm up and stirred at room temperature for 3 h. TLC analysis showed complete disappearance of 4.2. Organic solvents were evaporated, and the aqueous layer was extracted with $Et_2O$ (1 L+500 mL×2). The organic extracts were combined, washed with brine (600 mL), and dried over anhydrous magnesium sulfate. Solvents were evaporated under vacuum to give a residue which was purified on silica gel column (hexanes to 10% EtOAc/hexanes) to provide 5.2 (195.4 g, 93%) as a light yellow oil.

A mixture of N-Boc-D-Lysine 11.1 (49.2 g, 0.2 mole) and the epoxide 5.2 (147.2 g, 0.8 mole) in MeOH (1.04 L) was stirred at room temperature. DIPEA (51.9 g, 0.4 mole) was added. The resulting mixture was then stirred for 8 days, and then concentrated to dryness. The resulting residue was purified on a silica gel column (2 kg, MeOH/EtOAc, 10 to 30%) to give 10.2 (79.9 g, 65%) as a white solid.

Preparation of the Compound of Formula I.b.2.ii (i.e., S4-RR-cKK-E12)

To a solution of 10.2 (61.4 g, 100 mmol) and N-hydroxysuccimide (11.5 g, 100 mmol) in DCM (800 mL) was added DCC (24.7 g, 120 mmol). The resulting mixture was stirred at room temperature for 4 h. Volatiles were evaporated under vacuum to give a residue (NHS ester 6.6), which was dissolved in TFA (25 mL) and stirred for 40 min. TFA was removed under vacuum, and the residue (compound 7.6) was cooled to 0° C. Pyridine (anhydrous, 3.5 L) was added, and the reaction mixture was stirred at room temperature for 19 h. Pyridine was removed under vacuum, and the residue was suspended in $Et_2O$ (3.0 L). The solid was removed by filtration. The filtrate was washed with 1 M aqueous $Na_2CO_3$ solution (1.0 L) and brine (1.0 L), dried over anhydrous magnesium sulfate, and concentrated to dryness. The residue was purified by column chromatograph (4×330 g silica gel column eluting with (7% MeOH/3% $NH_3$—$H_2O$/90% EtOAc)/EtOAc, 0 to 50%) to provide S4-RR-cKK-E12 as a gummy solid (15.9 g, 16%)

Example 9-Formulations

The formulations described herein consisted of a multi-component lipid mixture of varying ratios employing one or more cationic lipids, helper lipids and PEGylated lipids designed to encapsulate various nucleic acid-based materials. The cationic lipid utilized throughout is the compound of formula I (3,6-bis(4-(bis(2-hydroxydodecyl)amino)butyl) piperazine-2,5-dione). Helper lipids can include (but not exclusively) DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG („2-dioleoyl-sn-glycero-3-phospho-(1'-rac-glycerol)), cholesterol, etc. The PEGylated lipids can include (but not exclusively) a poly(ethylene) glycol chain of up to 5 kDa in length covalently attached to a lipid with alkyl chain(s) of $C_6$-$C_{20}$ length.

Messenger RNA Material

Human Factor IX (FIX), codon-optimized Firefly Luciferase (FFL) and codon-optimized human argininosuccinate synthetase (ASS1) messenger RNA were synthesized by in vitro transcription from a plasmid DNA template encoding the gene, which was followed by the addition of a 5' cap structure (Cap 1) (Fechter, P.; Brownlee, G. G. "Recognition of mRNA cap structures by viral and cellular proteins" J. Gen. Virology 2005, 86, 1239-1249) and a 3' poly(A) tail of approximately 250 nucleotides (SEQ ID NO: 3) in length as determined by gel electrophoresis. 5' and 3' untranslated regions present in each mRNA product are represented as X and Y, respectively and defined as stated (vide infra).

Codon-Optimized Human Argininosuccinate Synthetase (ASS1) mRNA:

(SEQ ID NO: 4)
XAUGAGCAGCAAGGGCAGCGUGGUGCUGGCCUACAGCGGCGGCCUGGACA

CCAGCUGCAUCCUGGUGUGGCUGAAGGAGCAGGGCUACGACGUGAUCGCC

UACCUGGCCAACAUCGGCCAGAAGGAGGACUUCGAGGAGGCCCGCAAGAA

GGCCCUGAAGCUGGGCGCCAAGAAGGUGUUCAUCGAGGACGUGAGCCGCG

AGUUCGUGGAGGAGUUCAUCUGGCCCGCCAUCCAGAGCAGCGCCCUGUAC

GAGGACCGCUACCUGCUGGGCACCAGCCUGGCCCGCCCCUGCAUCGCCCG

CAAGCAGGUGGAGAUCGCCCAGCGCGAGGGCGCCAAGUACGUGAGCCACG

GCGCCACCGGCAAGGGCAACGACCAGGUGCGCUUCGAGCUGAGCUGCUAC

AGCCUGGCCCCCCAGAUCAAGGUGAUCGCCCCCUGGCGCAUGCCCGAGUU

CUACAACCGCUUCAAGGGCCGCAACGACCUGAUGGAGUACGCCAAGCAGC

ACGGCAUCCCCAUCCCCGUGACCCCCAAGAACCCCUGGAGCAUGGACGAG

AACCUGAUGCACAUCAGCUACGAGGCCGGCAUCCUGGAGAACCCCAAGAA

CCAGGCCCCCCCGGCCUGUACACCAAGACCCAGGACCCCGCCAAGGCCC

CCAACACCCCCGACAUCCUGGAGAUCGAGUUCAAGAAGGGCGUGCCCGUG

AAGGUGACCAACGUGAAGGACGGCACCACCCACCAGACCAGCCUGGAGCU

GUUCAUGUACCUGAACGAGGUGGCCGGCAAGCACGGCGUGGGGCCGCAUCG

ACAUCGUGGAGAACCGCUUCAUCGGCAUGAAGAGCCGCGGCAUCUACGAG

ACCCCCGCCGGCACCAUCCUGUACCACGCCCACCUGGACAUCGAGGCCUU

CACCAUGGACCGCGAGGUGCGCAAGAUCAAGCAGGGCCUGGGCCUGAAGU

UCGCCGAGCUGGUGUACACCGGCUUCUGGCACAGCCCCGAGUGCGAGUUC

GUGCGCCACUGCAUCGCCAAGAGCCAGGAGCGCGUGGAGGGCAAGGUGCA

GGUGAGCGUGCUGAAGGGCCAGGUGUACAUCCUGGGCCGCGAGAGCCCCC

UGAGCCUGUACAACGAGGAGCUGGUGAGCAUGAACGUGCAGGGCGACUAC

GAGCCCACCGACGCCACCGGCUUCAUCAACAUCAACAGCCUGCGCCUGAA

GGAGUACCACCGCCUGCAGAGCAAGGUGACCGCCAAGUGAY

5' and 3' UTR Sequences

X=

(SEQ ID NO: 5)
GGACAGAUCGCCUGGAGACGCCAUCCACGCUGUUUUGACCUCCAUAGAAG

ACACCGGGACCGAUCCAGCCUCCGCGGCCGGGAACGGUGCAUUGGAACGC

GGAUUCCCCGUGCCAAGAGUGACUCACCGUCCUUGACACG

Y=

(SEQ ID NO: 6)
CGGGUGGCAUCCCUGUGACCCCUCCCCAGUGCCUCUCCUGGCCCUGGAAG

UUGCCACUCCAGUGCCCACCAGCCUUGUCCUAAUAAAAUUAAGUUGCAUC

Aliquots of 50 mg/mL ethanolic solutions of one or more compounds of formula I, DOPE, Cholesterol and DMG-PEG2K were mixed and diluted with ethanol to 3 mL final volume. Separately, an aqueous buffered solution (10 mM citrate/150 mM NaCl, pH 4.5) of ASS1 mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=0.64 mg/mL ASS1 mRNA (encapsulated). $Z_{ave}$=78 nm ($Dv_{(50)}$=46 nm; $Dv_{(90)}$=96 nm).

Example 10-Analysis of ASS1 Protein Produced Via Intravenously Delivered ASS1 mRNA-Loaded Nanoparticles Injection Protocol All studies were performed using male CD-1 mice of approximately 6-8 weeks of age at the beginning of each experiment. Samples were introduced by a single bolus tail-vein injection of an equivalent total dose of 1.0 mg/kg (or otherwise specified) of encapsulated ASS1 mRNA. Mice were sacrificed and perfused with saline at the designated time points.

Isolation of Organ Tissues for Analysis

The liver, spleen, kidney and heart of each mouse was harvested, apportioned into separate parts, and stored in either 10% neutral buffered formalin or snap-frozen and stored at −80° C. for analysis.

Isolation of Plasma for Analysis

All animals were euthanized by $CO_2$ asphyxiation at designated time points post dose administration (±5%) followed by thoracotomy and terminal cardiac blood collection. Whole blood (maximal obtainable volume) will be collected via cardiac puncture on euthanized animals into serum separator tubes, allowed to clot at room temperature for at least 30 minutes, centrifuged at 22° C.±5° C. at 9300 g for 10 minutes, and the serum will be extracted. For interim blood collections, approximately 40-50 µL of whole blood will be collected via facial vein puncture or tail snip. Samples collected from non treatment animals were used as a baseline ASS1 levels for comparison to study animals.

Enzyme-Linked Immunosorbent Assay (ELISA) Analysis

Human ASS1 ELISA: Standard ELISA procedures were followed employing mouse anti-ASS1 2D1-2E12 IgG as the capture antibody with rabbit anti-ASS1 #3285 IgG as the secondary (detection) antibody (Shire Human Genetic Therapies). Horseradish peroxidase (HRP)-conjugated goat anti-rabbit IgG was used for activation of the 3,3',5,5'-tetramethylbenzidine (TMB) substrate solution. The reaction was quenched using 2N $H_2SO_4$ after 20 minutes. Detection was monitored via absorption (450 nm) on a Molecular Device SpectraMax instrument. Untreated mouse serum and organs and human ASS1 protein were used as negative and positive controls, respectively.

Example 11-In Vivo Human ASS1 Protein Production

The production of human ASS1 protein via codon-optimized hASS1 mRNA-loaded lipid nanoparticles, comprising compounds of formula I, was tested in CD-1 mice as a single, bolus intravenous injection, as described above. FIG. 1 depicts the amount of human ASS1 protein detected via ELISA when treating mice human ASS1 mRNA-loaded lipid nanoparticles, with various racemic and chiral compounds of formula I, at 1.0 mg/kg doses. The mice were sacrificed twenty-four hours post-injection and organs, such as livers, were harvested.

Example 12-Toxicity Studies

Expression levels of alanine aminotransferase (ALT) and aspartate aminotransferase (AST) were measured for various racemic and chiral compounds of formula I. Increased expression levels of AST and/or ALT generally caused by agents that cause liver toxicity. The chiral compounds of formula I generally yielded lower expression levels of ALT and/or AST, i.e., correlating to lower liver toxicity issues, compared to stereochemically non-enriched, or stereochemically less enriched, compositions of the same lipid. See Tables 1 and 2 below.

TABLE 1

| Structure | ALT (U/L) | AST (U/L) | ASS1 (ng/mg Total Protein) |
|---|---|---|---|
| Racemic Mixture | 190 ± 43 | 212 ± 54 | 471 ± 309 |
|  | 201 ± 89 | 403 ± 42 | 937 ± 337 |
|  | 207 ± 84 | 425 ± 169 | 497 ± 213 |
|  | 344 ± 57 | 555 ± 122 | 1387 ± 593 |
|  | 426 ± 112 | 757 ± 158 | 1509 ± 598 |
|  | 457 ± 274 | 728 ± 126 | 910 ± 327 |
|  | 503 ± 201 | 653 ± 133 | 1010 ± 154 |
|  | 618 ± 503 | 638 ± 273 | 209 ± 169 |
| $S_4$ with | 170 ± 40 | 132 ± 44 | 375 ± 244 |
| Racemic Lysine Core | 155 ± 57 | 157 ± 38 | 674 ± 147 |
| $R_4$ with | 188 ± 22 | 265 ± 122 | 823 ± 215 |
| Racemic Lysine Core | 236 ± 163 | 237 ± 139 | 568 ± 248 |
| Racemic —OH with | 378 ± 58 | 622 ± 76 | 117 ± 80 |
| SS Lysine Core | 618 ± 503 | 638 ± 273 | 209 ± 169 |
| $S_4$-S,S-cKKE12 | 226 ± 71 | 384 ± 233 | 1121 ± 468 |
| $R_4$-S,S-cKKE12 | 175 ± 102 | 144 ± 35 | 449 ± 105 |
| $S_4$-S,R-cKKE12 | 190 ± 75 | 193 ± 71 | 2303 ± 491 |
| $R_4$-S,R-cKKE12 | 75 ± 13 | 82 ± 12 | 264 ± 317 |
|  | 86 ± 27 | 119 ± 32 | 1369 ± 233 |
|  | 94 ± 22 | 88 ± 16 | 467 ± 149 |
|  | 59 ± 13 | 73 ± 18 | 401 ± 137 |
|  | 139 ± 28 | 177 ± 73 | 1182 ± 150 |
|  | 180 ± 19 | 141 ± 25 | 750 ± 324 |
|  | 269 ± 80 | 424 ± 156 | 2790 ± 464 |
|  | 123 ± 39 | 124 ± 22 | 1113 ± 35 |
|  | 60 ± 4 | 49 ± 5 | 846 ± 226 |
|  | 70 ± 10 | 78 ± 24 | 1082 ± 189 |

TABLE 2 cKK-E12 of a single intravenous dose. 24 hours post-formulation used for screening was cKK-E12:DOPE:Chol:DMG-PEG2K

| | Structure Assignment | ALT | AST |
|---|---|---|---|
| Lot #1 | 'Racemic' Mixture | 885 ± 489 | 982 ± 350 |
|  |  | 207 ± 84 | 425 ± 169 |
|  |  | 504 ± 317 | 657 ± 176 |
|  |  | 503 ± 201 | 653 ± 133 |
| Lot #2 |  | 365 ± 152 | 604 ± 136 |
|  |  | 401 ± 265 | 586 ± 193 |
| Lot #3 |  | 197 ± 50 | 309 ± 33 |
| Lot #1 | $S_4$-SS | 226 ± 71 | 384 ± 233 |
| Lot #1 | $R_4$-SS | 175 ± 102 | 144 ± 35 |

TABLE 2-continued cKK-E12 of a single intravenous dose. 24 hours post-formulation used for screening was cKK-E12:DOPE:Chol:DMG-PEG2K

| | Structure Assignment | ALT | AST |
|---|---|---|---|
| Lot #1 | S$_4$-RR | 152 ± 9 | 180 ± 42 |
| Lot #1 | R$_4$-RR | 136 ± 34 | 194 ± 80 |
| Lot #1 | S$_4$-RS/SR | 143 ± 29 | 240 ± 98 |
| | | 189 ± 47 | 203 ± 87 |
| Lot #2 | | 190 ± 75 | 193 ± 71 |
| Lot #1 | R$_4$-RS/SR | 86 ± 27 | 119 ± 32 |
| | | 75 ± 13 | 82 ± 12 |
| | | 76 ± 4 | 79 ± 4 |
| | | 94 ± 22 | 88 ± 16 |
| Lot #2 | | 269 ± 80 | 424 ± 156 |
| | | 139 ± 28 | 177 ± 73 |
| | | 180 ± 19 | 141 ± 25 |
| | | 91 ± 13 | 98 ± 18 |
| Lot #3 | | 125 ± 47 | 104 ± 27 |
| Lot #4 | | 94 ± 24 | 91 ± 14 |
| Lot #5 | | 60 ± 4 | 49 ± 5 |
| Lot #6 | | 70 ± 10 | 78 ± 24 |
| Lot #7 | | 308 ± 115 | 354 ± 128 |
| | | 123 ± 39 | 124 ± 22 |

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The invention claimed is:
1. A lipid nanoparticle comprising:
a polynucleotide that is messenger RNA (mRNA);
one or more non-cationic lipids that are not a cholesterol-based lipid, one or more cholesterol-based lipids and/or one or more PEG-modified lipids;
and
one or more chemical entities of formula I, each of which is a compound of formula I:

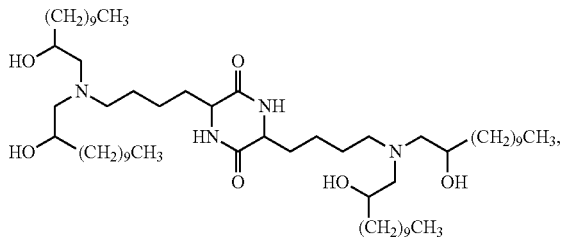

I or
a pharmaceutically acceptable salt thereof,
wherein 70% or more of the chemical entities of formula I have the structure set forth by formula I.a.i,

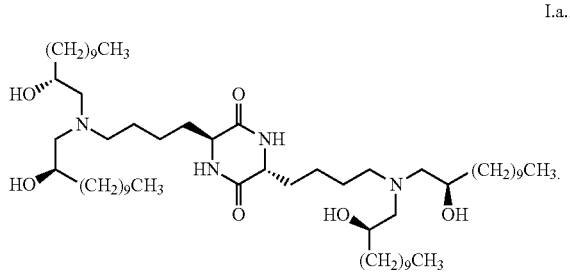

I.a.i

2. The lipid nanoparticle of claim 1, wherein 80% or more of the chemical entities of formula I have the structure set forth by formula I.a.i.

3. The lipid nanoparticle of claim 1, wherein 90% or more of the chemical entities of formula I have the structure set forth by formula I.a.i.

4. The lipid nanoparticle of claim 1, wherein 95% or more of the chemical entities of formula I have the structure set forth by formula I.a.i.

5. A method of delivery of messenger RNA (mRNA) in vivo, comprising
administering to a subject in need of delivery the lipid nanoparticle of claim 1, wherein administering of the lipid nanoparticle results in the expression of the protein encoded by the mRNA in vivo.

6. A method of treating a disease or disorder comprising the step of delivering an mRNA encoding a therapeutic protein using the lipid nanoparticle of claim 1.

7. The lipid nanoparticle of claim 1, wherein the one or more non-cationic lipids are selected from the group consisting of DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), and DOPG (1,2-dioleoyl-sn-glycero-3-phospho-(1'-rac-glycerol)).

8. The lipid nanoparticle of claim 1, wherein the one or more cholesterol-based lipids are cholesterol and/or PEGylated cholesterol.

9. The lipid nanoparticle of claim 1, wherein the one or more PEG-modified lipids comprise a poly(ethylene) glycol chain of up to 5 kDa covalently attached to a lipid with alkyl chain(s) of $C_6$-$C_{20}$ length.

10. A method of delivery of messenger RNA (mRNA) in vivo, comprising administering to a subject in need of delivery the lipid nanoparticle of claim 7, wherein administering of the lipid nanoparticle results in the expression of the protein encoded by the mRNA in vivo.

11. A method of delivery of messenger RNA (mRNA) in vivo, comprising administering to a subject in need of delivery the lipid nanoparticle of claim 8, wherein administering of the lipid nanoparticle results in the expression of the protein encoded by the mRNA in vivo.

12. A method of delivery of messenger RNA (mRNA) in vivo, comprising administering to a subject in need of delivery the lipid nanoparticle of claim 9, wherein administering of the lipid nanoparticle results in the expression of the protein encoded by the mRNA in vivo.

* * * * *

```
                        SEQUENCE LISTING

<160> NUMBER OF SEQ ID NOS: 6

<210> SEQ ID NO 1
<211> LENGTH: 500
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(500)
<223> OTHER INFORMATION: This sequence may encompass 10-500 nucleotides,
      wherein some positions may be absent
<220> FEATURE:
<223> OTHER INFORMATION: See specification as filed for detailed
      description of substitutions and preferred embodiments

<400> SEQUENCE: 1
aaaaaaaaaa aaaaaaaaaa aaaaaaaaaa aaaaaaaaaa aaaaaaaaaa aaaaaaaaaa        60
aaaaaaaaaa aaaaaaaaaa aaaaaaaaaa aaaaaaaaaa aaaaaaaaaa aaaaaaaaaa       120
aaaaaaaaaa aaaaaaaaaa aaaaaaaaaa aaaaaaaaaa aaaaaaaaaa aaaaaaaaaa       180
aaaaaaaaaa aaaaaaaaaa aaaaaaaaaa aaaaaaaaaa aaaaaaaaaa aaaaaaaaaa       240
aaaaaaaaaa aaaaaaaaaa aaaaaaaaaa aaaaaaaaaa aaaaaaaaaa aaaaaaaaaa       300
aaaaaaaaaa aaaaaaaaaa aaaaaaaaaa aaaaaaaaaa aaaaaaaaaa aaaaaaaaaa       360
aaaaaaaaaa aaaaaaaaaa aaaaaaaaaa aaaaaaaaaa aaaaaaaaaa aaaaaaaaaa       420
aaaaaaaaaa aaaaaaaaaa aaaaaaaaaa aaaaaaaaaa aaaaaaaaaa aaaaaaaaaa       480
aaaaaaaaaa aaaaaaaaaa                                                   500

<210> SEQ ID NO 2
<211> LENGTH: 200
<212> TYPE: DNA
<213> ORGANISM: Artificial Sequence
```

-continued

```
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(200)
<223> OTHER INFORMATION: This sequence may encompass 10-200 nucleotides,
      wherein some positions may be absent
<220> FEATURE:
<223> OTHER INFORMATION: See specification as filed for detailed
      description of substitutions and preferred embodiments

<400> SEQUENCE: 2
cccccccccc cccccccccc cccccccccc cccccccccc cccccccccc cccccccccc      60
cccccccccc cccccccccc cccccccccc cccccccccc cccccccccc cccccccccc     120
cccccccccc cccccccccc cccccccccc cccccccccc cccccccccc cccccccccc     180
cccccccccc cccccccccc                                                  200

<210> SEQ ID NO 3
<211> LENGTH: 250
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa                                                             250

<210> SEQ ID NO 4
<211> LENGTH: 1479
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 4
ggacagaucg ccuggagacg ccauccacgc uguuuugacc uccauagaag acaccgggac      60
cgauccagcc uccgcggccg ggaacggugc auuggaacgc ggauuccccg ugccaagagu     120
gacucaccgu ccuugacacg augagcagca agggcagcgu ggugcuggcc uacagcggcg     180
gccuggacac cagcugcauc cugguguggc ugaaggagca gggcuacgac gugaucgccu     240
accuggccaa caucggccag aaggaggacu ucgaggaggc ccgcaagaag gcccugaagc     300
ugggcgccaa gaagguguuc aucgaggacg ugagccgcga guucguggag gaguucaucu     360
ggcccgccau ccagagcagc gcccuguacg aggaccgcua ccugcugggc accagccugg     420 cccgcccug cauacgccgc aagcagguggag agaucgccca gcgcgagggc gccaaguacg     480
```

```
ugagccacgg cgccaccggc aagggcaacg accaggugcg cuucgagcug agcugcuaca      540
gccuggcccc ccagaucaag gugaucgccc ccuggcgcau gcccgaguuc acaaccgcu       600 ucaagggccg caacgaccug auggaguacg ccaagcagca cggcaucccc auccccguga      660
cccccaagaa ccccuggagc auggacgaga accugaugca caucagcuac gaggccggca      720
uccuggagaa ccccaagaac caggcccccc ccggccugua caccaagacc caggaccccg      780
ccaaggcccc caacacccccc gacauccugg agaucgaguu caagaagggc gugcccguga     840
aggugaccaa cgugaaggac ggcaccaccc accagaccag ccuggagcug uucauguacc      900
ugaacgaggu ggccggcaag cacggcgugg gccgcaucga caucguggag aaccgcuuca     960
ucggcaugaa gagccgcggc aucuacgaga ccccgccgg caccauccug uaccacgccc       1020
accuggacau cgaggccuuc accauggacc gcgaggugcg caagaucaag cagggccugg      1080
gccugaaguu cgccgagcug guguacaccg gcuucggca cagccccgag ugcgaguucg      1140
ugcgccacug caucgccaag agccaggagc gcguggaggg caaggugcag gugagcgugc      1200
ugaagggcca gguguacauc cugggccgcg agagccccu gagccuguac aacgaggagc       1260
uggugagcau gaacgugcag ggcgacuacg agcccaccga cgccaccggc uucaucaaca      1320
ucaacagccu gcgccugaag gaguaccacc gccugcagag caaggugacc gccaagugac      1380
ggguggcauc ccugugaccc cuccccagug ccucuccugg cccuggaagu ugccacucca      1440
gugcccacca gccuuguccu aauaaaauua aguugcauc                             1479

<210> SEQ ID NO 5
<211> LENGTH: 140
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 5
ggacagaucg ccuggagacg ccauccacgc uguuugacc uccauagaag acaccgggac        60
cgauccagcc uccgcggccg ggaacggugc auuggaacgc ggauucccg ugccaagagu       120 gacucaccgu ccuugacacg                                                   140

<210> SEQ ID NO 6
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 6
cggguggcau cccugugacc cuccccagu gccucuccug gcccuggaag uugccacucc         60
agugcccacc agccuugucc uaauaaaauu aaguugcauc                             100
```